(12) United States Patent
Ohkawa et al.

(10) Patent No.: US 7,199,124 B2
(45) Date of Patent: Apr. 3, 2007

(54) JNK INHIBITOR

(75) Inventors: Shigenori Ohkawa, Takatsuki (JP); Kenichi Naruo, Sanda (JP); Seiji Miwatashi, Ikeda (JP); Hiroyuki Kimura, Sakai (JP); Tomohiro Kawamoto, Takatsuki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 355 days.

(21) Appl. No.: 10/470,751

(22) PCT Filed: Feb. 1, 2002

(86) PCT No.: PCT/JP02/00828

§ 371 (c)(1),
(2), (4) Date: Jul. 30, 2003

(87) PCT Pub. No.: WO02/062792

PCT Pub. Date: Aug. 15, 2002

(65) Prior Publication Data

US 2004/0063946 A1     Apr. 1, 2004

(30) Foreign Application Priority Data

Feb. 2, 2001   (JP)   ............................. 2001-027570

(51) Int. Cl.
*C07D 403/04*   (2006.01)
*A61K 31/506*   (2006.01)
*C07D 401/04*   (2006.01)
*C07D 401/14*   (2006.01)
*A61K 31/4439*  (2006.01)

(52) U.S. Cl. ..................... 514/256; 514/275; 514/340; 514/342; 544/331; 544/333; 546/270.4; 546/271.4

(58) Field of Classification Search .............. 544/331, 544/333; 546/274.1, 270.4, 271.4; 514/256, 514/275, 341, 340, 342
See application file for complete search history.

(56) References Cited

U.S. PATENT DOCUMENTS

| 4,612,321 | A  | * | 9/1986 | Terao et al. ................. 514/338 |
| 5,658,903 | A  | * | 8/1997 | Adams et al. ............. 514/235.8 |
| 5,792,778 | A  |   | 8/1998 | de Laszlo et al. .......... 514/318 |
| 6,083,949 | A  | * | 7/2000 | Liverton et al. ........ 514/253.09 |
| 6,436,966 | B1 | * | 8/2002 | Ohkawa et al. ............. 514/340 |
| 6,962,933 | B1 | * | 11/2005 | Ohkawa et al. ............. 514/340 |
| 2002/0032183 | A1 | * | 3/2002 | LoGrasso et al. ........ 514/210.2 |
| 2004/0053973 | A1 | * | 3/2004 | Ohkawa et al. ............. 514/342 |

FOREIGN PATENT DOCUMENTS

| EP | 0 149 884 | 7/1984 |
| EP | 1070711 A2 | 1/2001 |
| EP | 1180518 A1 | 2/2002 |
| JP | 2000-302680 | 10/2000 |
| WO | WO 97/05877 | 2/1997 |
| WO | WO 97/35856 | 10/1997 |
| WO | WO 97/47618 | 12/1997 |
| WO | WO 98/52940 | 11/1998 |
| WO | WO 98/56788 | 12/1998 |
| WO | WO 99/18942 | 4/1999 |
| WO | WO 99/21555 | 5/1999 |
| WO | WO 99/32121 | 7/1999 |
| WO | WO 99/64418 | 12/1999 |
| WO | WO-00/26209 | * 5/2000 |
| WO | WO 00/31063 | 6/2000 |
| WO | WO 00/63204 | 10/2000 |
| WO | WO 00/64894 | 11/2000 |
| WO | WO 01/10865 | 2/2001 |
| WO | WO 01/12621 A1 | 2/2001 |
| WO | WO 01/30778 A1 | 5/2001 |
| WO | WO 01/57022 A2 | 8/2001 |
| WO | WO 01/74811 A2 | 10/2001 |
| WO | WO 02/10137 A2 | 2/2002 |

OTHER PUBLICATIONS

Lisnock et al., Biochemistry, 37, 16573-16581, 1998.*
Bagowski et al., Current Biology, 11, 1176-1182, 2001.*
Davis, Cell, 103, 239-252, Oct. 13, 2000.*
Omura et al., J. Mol. Cell Cardiol., 31, 1269-1279, 1999.*

(Continued)

*Primary Examiner*—Fiona T. Powers
(74) *Attorney, Agent, or Firm*—Mark Chao; Elaine M. Ramesh

(57) ABSTRACT

The present invention relates to a c-Jun N-terminal kinase inhibitor containing an azole compound (I) substituted by a nitrogen-containing aromatic group having substituent(s) (except a compound represented by the formula:

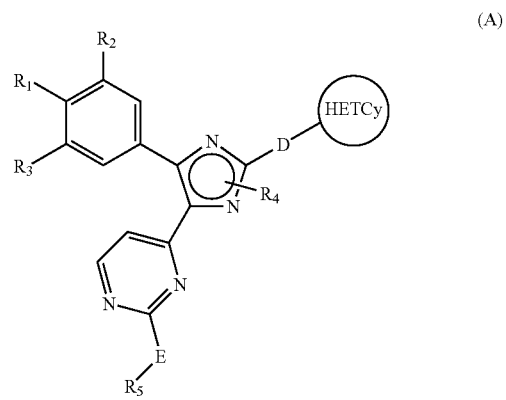

) or a salt thereof or a prodrug thereof.

6 Claims, No Drawings

OTHER PUBLICATIONS

Yue et al., Circulation Research, 82, 166-174, 1998.*
Liverton, et al. "Design and Synthesis of Potent, Selective, and Orally Bioavailable Tetrasubstituted Imidazole Inhibitors of p38 Mitogen-Activated Protein Kinase" J. Med. Chem. 42:2180-2190 (1999).

* cited by examiner

SEQUENCE LISTING

```
<160> NUMBER OF SEQ ID NOS: 8

<210> SEQ ID NO 1
<211> LENGTH: 62
<212> TYPE: DNA
<213> ORGANISM: Artificial Sequence
<220> FEATURE:
<223> OTHER INFORMATION: PCR primer

<400> SEQUENCE: 1
acaactcgag ataacatatg gctcatcatc atcatcatca tagcagaagc aagcgtgaca      60
ac                                                                    62

<210> SEQ ID NO 2
<211> LENGTH: 32
<212> TYPE: DNA
<213> ORGANISM: Artificial Sequence
<220> FEATURE:
<223> OTHER INFORMATION: PCR primer

<400> SEQUENCE: 2
tcccgggtac ctcactgctg cacctgtgct aa                                   32

<210> SEQ ID NO 3
<211> LENGTH: 62
<212> TYPE: DNA
<213> ORGANISM: Artificial Sequence
<220> FEATURE:
<223> OTHER INFORMATION: PCR primer

<400> SEQUENCE: 3
accagaattc ataacatatg gctcatcatc atcatcatca tgcggcgtcc tccctggaac      60
ag                                                                    62

<210> SEQ ID NO 4
```

```
-continued

<211> LENGTH: 31
<212> TYPE: DNA
<213> ORGANISM: Artificial Sequence
<220> FEATURE:
<223> OTHER INFORMATION: PCR primer

<400> SEQUENCE: 4
accctctaga caagcagcta cctgaagaag g                              31

<210> SEQ ID NO 5
<211> LENGTH: 44
<212> TYPE: DNA
<213> ORGANISM: Artificial Sequence
<220> FEATURE:
<223> OTHER INFORMATION: PCR primer

<400> SEQUENCE: 5
ggccgcctgg tggacgacaa agccaaggac cggagcgccg gctg                44

<210> SEQ ID NO 6
<211> LENGTH: 44
<212> TYPE: DNA
<213> ORGANISM: Artificial Sequence
<220> FEATURE:
<223> OTHER INFORMATION: PCR primer

<400> SEQUENCE: 6
cagccggcgc tccggtcctt ggctttgtcg tccaccaggc ggcc                44

<210> SEQ ID NO 7
<211> LENGTH: 34
<212> TYPE: DNA
<213> ORGANISM: Artificial Sequence
<220> FEATURE:
<223> OTHER INFORMATION: PCR primer

<400> SEQUENCE: 7
aaaagaattc atgactgcaa agatggaaac gacc                           34

<210> SEQ ID NO 8
<211> LENGTH: 39
<212> TYPE: DNA
<213> ORGANISM: Artificial Sequence
<220> FEATURE:
<223> OTHER INFORMATION: PCR primer

<400> SEQUENCE: 8
aaaagcggcc gctcacaggc gctccagctc gggcgacgc                      39
```

JNK INHIBITOR

This application is the National Phase filing of International Patent Application No. PCT/JP02/00828, filed 01 Feb. 2002.

TECHNICAL FIELD

The present invention relates to a compound having a superior c-Jun N-terminal kinase (hereinafter to be abbreviated as JNK)-inhibitory activity, and the like. More particularly, the present invention relates to a substituted azole compound having a prophylactic or therapeutic effect on cytokine-mediated diseases, which results from its cytokine production inhibitory activity based on JNK inhibitory action, and the like.

BACKGROUND ART

JNK is among the mitogen activated protein kinases (MAPKs) mediating the signaling pathway for intranuclear transmission of extracellular stimuli. It is known that JNK increases the transcription activity by phosphorylation of the N-terminal of c-Jun, which is an AP-1 transcription factor (S. Gupta, T. Barrett, A. J. Whitmarsh, J. Cavanagh, H. K. Sluss, B. Derijard, and R. J. Davis, *EMBO J.*, 15, 2760–2770 (1996), A. Minden, and M. Karin, *Biochemica et Biophysica Acta*, 1333, F85 (1997)). In other words, it is considered that JNK inhibitors inhibit expression of AP-1-dependent inflammatory and immune-factors, and are potential therapeutic drugs of inflammatory diseases such as rheumatoid arthritis and the like, and neurodegenerative diseases (J. L. Swantek, M. H. Cobb, and T. D. Geppert, *Mol. Cell. Biol.*, 1997, 17, 6274, A. C. Maroney, M. A. Glicksman, A. N. Basma, K. M. Walton, E. Knight Jr, C. A. Murphy, B. A. Bartlett, J. P. Finn, T. Angeles, Y. Matsuda, N. T. Neff, and C. A. Dionne, *J. Neurosci.*, 1998, 18, 104).

Involvement of c-Jun in myocardial apoptosis during ischemia/reperfusion has been also suggested, thereby indicating a potential of JNK for a therapeutic drug of cardiovascular diseases such as cardiac infarction, cardiac incompetence and the like (T.-L. Yue, X.-L. Ma, X. Wang, A. M. Romanic, G.-l. Liu, C. Louden, J.-L. Gu, S. Kumar, G. Poste, R. R. Ruffolo Jr, and G. Z. Feuerstein, *Circ. Res.*, 82, 166(1998)).

As having such JNK inhibitory activity, oxyindole derivatives are described in WO00/64872 and uracyl derivatives are described in WO00/75118.

On the other hand, as pyridyl-azole compounds and pyrimidinyl-azole compounds, the following compounds are known.

As imidazole compounds, Japanese Patent Application under PCT laid-open under kohyo No. 7-50317 (WO93/14081) describes compounds having cytokine inhibitory activity. As oxazole derivatives, Japanese Patent Application under PCT laid-open under kohyo No. 9-505055 (WO 95/13067) describes compounds having cytokine inhibitory activity. As pyrrole derivatives, Japanese Patent Application under PCT laid-open under kohyo No. 11-510511 (WO 97/05878) describes compounds having cytokine inhibitory activity and glucagon-antagonistic activity.

As thiazole compounds, moreover, the following compounds and the like are known:
1) 1,3-thiazole derivatives represented by the formula:

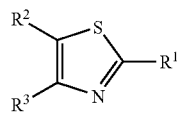

wherein $R^1$ represents a cycloalkyl group, a cyclic amino group, an amino group optionally having, as substituent(s), 1 or 2 lower alkyl, phenyl, acetyl or lower alkoxycarbonylacetyl, an alkyl group optionally having, as substituent(s), hydroxyl, carboxyl or lower alkoxycarbonyl, or a phenyl group optionally having, as substituent(s), carboxyl, 2-carboxyethenyl or 2-carboxy-1-propenyl, $R^2$ represents a pyridyl group optionally having, as substituent(s), lower alkyl, $R^3$ represents a phenyl group optionally having, as substituent(s), lower alkoxy, lower alkyl, hydroxyl, halogen or methylenedioxy, or salts thereof, which have analgesic, antipyretic, anti-inflammatory, anti-ulcerative, thromboxane $A_2$ ($TXA_2$) synthase-inhibitory, and platelet coagulation-inhibitory activities (JP-A 60-58981), 2) 1,3-thiazole derivatives represented by the formula:

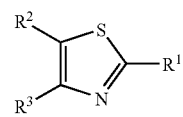

wherein $R^1$ represents an alkyl group, an alkenyl group, an aryl group, an aralkyl group, a cycloalkyl group, a heterocyclic group employing carbon as an attachment point or an amino group optionally having substituent(s), $R^2$ represents a pyridyl group optionally substituted with alkyl group(s), $R^3$ represents a phenyl group optionally having substituent(s), or salts thereof, which have analgesic, antipyretic, anti-inflammatory, anti-ulcerative, $TXA_2$ synthase-inhibitory, and platelet coagulation-inhibitory activities (JP-A 61-10580), 3) 1,3-thiazole derivatives represented by the formula:

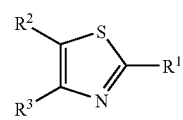

wherein $R^1$ represents an alkyl group, an alkenyl group, an aryl group, an aralkyl group, a cycloalkyl group, a heterocyclic group employing carbon as an attachment point or an amino group optionally having substituent(s), $R^2$ represents a pyridyl group optionally substituted with alkyl group(s), $R^3$ represents an aryl group optionally having substituent(s), or salts thereof, which have analgesic, antipyretic, anti-inflammatory, anti-ulcerative, $TXA_2$ synthase-inhibitory, and platelet coagulation-inhibitory activities (U.S. Pat. No. 4,612,321), 4) a compound represented by the formula:

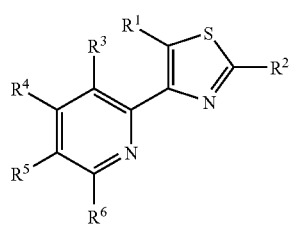

wherein $R^1$ represents an optionally substituted phenyl, $R^2$ represents $C_{1-6}$ alkyl or $(CH_2)_n Ar$, n represents 0–2, Ar represents an optionally substituted phenyl, $R^3$ represents a hydrogen or $C_{1-4}$ alkyl, $R^4$ represents a hydrogen, $C_{1-4}$ alkyl and the like, $R^5$ represents a hydrogen or $C_{1-4}$ alkyl, $R^6$ represents a hydrogen, $C_{1-4}$ alkyl and the like, or a salt thereof, having an inhibitory activity of gastric acid secretion (JP-T 7-503023, WO93/15071)

5) a compound represented by the formula:

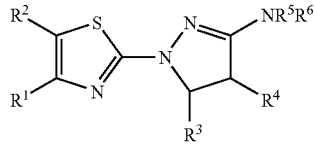

wherein $R^1$ represents pyridyl and the like, $R^2$ represents phenyl and the like, $R^3$ and $R^4$ represent a hydrogen or methyl, $R^5$ represents methyl and the like, and $R^6$ represents a hydrogen, methyl and the like, or a salt thereof, which is an antiinflammatory agent and antiallergic agent (DE-A-3601411), 6) a compound represented by the formula:

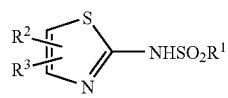

wherein $R_1$ represents a lower alkyl substituted by halogen, $R^2$ represents pyridyl and the like, and $R^3$ represents phenyl and the like, or a salt thereof, having an antiinflammatory, antipyretic, analgesic and antiallergic activity (JP-A-570446), and 7) a thiazole compound represented by the formula:

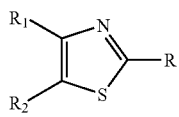

wherein R represents a lower alkyl group; a lower haloalkyl group; a lower hydroxyalkyl group; a lower alkoxy(lower)alkyl group; an aralkyloxy(lower)alkyl group and the like, $R^1$ represents a cycloalkyl group optionally substituted by lower alkyl group(s) and the like, and $R^2$ represents an optionally substituted aryl group and the like, or a pharmaceutically acceptable salt thereof, having a selective inhibitory activity of TNF-α production and/or IFN-γ production (JP-A-11-49762).

8) as a compound having adenosine $A_3$ receptor antagonistic action, p38 MAP kinase inhibitory action and TNF-α production inhibitory action, an optionally N-oxidized compound represented by the formula:

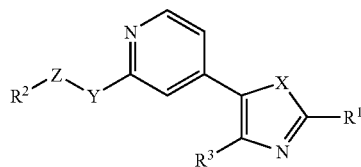

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof, (WO00/64894).

9) a compound represented by the formula:

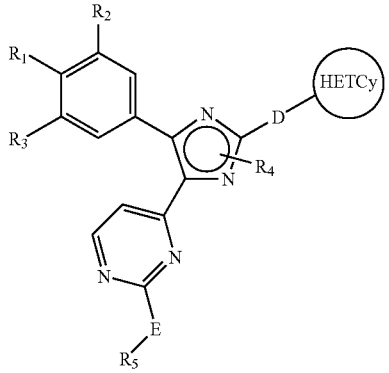

wherein $R_1$ is —F, —Cl, —Br, —OH, —SH, —$NH_2$ or —$CH_3$;

$R_2$ is —F, —Cl, —Br, —OH, —SH, —$NH_2$ or —$CH_3$;

$R_3$ is —H, —F, —Cl, —Br, —OH, —SH, —$NH_2$, —$CH_3$, —$OCH_3$ or —$CH_2CH_3$;

$R^4$ is —$C_{1-4}$ alkyl (e.g. methyl, ethyl, propyl, isopropyl, butyl, sec-butyl, tert-butyl etc.) optionally substituted by a —$C_{3-7}$ cycloalkyl (e.g. cyclopropyl, cyclobutyl, cyclopentyl, cyclohexyl etc.) (specific examples include propyl, cyclopropylmethyl and the like);

$R_5$ is —$C_{1-4}$ alkyl (e.g. methyl, ethyl, propyl, isopropyl, butyl, sec-butyl, tert-butyl etc.) or —$C_{3-7}$ cycloalkyl (e.g. cyclopropyl, cyclobutyl, cyclopentyl, cyclohexyl etc.) (specific examples include ethyl, cyclopropyl, cyclohexyl and the like), wherein the —$C_{1-4}$ alkyl is optionally substituted by a phenyl;

D is a bond or an alkyl bridge having 1–3 carbon atoms;

E is —NH— or —$NH_2^+$—; and

HETCy is a 4- to 10-membered non-aromatic heterocyclic group containing at least one N atom and optionally containing one or two additional N atoms and 0 or one O or S atom (e.g., pyrrolidinyl, piperidinyl group and the like, particularly preferably 4-piperidinyl group), and optionally substituted by —$C_{1-4}$ alkyl (e.g. methyl, ethyl, propyl, isopropyl, butyl, sec-butyl, tert-butyl etc.) or —C(O)—O—$CH_2$ phenyl (specific examples include 4-piperidinyl group, N-methyl-4-piperidinyl group, N-benzyloxycarbonyl-4-piperidinyl group) or a pharmaceutically acceptable salt thereof (WO01/91749).

All the above-mentioned references are quoted in the present specification as references.

As mentioned above, JNK shows various physiological activities by c-Jun phosphorylation, and the development of a JNK inhibitor is desired, which is more satisfactory in terms of effect, prolonged action, safety and the like as a prophylactic or therapeutic drug of various diseases (e.g., rheumatoid arthritis, cardiac ischemia, brain ischemia and the like) due to the excessive activation of c-Jun.

DISCLOSURE OF THE INVENTION

It is an object of the present invention to provide a more satisfactory JNK inhibitor in terms of effect, prolonged action, safety and the like as a prophylactic or therapeutic drug of various diseases (e.g., rheumatoid arthritis, cardiac ischemia, brain ischemia and the like) due to the excessive activation of c-Jun.

The present inventors have conducted various studies and first found that an azole compound having chemical structural specificity in the substitution on a particular position of its azole backbone by a nitrogen-containing aromatic group having substituent(s) (except compounds described in the above-mentioned reference (WO01/91749)) (hereinafter sometimes to be abbreviated as Compound (I)) unexpectedly has superior JNK inhibitory action and the like based on said specific chemical structure, and an agent containing this has superior properties as pharmaceutical products such as stability and the like and is sufficiently satisfactory as a pharmaceutical agent, and based on these findings, completed the present invention.

Accordingly, the present invention relates to the following [1] to [41].

[1] A c-Jun N-terminal kinase inhibitor comprising an azole compound (I) substituted by a nitrogen-containing aromatic group having substituent(s), except a compound represented by the formula:

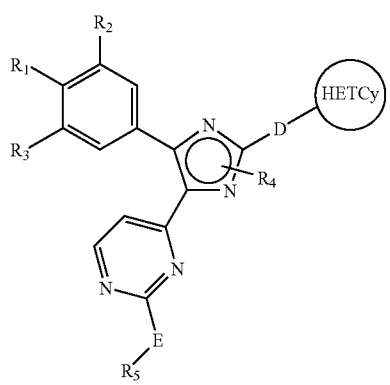

(A)

wherein
$R_1$ is —F, —Cl, —Br, —OH, —SH, —NH$_2$ or —CH$_3$;
$R_2$ is —F, —Cl, —Br, —OH, —SH, —NH$_2$ or —CH$_3$;
$R_3$ is —H, —F, —Cl, —Br, —OH, —SH, —NH$_2$, —CH$_3$, —OCH$_3$ or —CH$_2$CH$_3$;
$R_4$ is —$C_{1-4}$ alkyl optionally substituted by a —$C_{3-7}$ cycloalkyl;
$R_5$ is —$C_{1-4}$ alkyl or —$C_{3-7}$ cycloalkyl, wherein said —$C_{1-4}$ alkyl is optionally substituted by a phenyl;
D is a bond or an alkyl bridge having 1–3 carbon atoms;
E is —NH— or —NH$_2$$^+$—; and
HETCy is a 4- to 10-membered non-aromatic heterocyclic group containing at least one N atom and optionally containing one or two additional N atoms and 0 or one O or S atom, and optionally substituted by —$C_{1-4}$ alkyl or —C(O)—O—CH$_2$ phenyl, or a salt thereof or a prodrug thereof.

[2] The inhibitor of the above-mentioned [1], wherein the nitrogen-containing aromatic group is a 4-pyridyl group or a 4-pyrimidinyl group.

[3] The inhibitor of the above-mentioned [1], wherein the azole compound (I) is an optionally N-oxidized compound represented by the formula:

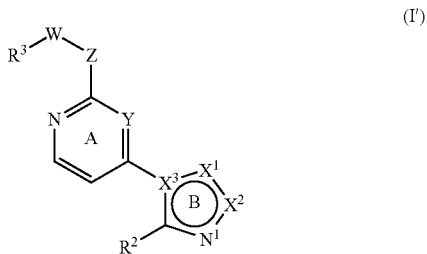

(I')

wherein
$N^1$ is a nitrogen atom optionally having a substituent or a hydrogen atom,
$X^1$ is (i) a carbon atom optionally having substituent(s) or hydrogen atom(s), (ii) an oxygen atom, (iii) a sulfur atom or (iv) a nitrogen atom optionally having a substituent or a hydrogen atom,
$X^2$ is (i) a carbon atom optionally having substituent(s) or hydrogen atom(s), (ii) an oxygen atom, (iii) a sulfur atom or (iv) a nitrogen atom optionally having a substituent or a hydrogen atom,
$X^3$ is (i) a carbon atom or (ii) a nitrogen atom, wherein
  (1) when $X^1$ is an oxygen atom or a sulfur atom, $X^2$ is a carbon atom optionally having substituent(s) or hydrogen atom(s), $X^3$ is a carbon atom and $N^1$ is a nitrogen atom,
  (2) when $X^1$ is a nitrogen atom having a substituent or a hydrogen atom and $X^3$ is a carbon atom, $X^2$ is a carbon atom optionally having substituent(s) or hydrogen atom(s) and $N^1$ is a nitrogen atom,
  (3) when $X^1$ and $X^3$ are each a nitrogen atom, $X^2$ is a carbon atom optionally having substituent(s) or hydrogen atom(s), and $N^1$ is a nitrogen atom,
  (4) when $X^1$ is a carbon atom optionally having substituent(s) or hydrogen atom(s) and $X^2$ is an oxygen atom or a sulfur atom, $X^3$ is a carbon atom and $N^1$ is a nitrogen atom,
  (5) when $X^1$ is a carbon atom optionally having substituent(s) or hydrogen atom(s) and $X^3$ is a carbon atom, one of $N^1$ and $X^2$ is a nitrogen atom, and the other is a nitrogen atom having a substituent or a hydrogen atom,
  (6) when $X^1$ and $X^2$ are each a carbon atom optionally having substituent(s) or hydrogen atom(s) and $X^3$ is a carbon atom, $N^1$ is a nitrogen atom having a substituent or a hydrogen atom, and
  (7) when $X^1$ and $X^2$ are each a carbon atom optionally having substituent(s) or hydrogen atom(s) and $X^3$ is a nitrogen atom, $N_1$ is a nitrogen atom,
ring A optionally further has substituent(s),
ring B is an aromatic ring,
Y is (i) a carbon atom optionally having substituent(s) or hydrogen atom(s) or (ii) a nitrogen atom,
Z is a bond, —NR$^4$— (R$^4$ is a hydrogen atom or a hydrocarbon group optionally having substituent(s)), an oxygen atom or an optionally oxidized sulfur atom,
W is a bond or a divalent hydrocarbon group optionally having substituent(s), R² is an aromatic group optionally having substituent(s), and
R³ is a hydrocarbon group optionally having substituent(s) or a heterocyclic group optionally having substituent(s).

[4] The inhibitor of the above-mentioned [3], wherein the compound (I') is an optionally N-oxidized compound represented by the formula:

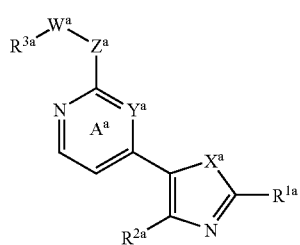

(Ia)

wherein
$X^a$ is (i) an oxygen atom, (ii) a sulfur atom or (iii) a nitrogen atom optionally having a substituent or a hydrogen atom,
ring $A^a$ optionally further has substituent(s),
$Y^a$ is (i) a carbon atom optionally having substituent(s) or hydrogen atom(s) or (ii) a nitrogen atom,
$Z^a$ is a bond, $-NR^{4a}-$ ($R^{4a}$ is a hydrogen atom or a hydrocarbon group optionally having substituent(s)), an oxygen atom or an optionally oxidized sulfur atom,
$W^a$ is a bond or a divalent hydrocarbon group optionally having substituent(s),
$R^{1a}$ is a hydrogen atom, a hydrocarbon group optionally having substituent(s), a heterocyclic group optionally having substituent(s), an amino group optionally having substituent(s) or an acyl group, and
$R^{2a}$ is an aromatic group optionally having substituent(s),
$R^{3a}$ is a hydrocarbon group optionally having substituent(s) or a heterocyclic group optionally having substituent(s).

[5] The inhibitor of the above-mentioned [3], wherein the compound (I') is an optionally N-oxidized compound represented by the formula:

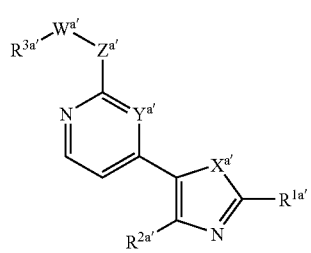

(Ia')

wherein
$X^{a'}$ is (i) an oxygen atom or (ii) a sulfur atom,
$Y^{a'}$ is a carbon atom or a nitrogen atom,
$Z^{a'}$ is a bond, $-NR^{4a'}-$ ($R^{4a'}$ is a hydrogen atom or a hydrocarbon group optionally having substituent(s)), an oxygen atom or an optionally oxidized sulfur atom,
$W^{a'}$ is a bond or a divalent hydrocarbon group optionally having substituent(s),
$R_{1a'}$ is a hydrogen atom, a hydrocarbon group optionally having substituent(s), a heterocyclic group optionally having substituent(s), an amino group optionally having substituent(s) or an acyl group, $R^{2a'}$ is an aromatic group optionally having substituent(s), and
$R^{3a'}$ is a hydrocarbon group optionally having substituent(s) or a heterocyclic group optionally having substituent(s).

[6] The inhibitor of the above-mentioned [3], wherein the compound (I') is an optionally N-oxidized compound represented by the formula:

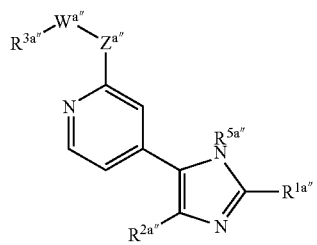

(Ia'')

wherein
$Z^{a''}$ is a bond, $-NR^{4a''}-$ ($R^{4a''}$ is a hydrogen atom or a hydrocarbon group optionally having substituent(s)), an oxygen atom or an optionally oxidized sulfur atom,
$W^{a''}$ is a bond or a divalent hydrocarbon group optionally having substituent(s),
$R^{1a''}$ is a hydrogen atom, a hydrocarbon group optionally having substituent(s), a heterocyclic group optionally having substituent(s), an amino group optionally having substituent(s) or an acyl group,
$R^{2a''}$ is an aromatic group optionally having substituent(s),
$R^{3a''}$ is a hydrocarbon group optionally having substituent(s) or a heterocyclic group optionally having substituent(s), and
$R^{5a''}$ is a hydrogen atom, a hydrocarbon group optionally having substituent(s) or a heterocyclic group optionally having substituent(s).

[7] The inhibitor of the above-mentioned [3], wherein the compound (I') is an optionally N-oxidized compound represented by the formula:

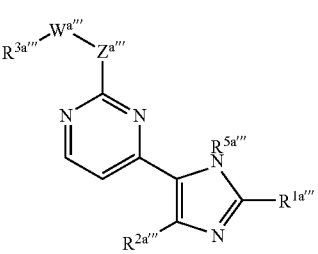

(Ia''')

wherein
$Z^{a'''}$ is a bond, $-NR^{4a'''}-$ ($R^{4a'''}$ is a hydrogen atom or a hydrocarbon group optionally having substituent(s)), an oxygen atom or an optionally oxidized sulfur atom,
$W^{a'''}$ is a bond or a divalent hydrocarbon group optionally having substituent(s),
$R^{1a'''}$ is a hydrogen atom, a hydrocarbon group optionally having substituent(s) other than a non-aromatic heterocyclic group, an aromatic heterocyclic group optionally having substituent(s), an amino group optionally having substituent(s) or an acyl group,
$R^{2a'''}$ is an aromatic group optionally having substituent(s), $R^{3a'''}$ is a hydrocarbon group optionally having substituent(s) or a heterocyclic group optionally having substituent(s), and $R^{5a'''}$ is a hydrogen atom, a hydrocarbon group optionally having substituent(s) or a heterocyclic group optionally having substituent(s)

[8] The inhibitor of the above-mentioned [3], wherein the compound (I') is an optionally N-oxidized compound represented by the formula:

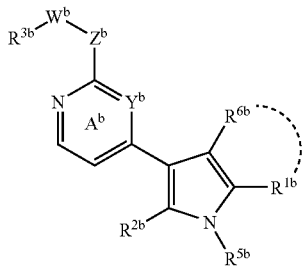

(Ib)

wherein
ring $A^b$ optionally further has substituent(s),
$Y^b$ is (i) a carbon atom optionally having substituent(s) or hydrogen atom(s) or (ii) a nitrogen atom,
$Z^b$ is a bond, —$NR^{4b}$— ($R^{4b}$ is a hydrogen atom or a hydrocarbon group optionally having substituent(s)), an oxygen atom or an optionally oxidized sulfur atom,
$W^b$ is a bond or a divalent hydrocarbon group optionally having substituent(s),
$R^{1b}$ is a hydrogen atom, a hydrocarbon group optionally having substituent(s), a heterocyclic group optionally having substituent(s), an amino group optionally having substituent(s) or an acyl group,
$R^{2b}$ is an aromatic group optionally having substituent(s),
$R^{3b}$ is a hydrocarbon group optionally having substituent(s) or a heterocyclic group optionally having substituent(s),
$R^{5b}$ is a hydrogen atom, a hydrocarbon group optionally having substituent(s) or a heterocyclic group optionally having substituent(s),
$R^{6b}$ is a hydrogen atom, a hydrocarbon group optionally having substituent(s), a heterocyclic group optionally having substituent(s), an amino group optionally having substituent(s) or an acyl group, and
$R^{1b}$ and $R^{6b}$ are optionally linked to form a ring.

[9] The inhibitor of the above-mentioned [3], wherein the compound (I') is an optionally N-oxidized compound represented by the formula:

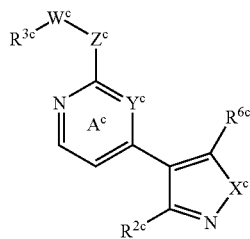

(Ic)

wherein
ring $A^c$ optionally further has substituent(s),
$X^c$ is (i) an oxygen atom, (ii) a sulfur atom or (iii) a nitrogen atom optionally having a substituent or a hydrogen atom,
$Y^c$ is (i) a carbon atom optionally having substituent(s) or hydrogen atom(s) or (ii) a nitrogen atom, $Z^c$ is a bond, —$NR^{4c}$— ($R^{4c}$ is a hydrogen atom or a hydrocarbon group optionally having substituent(s)), an oxygen atom or an optionally oxidized sulfur atom,
$W^c$ is a bond or a divalent hydrocarbon group optionally having substituent(s),
$R^{2c}$ is an aromatic group optionally having substituent(s),
$R^{3c}$ is a hydrocarbon group optionally having substituent(s) or a heterocyclic group optionally having substituent(s), and
$R^{6c}$ is a hydrogen atom, a hydrocarbon group optionally having substituent(s), a heterocyclic group optionally having substituent(s), an amino group optionally having substituent(s) or an acyl group.

[10] The inhibitor of the above-mentioned [3], wherein the compound (I') is an optionally N-oxidized compound represented by the formula:

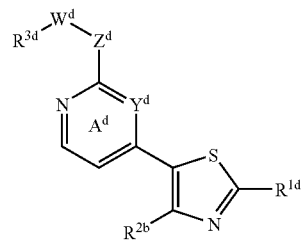

(Id)

wherein
ring $A^d$ optionally further has substituent(s),
$Y^d$ is (i) a carbon atom optionally having substituent(s) or hydrogen atom(s) or (ii) a nitrogen atom,
$Z^d$ is a bond, —$NR^{4d}$— ($R^{4d}$ is a hydrogen atom or a hydrocarbon group optionally having substituent(s)), an oxygen atom or an optionally oxidized sulfur atom,
$W^d$ is a bond or a divalent hydrocarbon group optionally having substituent(s),
$R^{1d}$ is a hydrogen atom, a hydrocarbon group optionally having substituent(s), a heterocyclic group optionally having substituent(s), an amino group optionally having substituent(s) or an acyl group,
$R^{2d}$ is an aromatic group optionally having substituent(s), and
$R^{3d}$ is a hydrocarbon group optionally having substituent(s) or a heterocyclic group optionally having substituent(s).

[11] The inhibitor of the above-mentioned [3], wherein the compound (I') is an optionally N-oxidized compound represented by the formula:

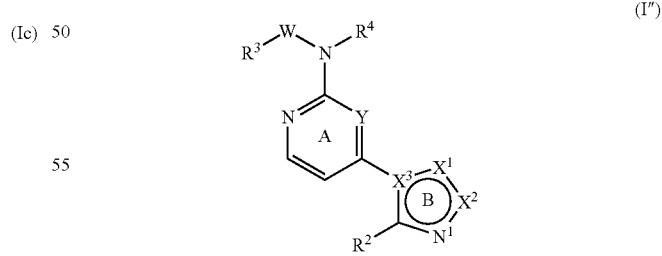

(I'')

wherein
$N^1$ is a nitrogen atom optionally having a substituent or a hydrogen atom,
$X^1$ is (i) a carbon atom optionally having substituent(s) or hydrogen atom(s), (ii) an oxygen atom, (iii) a sulfur atom or (iv) a nitrogen atom optionally having a substituent or a hydrogen atom, X² is (i) a carbon atom optionally having substituent(s) or hydrogen atom(s), (ii) an oxygen atom, (iii) a sulfur atom or (iv) a nitrogen atom optionally having a substituent or a hydrogen atom, X³ is (i) a carbon atom or (ii) a nitrogen atom, wherein
(1) when X¹ is an oxygen atom or a sulfur atom, X² is a carbon atom optionally having substituent(s) or hydrogen atom(s), X³ is a carbon atom and N¹ is a nitrogen atom,
(2) when X¹ is a nitrogen atom having a substituent or a hydrogen atom and X³ is a carbon atom, X² is a carbon atom optionally having substituent(s) or hydrogen atom(s) and N¹ is nitrogen atom,
(3) when X¹ and X³ are each a nitrogen atom, X² is a carbon atom optionally having substituent(s) or hydrogen atom(s), and N¹ is a nitrogen atom,
(4) when X¹ is a carbon atom optionally having substituent(s) or hydrogen atom(s) and X² is an oxygen atom or a sulfur atom, X³ is a carbon atom and N¹ is a nitrogen atom,
(5) when X¹ is a carbon atom optionally having substituent(s) or hydrogen atom(s) and X³ is a carbon atom, one of N¹ and X² is a nitrogen atom, and the other is a nitrogen atom having a substituent or a hydrogen atom,
(6) when X¹ and X² are each a carbon atom optionally having substituent(s) or hydrogen atom(s) and X³ is a carbon atom, N¹ is a nitrogen atom having a substituent or a hydrogen atom, and
(7) when X¹ and X² are each a carbon atom optionally having substituent(s) or hydrogen atom(s) and X³ is a nitrogen atom, N¹ is a nitrogen atom, ring A optionally further has substituent(s),
ring B is an aromatic ring,
Y is (i) a carbon atom optionally having substituent(s) or hydrogen atom(s) or (ii) a nitrogen atom,
W is a bond or a divalent hydrocarbon group optionally having substituent(s),
R² is an aromatic group optionally having substituent(s),
R³ is a hydrocarbon group optionally having substituent(s) or a heterocyclic group optionally having substituent(s), and
R⁴ is a hydrogen atom or a hydrocarbon group, optionally having substituent(s).

[12] The inhibitor of the above-mentioned [11], wherein the compound (I″) is an optionally N-oxidized compound represented by the formula:

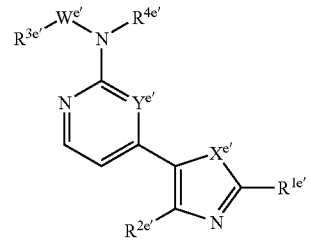

(Ie)

wherein
ring $A^e$ optionally further has substituent(s),
$X^e$ is (i) an oxygen atom, (ii) a sulfur atom or. (iii) a nitrogen atom optionally having a substituent or a hydrogen atom,
$Y^e$ is (i) a carbon atom optionally having substituent(s) or hydrogen atom(s) or (ii) a nitrogen atom,
$W^e$ is a bond or a divalent hydrocarbon group optionally having substituent(s),
$R^{1e}$ is a hydrogen atom, a hydrocarbon group optionally having substituent(s), a heterocyclic group optionally having substituent(s), an amino group optionally having substituent(s) or an acyl group,
$R^{2e}$ is an aromatic group optionally having substituent(s),
$R^{3e}$ is a hydrocarbon group optionally having substituent(s) or a heterocyclic group optionally having substituent(s), and
$R^{4e}$ is a hydrogen atom or a hydrocarbon group optionally having substituent (s)

[13] The inhibitor of the above-mentioned [11], wherein the compound (I″) is an optionally N-oxidized compound represented by the formula:

(Ie′)

wherein
$X^{e'}$ is (i) an oxygen atom or (ii) a sulfur atom,
$Y^{e'}$ is a carbon atom optionally having substituent(s) or hydrogen atom(s), or a nitrogen atom,
$W^{e'}$ is a bond or a divalent hydrocarbon group optionally having substituent(s),
$R^{1e'}$ is a hydrogen atom, a hydrocarbon group optionally having substituent(s), a heterocyclic group optionally having substituent(s), an amino group optionally having substituent(s) or an acyl group,
$R^{2e'}$ is an aromatic group optionally having substituent(s),
$R^{3e'}$ is a hydrocarbon group optionally having substituent(s) or a heterocyclic group optionally having substituent(s), and
$R^{4e'}$ is a hydrogen atom or a hydrocarbon group optionally having substituent(s).

[14] The inhibitor of the above-mentioned [11], wherein the compound (I″) is an optionally N-oxidized compound represented by the formula:

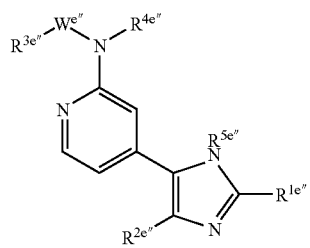

(Ie″)

wherein
$W^{e''}$ is a bond or a divalent hydrocarbon group optionally having substituent(s),
$R^{1e''}$ is a hydrogen atom, a hydrocarbon group optionally having substituent(s), a heterocyclic group optionally having substituent(s), an amino group optionally having substituent(s) or an acyl group, $R^{2e''}$ is an aromatic group optionally having substituent(s), $R^{3e''}$ is a hydrocarbon group optionally having substituent(s) or a heterocyclic group optionally having substituent(s), $R^{4e''}$ is a hydrogen atom or a hydrocarbon group optionally having substituent(s), and $R^{5e''}$ is a hydrogen atom, a hydrocarbon group optionally having substituent(s) or a heterocyclic group optionally having substituent(s).

[15] The inhibitor of the above-mentioned [11], wherein the compound (I″) is an optionally N-oxidized compound represented by the formula:

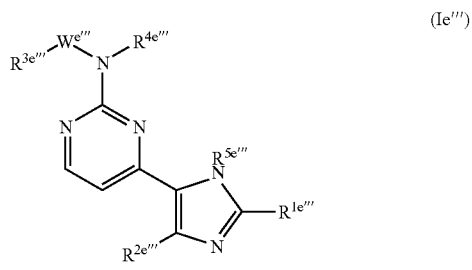

(Ie′″)

wherein $W^{e'''}$ is a bond or a divalent hydrocarbon group optionally having substituent(s), $R^{1e'''}$ is a hydrogen atom, a hydrocarbon group optionally having substituent(s) other than non-aromatic heterocyclic group, an aromatic heterocyclic group optionally having substituent(s), an amino group optionally having substituent(s) or an acyl group, $R^{2e'''}$ is an aromatic group optionally having substituent(s), $R^{3e'''}$ is a hydrocarbon group optionally having substituent(s) or a heterocyclic group optionally having substituent(s), $R^{4e'''}$ is a hydrogen atom or a hydrocarbon group optionally having substituent(s), and $R^{5e'''}$ is a hydrogen atom, a hydrocarbon group optionally having substituent(s) or a heterocyclic group optionally having substituent(s).

[16] The inhibitor of the above-mentioned [11], wherein the compound (I″) is an optionally N-oxidized compound represented by the formula:.

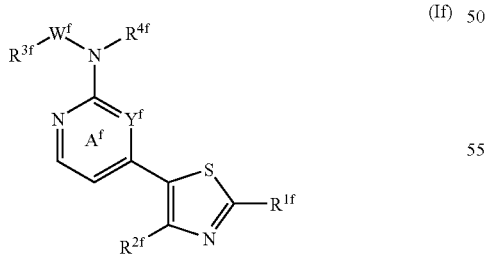

(If)

wherein ring $A^f$ optionally further has substituent(s), $Y^f$ is (i) a carbon atom optionally having substituent(s) or hydrogen atom(s), or (ii) a nitrogen atom, $W^f$ is a bond or a divalent hydrocarbon group optionally having substituent(s), $R^{1f}$ is a hydrogen atom, a hydrocarbon group optionally having substituent(s), a heterocyclic group optionally having substituent(s), an amino group optionally having substituent(s) or an acyl group, $R^{2f}$ is an aromatic group optionally having substituent(s), $R^{3f}$ is a hydrocarbon group optionally having substituent(s) or a heterocyclic group optionally having substituent(s), and $R^{4f}$ is a hydrogen atom or a hydrocarbon group optionally having substituent(s).

[17] The inhibitor of the above-mentioned [11], wherein the compound (I″) is an optionally N-oxidized compound represented by the formula:

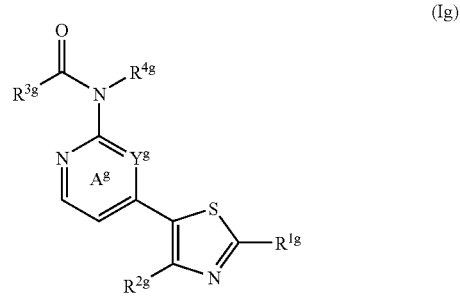

(Ig)

wherein ring $A^g$ optionally further has substituent(s), $Y^g$ is (i) a carbon atom optionally having substituent(s) or hydrogen atom(s) or (ii) a nitrogen atom, $R^{1g}$ is a hydrogen atom, a hydrocarbon group optionally having substituent(s), a heterocyclic group optionally having substituent(s), an amino group optionally having substituent(s) or an acyl group, $R^{2g}$ is an aromatic group optionally having substituent(s), $R^{3g}$ is a hydrocarbon group optionally having substituent(s) or a heterocyclic group optionally having substituent(s), and $R^{4g}$ is a hydrogen atom or a hydrocarbon group optionally having substituent(s).

[18] The inhibitor of the above-mentioned [11], wherein the compound (I″) is an optionally N-oxidized compound represented by the formula:

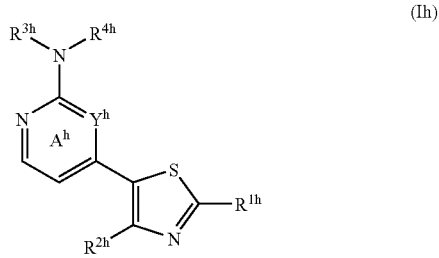

(Ih)

wherein ring Ah optionally further has substituent(s), $Y^h$ is (i) a carbon atom optionally having substituent(s) or hydrogen atom(s), or (ii) a nitrogen atom, $R^{1h}$ is a hydrogen atom, a hydrocarbon group optionally having substituent(s), a heterocyclic group optionally having substituent(s), an amino group optionally having substituent(s) or an acyl group, $R^{2h}$ is an aromatic group optionally having substituent(s), $R^{3h}$ is a hydrocarbon group optionally having substituent(s) or a heterocyclic group optionally having substituent(s), and $R^{4h}$ is a hydrogen atom or a hydrocarbon group optionally having substituent(s).

[19] The inhibitor of the above-mentioned [3], wherein the compound (I') is an optionally N-oxidized compound represented by the formula:

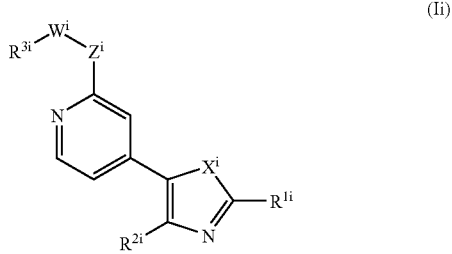

(Ii)

wherein $X^i$ is an oxygen atom or an optionally oxidized sulfur atom, $Z^i$ is a bond, —$NR^{4i}$— ($R^{4i}$ is a hydrogen atom or a hydrocarbon group optionally having substituent(s)), an oxygen atom, or an optionally oxidized sulfur atom, $W^i$ is a bond or a divalent acyclic hydrocarbon group optionally having substituent(s), $R^{1i}$ is a hydrogen atom, a hydrocarbon group optionally having substituent(s), a heterocyclic group optionally having substituent(s), an amino group optionally having substituent(s) or an acyl group, $R^{2i}$ is a pyridyl group optionally having substituent(s) or an aromatic hydrocarbon group optionally having substituent(s), and $R^{3i}$ is a hydrocarbon group optionally having substituent(s) or a heterocyclic group optionally having substituent(s).

[20] The inhibitor of the above-mentioned [3], wherein the compound (I') is an optionally N-oxidized compound represented by the formula:

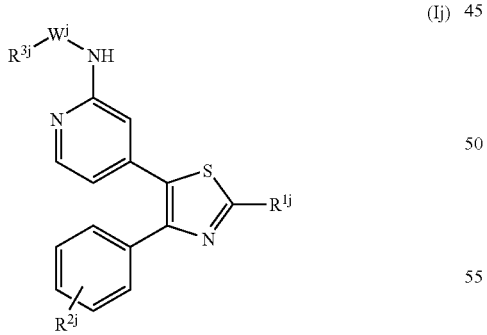

(Ij)

wherein $W^j$ is a bond, a divalent hydrocarbon group optionally having substituent(s), $R^{1j}$ is a hydrogen atom, a hydrocarbon group optionally having substituent(s), a heterocyclic group optionally having substituent(s), an amino group optionally having substituent(s) or an acyl group, $R^{2j}$ is a hydrogen atom or a substituent, and $R^{3j}$ is a hydrocarbon group optionally having substituent(s) or a heterocyclic group optionally having substituent(s).

[21] The inhibitor of the above-mentioned [3], wherein the compound (I') is an optionally N-oxidized compound represented by the formula:

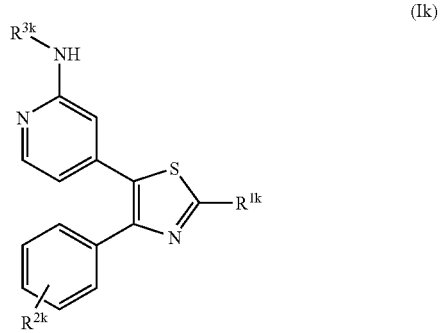

(Ik)

wherein $R^{1k}$ is a hydrogen atom, a hydrocarbon group optionally having substituent(s), a heterocyclic group optionally having substituent(s), an amino group optionally having substituent(s) or an acyl group, $R^{2k}$ is a hydrogen atom or a substituent, and $R^{3k}$ is a cyclic hydrocarbon group optionally having substituent(s) or a heterocyclic group optionally having substituent(s).

[22] The inhibitor of the above-mentioned [3], wherein the compound (I') is an optionally N-oxidized compound represented by the formula:

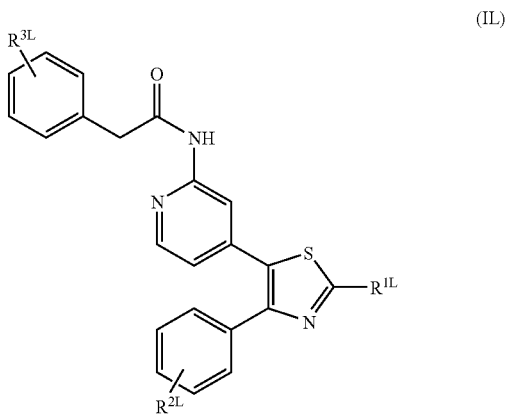

(IL)

wherein $R^{1L}$ is a hydrogen atom, a hydrocarbon group optionally having substituent(s), a heterocyclic group optionally having substituent(s), an amino group optionally having substituent(s) or an acyl group, $R^{2L}$ is a hydrogen atom or a substituent, and $R^{3L}$ is a hydrogen atom or a substituent.

[23] The inhibitor of the above-mentioned [1], which is a prophylactic or therapeutic agent of a c-Jun related disease.

[24] The inhibitor of the above-mentioned [1], which is a prophylactic or therapeutic agent of a c-Jun N-terminal kinase related disease.

[25] The inhibitor of the above-mentioned [1], which is a prophylactic or therapeutic agent of acute pancreatitis, chronic pancreatitis, adult respiratory distress syndrome, pachyderma, lupus erythematosus profundus, chronic thyroiditis, Graves' disease, autoimmune gastritis, autoimmune neutropenia, thrombocytopenia, myasthenia gravis, multiple myeloma, acute myeloblastic leukemia, chronic sarcoma, chronic myelocytic leukemia, metastatic melanoma, Kaposi's sarcoma, degenerative disease, Huntington's disease, a disease associated with ischemia/reperfusion in stroke, myocardial ischemia, ischemic cardiac disease, renal ischemia, neovascular glaucoma, infantile angioma, vascularization, hypercardia, abnormal immune response, fervescence, cellular aging or an apoptosis related disease.

[26] An optionally N-oxidized compound represented by the formula:

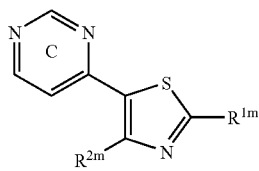

(Im)

wherein ring C is a 4-pyrimidinyl group optionally having substituent(s), $R^{1m}$ is a hydrogen atom, a hydrocarbon group optionally having substituent(s), a heterocyclic group optionally having substituent(s), an amino group optionally having substituent(s) or an acyl group, and $R^{2m}$ is an aromatic group optionally having substituent(s), or a salt thereof.

[27] The compound of the above-mentioned [26], wherein the compound (Im) is an optionally N-oxidized compound represented by the formula:

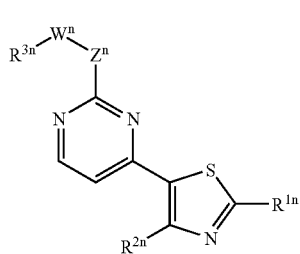

(In)

wherein $Z^n$ is a bond, —$NR^{4n}$— ($R^{4n}$ is a hydrogen atom or a hydrocarbon group optionally having substituent(s)), an oxygen atom or an optionally oxidized sulfur atom, $W^n$ is a bond or a divalent hydrocarbon group optionally having substituent(s), $R^{1n}$ is a hydrogen atom, a hydrocarbon group optionally having substituent(s), a heterocyclic group optionally having substituent(s), an amino group optionally having substituent(s) or an acyl group, $R^{2n}$ is an aromatic group optionally having substituent(s), and $R^{3n}$ is a hydrogen atom, a hydrocarbon group optionally having substituent(s) or a heterocyclic group optionally having substituent(s).

[28] The compound of the above-mentioned [27], wherein both $W^n$ and $Z^n$ are each a bond.

[29] The compound of the above-mentioned [26], wherein the compound (Im) is an optionally N-oxidized compound represented by the formula:

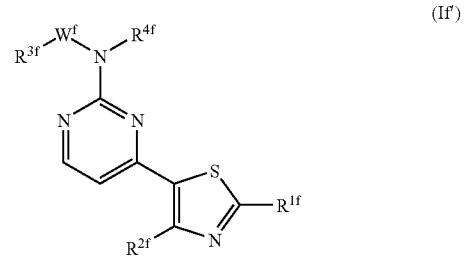

(If')

wherein $W^f$ is a bond or a divalent hydrocarbon group optionally having substituent(s), $R^{1f}$ is a hydrogen atom, a hydrocarbon group optionally having substituent(s), a heterocyclic group optionally having substituent(s), an amino group optionally having substituent(s) or an acyl group, $R^{2f}$ is an aromatic group optionally having substituent(s), $R^{3f}$ is a hydrocarbon group optionally having substituent(s) or a heterocyclic group optionally having substituent(s), and $R^{4f}$ is a hydrogen atom or a hydrocarbon group optionally having substituent(s).

[30] The compound of the above-mentioned [29], wherein the compound (If') is an optionally N-oxidized compound represented by the formula:

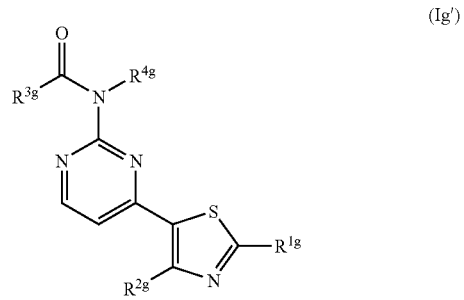

(Ig')

wherein $R^{1g}$ is a hydrogen atom, a hydrocarbon group optionally having substituent(s), a heterocyclic group optionally having substituent(s), an amino group optionally having substituent(s) or an acyl group, $R^{2g}$ is an aromatic group optionally having substituent(s), $R^{3g}$ is a hydrocarbon group optionally having substituent(s) or a heterocyclic group optionally having substituent(s), and $R^{4g}$ is a hydrogen atom or a hydrocarbon group optionally having substituent(s).

[31] The compound of the above-mentioned [29], wherein the compound (Ih') is an optionally N-oxidized compound represented by the formula:

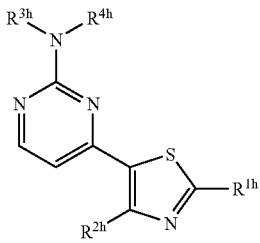

(Ih')

wherein

R$^{1h}$ is a hydrogen atom, a hydrocarbon group optionally having substituent(s), a heterocyclic group optionally having substituent(s), an amino group optionally having substituent(s) or an acyl group, R$^{2h}$ is an aromatic group optionally having substituent(s), R$^{3h}$ is a hydrocarbon group optionally having substituent(s) or a heterocyclic group optionally having substituent(s), and R$^{4h}$ is a hydrogen atom or a hydrocarbon group optionally having substituent(s)

[32] A production method of an optionally N-oxidized compound represented by the formula:

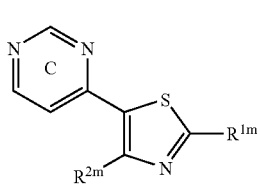

(Im)

wherein ring C is a 4-pyrimidinyl group optionally having substituent(s),

R$^{1m}$ is a hydrogen atom, a hydrocarbon group optionally having substituent(s), a heterocyclic group optionally having substituent(s), an amino group optionally having substituent(s) or an acyl group, and R$^{2m}$ is an aromatic group optionally having substituent(s), or a salt thereof, which comprises reacting a compound represented by the formula:

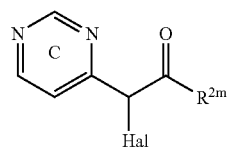

wherein ring C and R$^{2m}$ are as defined above and Hal is a halogen, or a salt thereof, with a compound represented by the formula: R$^{1m}$CSNH$_2$ wherein R$^{1m}$ is as defined above, or a salt thereof.

[33] A prodrug of the compound of the above-mentioned [26].

[34] A pharmaceutical agent containing a compound of the above-mentioned [26] or a prodrug thereof.

[35] A method of inhibiting c-Jun N-terminal kinase, which comprises administering an effective amount of an azole compound (I) substituted by a nitrogen-containing aromatic group having substituent(s) or a salt thereof or a prodrug thereof to a mammal.

[36] A method for the prophylaxis or treatment of acute pancreatitis, chronic pancreatitis, adult respiratory distress syndrome, pachyderma, lupus erythematosus profundus, chronic thyroiditis, Graves' disease, autoimmune gastritis, autoimmune neutropenia, thrombocytopenia, myasthenia gravis, multiple myeloma, acute myeloblastic leukemia, chronic sarcoma, chronic myelocytic leukemia, metastatic melanoma, Kaposi's sarcoma, degenerative disease, Huntington's disease, a disease associated with ischemia/reperfusion in stroke, myocardial ischemia, ischemic cardiac disease, renal ischemia, neovascular glaucoma, infantile angioma, vascularization, hypercardia, abnormal immune response, fervescence, cellular aging or an apoptosis related disease, which comprises administering an effective amount of an azole compound (I) substituted by a nitrogen-containing aromatic group having substituent(s) or a salt thereof or a prodrug thereof to a mammal.

[37] Use of an azole compound (I) substituted by a nitrogen-containing aromatic group having substituent(s) or a salt thereof or a prodrug thereof for the production of a c-Jun N-terminal kinase inhibitor.

[38] Use of an azole compound (I) substituted by a nitrogen-containing aromatic group having substituent(s) or a salt thereof or a prodrug thereof for the production of a prophylactic or therapeutic agent of acute pancreatitis, chronic pancreatitis, adult respiratory distress syndrome, pachyderma, lupus erythematosus profundus, chronic thyroiditis, Graves' disease, autoimmune gastritis, autoimmune neutropenia, thrombocytopenia, myasthenia gravis, multiple myeloma, acute myeloblastic leukemia, chronic sarcoma, chronic myelocytic leukemia, metastatic melanoma, Kaposi's sarcoma, degenerative disease, Huntington's disease, a disease associated with ischemia/reperfusion in stroke, myocardial ischemia, ischemic cardiac disease, renal ischemia, neovascular glaucoma, infantile angioma, vascularization, hypercardia, abnormal immune response, fervescence, cellular aging or an apoptosis related disease.

[39] A pharmaceutical agent comprising a combination of an azole compound (I) substituted by a nitrogen-containing aromatic group having substituent(s) or a salt thereof or a prodrug thereof and one or more kinds of drugs selected from (i) a non-steroidal antiinflammatory drug, (ii) a disease-modifying anti-rheumatic drug, (iii) an anti-cytokine drug, (iv) an immunomodulator, (v) a steroid, (vi) a p38 MAP kinase inhibitor and (vii) a TNF-α production inhibitor.

[40] A pharmaceutical agent of the above-mentioned [39], which is a prophylactic or therapeutic agent of acute pancreatitis, chronic pancreatitis, adult respiratory distress syndrome, pachyderma, lupus erythematosus profundus, chronic thyroiditis, Graves' disease, autoimmune gastritis, autoimmune neutropenia, thrombocytopenia, myasthenia gravis, multiple myeloma, acute myeloblastic leukemia, chronic sarcoma, chronic myelocytic leukemia, metastatic melanoma, Kaposi's sarcoma, degenerative disease, Huntington's disease, a disease associated with ischemia/reperfusion in stroke, myocardial ischemia, ischemic cardiac disease, renal ischemia, neovascular glaucoma, infantile angioma, vascularization, hypercardia, abnormal immune response, fervescence, cellular aging or an apoptosis related disease.

[41] A method for the prophylaxis or treatment of acute pancreatitis, chronic pancreatitis, adult respiratory distress syndrome, pachyderma, lupus erythematosus profundus, chronic thyroiditis, Graves' disease, autoimmune gastritis, autoimmune neutropenia, thrombocytopenia, myasthenia gravis, multiple myeloma, acute myeloblastic leukemia, chronic sarcoma, chronic myelocytic leukemia, metastatic melanoma, Kaposi's sarcoma, degenerative disease, Huntington's disease, a disease associated with ischemia/reperfusion in stroke, myocardial ischemia, ischemic cardiac disease, renal ischemia, neovascular glaucoma, infantile angioma, vascularization, hypercardia, abnormal immune response, fervescence, cellular aging or an apoptosis related disease, which comprises administering, to a mammal, an effective amount of an azole compound (I) substituted by a nitrogen-containing aromatic group having substituent(s) or a salt thereof or a prodrug thereof concurrently with an effective amount of one or more kinds of drugs selected from (i) a nonsteroidal antiinflammatory drug, (ii) a disease-modifying anti-rheumatic drug, (iii) an anti-cytokine drug, (iv) an immunomodulator, (v) a steroid, (vi) a p38 MAP kinase inhibitor and (vii) a TNF-α production inhibitor.

In the present invention, as the "substituent" that "ring A", "ring $A^a$", "ring $A^b$", "ring $A^c$", "ring $A^d$", "ring $A^e$", "ring $A^f$", "ring $A^g$" and "ring $A^h$" may further have, for example, halogen atoms (e.g., fluorine, chlorine, bromine, iodine etc.), $C_{1-3}$ alkylenedioxy (e.g., methylenedioxy, ethylenedioxy etc.), nitro, cyano, optionally halogenated $C_{1-6}$ alkyl, optionally halogenated $C_{2-6}$ alkenyl, carboxy $C_{2-6}$ alkenyl (e.g., 2-carboxyethenyl, 2-carboxy-2-methylethenyl etc.), optionally halogenated $C_{2-6}$ alkynyl, optionally halogenated $C_{3-8}$ cycloalkyl, $C_{6-14}$ aryl (e.g., phenyl, 1-naphthyl, 2-naphthyl, 2-biphenylyl, 3-biphenylyl, 4-biphenylyl, 2-anthryl etc.), optionally halogenated $C_{1-8}$ alkoxy, $C_{1-6}$ alkoxy-carbonyl-$C_{1-6}$ alkoxy (e.g., ethoxycarbonylmethyloxy etc.), hydroxy, $C_{6-14}$ aryloxy (e.g., phenyloxy, 1-naphthyloxy, 2-naphthyloxy etc.), $C_{7-16}$ aralkyloxy (e.g., benzyloxy, phenethyloxy etc.), mercapto, optionally halogenated $C_{1-6}$ alkylthio, $C_{6-14}$ arylthio (e.g., phenylthio, 1-naphthylthio, 2-naphthylthio etc.), $C_{7-16}$ aralkylthio (e.g., benzylthio, phenethylthio etc.), amino, mono-$C_{1-6}$ alkylamino (e.g., methylamino, ethylamino etc.), mono-$C_{6-14}$ arylamino (e.g., phenylamino, 1-naphthylamino, 2-naphthylamino etc.), di-$C_{1-6}$ alkylamino (e.g., dimethylamino, diethylamino, ethylmethylamino etc.), $C_{3-8}$ cycloalkylamino (e.g., cyclopentylamino, cyclohexylamino etc.), di-$C_{6-14}$ arylamino (e.g., diphenylamino etc.), formyl, carboxy, carboxy-$C_{1-6}$ alkyl (e.g., carboxymethyl, carboxyethyl etc.), $C_{1-6}$ alkyl-carbonyl (e.g., acetyl, propionyl, pivaloyl etc.), $C_{3-8}$ cycloalkylcarbonyl (e.g., cyclopropylcarbonyl, cyclopentylcarbonyl, cyclohexylcarbonyl etc.), $C_{1-6}$ alkoxy-carbonyl (e.g., methoxycarbonyl, ethoxycarbonyl, propoxycarbonyl, tert-butoxycarbonyl etc.), $C_{6-14}$ arylcarbonyl (e.g., benzoyl, 1-naphthoyl, 2-naphthoyl etc.), $C_{7-16}$ aralkyl-carbonyl (e.g., phenylacetyl, 3-phenylpropionyl etc.), $C_{6-14}$ aryloxy-carbonyl (e.g., phenoxycarbonyl etc.), $C_{7-16}$ aralkyloxy-carbonyl (e.g., benzyloxycarbonyl, phenethyloxycarbonyl etc.), 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.), carbamoyl, thiocarbamoyl, mono-$C_{1-6}$ alkylcarbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), mono- or di-$C_{6-14}$ aryl-carbamoyl (e.g., phenylcarbamoyl, 1-naphthylcarbamoyl, 2-naphthylcarbamoyl etc.), mono- or di-5- or 6-membered heterocyclic carbamoyl (e.g., 2-pyridylcarbamoyl, 325 pyridylcarbamoyl, 4-pyridylcarbamoyl, 2-thienylcarbamoyl, 3-thienylcarbamoyl etc.), $C_{1-6}$ alkylsulfonyl (e.g., methylsulfonyl, ethylsulfonyl etc.), $C_{1-6}$ alkylsulfinyl (e.g., methylsulfinyl, ethylsulfinyl etc.), $C_{6-14}$ arylsulfonyl (e.g., phenylsulfonyl, 1-naphthylsulfonyl, 2-naphthylsulfonyl etc.), $C_{6-14}$ arylsulfinyl (e.g., phenylsulfinyl, 1-naphthylsulfinyl, 2-naphthylsulfinyl etc.), formylamino, $C_{1-6}$ alkyl-carbonylamino (e.g., acetylamino, propionylamino, pivaloylamino etc.), $C_{3-8}$ cycloalkyl-carbonylamino (e.g., cyclopentylcarbonylamino, cyclohexylcarbonylamino etc.), $C_{6-14}$ aryl-carbonylamino (e.g., benzoylamino, naphthoylamino etc.), $C_{1-6}$ alkoxy-carbonylamino (e.g., methoxycarbonylamino, ethoxycarbonylamino, propoxycarbonylamino, butoxycarbonylamino etc.), $C_{1-6}$ alkylsulfonylamino (e.g., methylsulfonylamino, ethylsulfonylamino etc.), $C_{6-14}$ arylsulfonylamino (e.g., phenylsulfonylamino, 2-naphthylsulfonylamino, 1-naphthylsulfonylamino etc.), $C_{1-6}$ alkyl-carbonyloxy (e.g., acetoxy, propionyloxy etc.), $C_{6-14}$ aryl-carbonyloxy (e.g., benzoyloxy, naphthylcarbonyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkylcarbamoyloxy (e.g., methylcarbamoyloxy, ethylcarbamoyloxy etc.), di-$C_{1-6}$ alkyl-carbamoyloxy (e.g., dimethylcarbamoyloxy, diethylcarbamoyloxy etc.), mono- or di-$C_{6-14}$ aryl-carbamoyloxy (e.g., phenylcarbamoyloxy, naphthylcarbamoyloxy etc.), nicotinoyloxy, isonicotinoyloxy, 5- to 7-membered saturated cyclic amino optionally having substituents, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3 isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), sulfo, sulfamoyl, sulfinamoyl, sulfenamoyl, a group wherein two or more (e.g., 2–3) of these substituents are bonded, and the like can be mentioned.

As the aforementioned "optionally halogenated $C_{1-6}$ alkyl", for example, $C_{1-6}$ alkyl (e.g., methyl, ethyl, propyl, isopropyl, butyl, isobutyl, sec-butyl, tert-butyl, pentyl, hexyl etc.) and the like optionally having 1 to 5, preferably 1 to 3, halogen atoms (e.g., fluorine, chlorine, bromine, iodine etc.) can be mentioned. As specific examples, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like can be mentioned.

As the aforementioned "optionally halogenated $C_{2-6}$ alkenyl", for example, $C_{2-6}$ alkenyl (e.g., vinyl, propenyl, isopropenyl, 2-buten-1-yl, 4-penten-1-yl, 5-hexen-1-yl etc.) optionally having 1 to 5, preferably 1 to 3, halogen atoms (e.g., fluorine, chlorine, bromine, iodine etc.), and the like can be mentioned. As specific examples, vinyl, propenyl, 3,3,3-trifluoropropenyl, 2-buten-1-yl, 4,4,4-trifluoro-2-buten-1-yl, 4-penten-1-yl, 5-hexen-1-yl and the like can be mentioned.

As the aforementioned "optionally halogenated $C_{2-6}$ alkynyl", for example, $C_{2-6}$ alkynyl (e.g., 2-butyn-1-yl, 4-pentyn-1-yl, 5-hexyn-1-yl etc.) optionally having 1 to 5, preferably 1 to 3, halogen atoms (e.g., fluorine, chlorine, bromine, iodine etc.), and the like can be mentioned. As specific examples, propargyl, 2-butyn-1-yl, 4,4,4-trifluoro- 2-butyn-1-yl, 4-pentyn-1-yl, 5,5,5-trifluoro-4-pentyn-1-yl, 5-hexyn-1-yl and the like can be mentioned.

As the aforementioned "optionally halogenated $C_{3-8}$ cycloalkyl", for example, $C_{3-8}$ cycloalkyl (e.g., cyclopropyl, cyclobutyl, cyclopentyl, cyclohexyl, cycloheptyl, cyclooctyl etc.) optionally having 1 to 5, preferably, 1 to 3, halogen atoms (e.g., fluorine, chlorine, bromine, iodine etc.), and the like can be mentioned. As specific examples, cyclopropyl, cyclobutyl, cyclopentyl, cyclohexyl, cycloheptyl, cyclooctyl, 4,4-dichlorocyclohexyl, 2,2,3,3-tetrafluorocyclopentyl, 4-chlorocyclohexyl and the like can be mentioned.

As the aforementioned "optionally halogenated $C_{1-8}$ alkoxy", for example, $C_{1-8}$ alkoxy (e.g., methoxy, ethoxy, propoxy, isopropoxy, butoxy, isobutoxy, sec-butoxy, pentyloxy, hexyloxy etc.) optionally having 1 to 5, preferably 1 to 3, halogen atoms (e.g., fluorine, chlorine, bromine, iodine etc.), and the like can be mentioned. As specific examples, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like can be mentioned.

As the aforementioned "optionally halogenated $C_{1-6}$ alkylthio", for example, $C_{1-6}$ alkylthio (e.g., methylthio, ethylthio, propylthio, isopropylthio, butylthio, sec-butylthio, tert-butylthio etc.) optionally having 1 to 5, preferably 1 to 3, halogen atoms (e.g., fluorine, chlorine, bromine, iodine etc.), and the like can be mentioned. As specific examples, methylthio, difluoromethylthio, trifluoromethylthio, ethylthio, propylthio, isopropylthio, butylthio, 4,4,4-trifluorobutylthio, pentylthio, hexylthio and the like can be mentioned.

As the "5- to 7-membered saturated cyclic amino" of the aforementioned "5- to 7-membered saturated cyclic amino optionally having substituents", for example, a 5- to 7-membered saturated cyclic amino optionally containing, besides one nitrogen atom and carbon atom(s), 1 or 2 kinds of 1 to 4 hetero atoms selected from nitrogen atom, sulfur atom and oxygen atom and the like can be mentioned. As specific examples, pyrrolidin-1-yl, piperidino, piperazin-1-yl, morpholino, thiomorpholino, hexahydroazepin-1-yl and the like can be mentioned.

As the "substituent" of the aforementioned "5- to 7-membered saturated cyclic amino optionally having substituents", for example, $C_{1-6}$ alkyl (e.g., methyl, ethyl, propyl, isopropyl, butyl, isobutyl, sec-butyl, tert-butyl, pentyl, hexyl etc.), $C_{6-14}$ aryl (e.g., phenyl, 1-naphthyl, 2-naphthyl, 2-biphenylyl, 3-biphenylyl, 4-biphenylyl, 2-anthryl etc.), $C_{1-6}$ alkyl-carbonyl (e.g., acetyl, propionyl, pivaloyl etc.), 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), oxo and the like can be mentioned. The "5- to 7-membered saturated cyclic amino" is preferably substituted by 1 to 3 of these substituents.

In the present invention, as the "hydrocarbon group" of the "hydrocarbon group optionally having substituent(s)", for example, an acyclic or cyclic hydrocarbon group (e.g., alkyl, alkenyl, alkynyl, cycloalkyl, aryl, aralkyl etc.) and the like can be mentioned. Of these, an acyclic or cyclic hydrocarbon group having 1 to 16 carbon atoms and the like are preferable.

As the "alkyl", for example, $C_{1-6}$ alkyl (e.g., methyl, ethyl, propyl, isopropyl, butyl, isobutyl, sec-butyl, tert-butyl, pentyl, hexyl etc.) and the like are preferable.

As the "alkenyl", for example, $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like are preferable.

As the "alkynyl", for example, $C_{2-6}$ alkynyl (e.g., ethynyl, propargyl, 1-butynyl, 2-butynyl, 3-butynyl, 1-hexynyl etc.) and the like are preferable.

As the "cycloalkyl", for example, $C_{3-8}$ cycloalkyl (e.g., cyclopropyl, cyclobutyl, cyclopentyl, cyclohexyl, cycloheptyl, cyclooctyl etc.) and the like are preferable.

As the "aryl", for example, $C_{6-14}$ aryl (e.g., phenyl, 1-naphthyl, 2-naphthyl, 2-biphenylyl, 3-biphenylyl, 4-biphenylyl, 2-anthryl etc.) and the like are preferable.

As the "aralkyl", for example, $C_{7-16}$ aralkyl (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl etc.) and the like are preferable.

As the "substituent" of the "hydrocarbon group optionally having substituent(s)", for example, oxo, halogen atom (e.g., fluorine, chlorine, bromine, iodine etc.), $C_{1-3}$ alkylenedioxy (e.g., methylenedioxy, ethylenedioxy etc.), nitro, cyano, optionally halogenated $C_{1-6}$ alkyl, optionally halogenated $C_{2-6}$ alkenyl, carboxy $C_{2-6}$ alkenyl (e.g., 2-carboxyethenyl, 2-carboxy-2-methylethenyl etc.), optionally halogenated $C_{2-6}$ alkynyl, optionally halogenated $C_{3-8}$ cycloalkyl, $C_{6-14}$ aryl (e.g., phenyl, 1-naphthyl, 2-naphthyl, 2-biphenylyl, 3-biphenylyl, 4-biphenylyl, 2-anthryl etc.), optionally halogenated $C_{1-8}$ alkoxy, $C_{1-6}$ alkoxy-carbonyl-$C_{1-6}$ alkoxy (e.g., ethoxycarbonylmethyloxy etc.), hydroxy, $C_{6-14}$ aryloxy (e.g., phenyloxy, 1-naphthyloxy, 2-naphthyloxy etc.), $C_{7-16}$ aralkyloxy (e.g., benzyloxy, phenethyloxy etc.), mercapto, optionally halogenated $C_{1-6}$ alkylthio, $C_{6-14}$ arylthio (e.g., phenylthio, 1-naphthylthio, 2-naphthylthio etc.), $C_{7-16}$ aralkylthio (e.g., benzylthio, phenethylthio etc.), amino, mono-$C_{1-6}$ alkylamino (e.g., methylamino, ethylamino etc.), mono-$C_{6-14}$ arylamino (e.g., phenylamino, 1-naphthylamino, 2-naphthylamino etc.), di-$C_{1-6}$ alkylamino (e.g., dimethylamino, diethylamino, ethylmethylamino etc.), $C_{3-8}$ cycloalkylamino (e.g., cyclopentylamino, cyclohexylamino etc.), di-$C_{6-14}$ arylamino (e.g., diphenylamino etc.), formyl, carboxy, carboxy-$C_{1-6}$ alkyl (e.g., carboxymethyl, carboxyethyl etc.), $C_{1-6}$ alkyl-carbonyl (e.g., acetyl, propionyl, pivaloyl etc.), $C_{3-8}$ cycloalkylcarbonyl (e.g., cyclopropylcarbonyl, cyclopentylcarbonyl, cyclohexylcarbonyl etc.), $C_{1-6}$ alkoxy-carbonyl (e.g., methoxycarbonyl, ethoxycarbonyl, propoxycarbonyl, tert-butoxycarbonyl etc.), $C_{6-14}$ aryl-carbonyl (e.g., benzoyl, 1-naphthoyl, 2-naphthoyl etc.), $C_{7-16}$ aralkyl-carbonyl (e.g., phenylacetyl, 3-phenylpropionyl etc.), $C_{6-14}$ aryloxy-carbonyl (e.g., phenoxycarbonyl etc.), $C_{7-16}$ aralkyloxy-carbonyl (e.g., benzyloxycarbonyl, phenethyloxycarbonyl etc.), 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.), carbamoyl, thiocarbamoyl, mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), mono- or di-$C_{6-14}$ aryl-carbamoyl (e.g., phenylcarbamoyl, 1-naphthylcarbamoyl, 2-naphthylcarbamoyl etc.), mono- or di-5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), $C_{1-6}$ alkylsulfonyl (e.g., methylsulfonyl, ethylsulfonyl etc.), $C_{1-6}$ alkylsulfinyl (e.g., methylsulfinyl, ethylsulfinyl etc.), $C_{6-14}$ arylsulfonyl (e.g., phenylsulfonyl, 1-naphthylsulfonyl, 2-naphthylsulfonyl etc.), $C_{6-14}$ arylsulfinyl (e.g., phenylsulfinyl, 1-naphthylsulfinyl, 2-naphthylsulfinyl etc.), formylamino, $C_{1-6}$ alkyl-carbonylamino (e.g., acetylamino, propionylamino, pivaloylamino etc.), $C_{3-8}$ cycloalkyl-carbonylamino (e.g., cyclopentylcarbonylamino, cyclohexylcarbonylamino etc.), $C_{6-14}$ aryl-carbonylamino (e.g., benzoylamino, naphthoylamino etc.), $C_{1-6}$ alkoxy-carbonylamino (e.g., methoxycarbonylamino, ethoxycarbonylamino, propoxycarbonylamino, butoxycarbonylamino etc.), $C_{1-6}$ alkylsulfonylamino (e.g., methylsulfonylamino, ethylsulfonylamino etc.), $C_{6-14}$ arylsulfonylamino (e.g., phenylsulfonylamino, 2-naphthylsulfonylamino, 1-naphthylsulfonylamino etc.), $C_{1-6}$ alkyl-carbonyloxy (e.g., acetoxy, propionyloxy etc.), $C_{6-14}$ aryl-carbonyloxy (e.g., benzoyloxy, naphthylcarbonyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkylcarbamoyloxy (e.g., methylcarbamoyloxy, ethylcarbamoyloxy etc.), di-$C_{1-6}$ alkyl-carbamoyloxy (e.g., dimethylcarbamoyloxy, diethylcarbamoyloxy etc.), mono- or di-$C_{6-14}$ aryl-carbamoyloxy (e.g., phenylcarbamoyloxy, naphthylcarbamoyloxy etc.), nicotinoyloxy, isonicotinoyloxy, 5- to 7-membered saturated cyclic amino optionally having substituents, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), sulfo, sulfamoyl, sulfinamoyl, sulfenamoyl, a group wherein 2 or more (e.g., 2–3) of these substituents are bonded and the like can be mentioned.

The "hydrocarbon group" may have, for example, 1 to 5, preferably 1 to 3, of the above-mentioned substituents at substitutable positions, and when the number of substituents is 2 or more, the respective substituents may be the same or different.

As the aforementioned "optionally halogenated $C_{1-6}$ alkyl", for example, $C_{1-6}$ alkyl (e.g., methyl, ethyl, propyl, isopropyl, butyl, isobutyl, sec-butyl, tert-butyl, pentyl, hexyl etc.) optionally having 1 to 5, preferably 1 to 3, halogen atoms (e.g., fluorine, chlorine, bromine, iodine etc.) and the like can be mentioned. As specific examples, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like can be mentioned.

As the aforementioned "optionally halogenated $C_{2-6}$ alkenyl", for example, $C_{2-6}$ alkenyl (e.g., vinyl, propenyl, isopropenyl, 2-buten-1-yl, 4-penten-1-yl, 5-hexen-1-yl etc.) optionally having 1 to 5, preferably 1 to 3, halogen atoms (e.g., fluorine, chlorine, bromine, iodine etc.) and the like can be mentioned. As specific examples, vinyl, propenyl, 3,3,3-trifluoropropenyl, 2-buten-1-yl, 4,4,4-trifluoro-2-buten-1-yl, 4-penten-1-yl, 5-hexen-1-yl and the like can be mentioned.

As the aforementioned "optionally halogenated $C_{2-6}$ alkynyl", for example, $C_{2-6}$ alkynyl (e.g., 2-butyn-1-yl, 4-pentyn-1-yl, 5-hexyn-1-yl etc.) optionally having 1 to 5, preferably 1 to 3, halogen atoms (e.g., fluorine, chlorine, bromine, iodine etc.) and the like can be mentioned. As specific examples, propargyl, 2-butyn-1-yl, 4,4,4-trifluoro-2-butyn-1-yl, 4-pentyn-1-yl, 5,5,5-trifluoro-4-pentyn-1-yl, 5-hexyn-1-yl and the like can be mentioned.

As the aforementioned "optionally halogenated $C_{3-8}$ cycloalkyl", for example, $C_{3-8}$ cycloalkyl (e.g., cyclopropyl, cyclobutyl, cyclopentyl, cyclohexyl, cycloheptyl, cyclooctyl etc.) optionally having 1 to 5, preferably 1 to 3, halogen atoms (e.g., fluorine, chlorine, bromine, iodine etc.) and the like can be mentioned. As specific examples, cyclopropyl, cyclobutyl, cyclopentyl, cyclohexyl, cycloheptyl, cyclooctyl, 4,4-dichlorocyclohexyl, 2,2,3,3-tetrafluorocyclopentyl, 4-chlorocyclohexyl and the like can be mentioned.

As the aforementioned "optionally halogenated $C_{1-8}$ alkoxy", for example, $C_{1-8}$ alkoxy (e.g., methoxy, ethoxy, propoxy, isopropoxy, butoxy, isobutoxy, sec-butoxy, pentyloxy, hexyloxy etc.) optionally having 1 to 5, preferably 1 to 3, halogen atoms (e.g., fluorine, chlorine, bromine, iodine etc.) and the like can be mentioned. As specific examples, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like can be mentioned.

As the aforementioned "optionally halogenated $C_{1-6}$ alkylthio", for example, $C_{1-6}$ alkylthio (e.g., methylthio, ethylthio, propylthio, isopropylthio, butylthio, sec-butylthio, tert-butylthio etc.) optionally having 1 to 5, preferably 1 to 3, halogen atoms (e.g., fluorine, chlorine, bromine, iodine etc.) and the like can be mentioned. As specific examples, methylthio, difluoromethylthio, trifluoromethylthio, ethylthio, propylthio, isopropylthio, butylthio, 4,4,4-trifluorobutylthio, pentylthio, hexylthio and the like can be mentioned.

As the "5- to 7-membered saturated cyclic amino" of the aforementioned "5- to 7-membered saturated cyclic amino optionally having substituents", for example, a 5- to 7-membered saturated cyclic amino optionally containing, besides one nitrogen atom and carbon atom(s), 1 or 2 kinds of 1 to 4 hetero atoms selected from nitrogen atom, sulfur atom and oxygen atom can be mentioned. As specific examples, pyrrolidin-1-yl, piperidino, piperazin-1-yl, morpholino, thiomorpholino, hexahydroazepin-1-yl and the like can be mentioned.

As the "substituent" of the "5- to 7-membered saturated cyclic amino optionally having substituents", for example, 1 to 3 substituents from $C_{1-6}$ alkyl (e.g., methyl, ethyl, propyl, isopropyl, butyl, isobutyl, sec-butyl, tert-butyl, pentyl, hexyl etc.), $C_{6-14}$ aryl (e.g., phenyl, 1-naphthyl, 2-naphthyl, 2-biphenylyl, 3-biphenylyl, 4-biphenylyl, 2-anthryl etc.), $C_{1-6}$ alkyl-carbonyl (e.g., acetyl, propionyl, pivaloyl etc.), 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), oxo and the like can be mentioned.

In the present invention, the "divalent hydrocarbon group" of the "divalent hydrocarbon group optionally having substituent(s)" refers to a divalent group derived from the "hydrocarbon group" of the aforementioned "hydrocarbon group optionally having substituent(s)", and, for example, a divalent group derived from alkylene, alkenylene, alkynylene or cycloalkane, a divalent group derived from cycloalkene, a divalent group derived from aromatic hydrocarbon ring and the like can be mentioned.

As the "alkylene", for example, $C_{1-15}$ alkylene group (e.g., methylene, ethylene, trimethylene, tetramethylene, pentamethylene, hexamethylene, heptamethylene, octamethylene and the like, preferably $C_{1-6}$ alkylene etc.) and the like can be mentioned.

As the "alkenylene", for example, $C_{2-16}$ alkenylene group (e.g., vinylene, propenylene, 1-butenylene, 2-butenylene, 1-pentenylene, 2-pentenylene, 3-pentenylene etc.) and the like can be mentioned.

As the "alkynylene", for example, $C_{2-16}$ alkynylene group (ethynylene, propynylene, 1-butynylene, 2-butynylene, 1-pentynylene, 2-pentynylene, 3-pentynylene etc.) can be mentioned.

As the "cycloalkane", for example, $C_{3-7}$ cycloalkane such as cyclopropane, cyclobutane, cyclopentane, cyclohexane, cycloheptene, cyclooctane and the like, and the like can be mentioned.

As the "cycloalkene", for example, $C_{3-8}$ cycloalkene such as cyclopropene, cyclobutene, cyclopentene, cyclohexene, cycloheptene, cyclooctene and the like, and the like can be mentioned.

As the "aromatic hydrocarbon ring", a hydrocarbon ring having 6 to 14 carbon atoms such as benzene ring, naphthalene ring and the like, and the like can be mentioned.

The divalent group derived from "cycloalkane", "cycloalkene" or "aromatic hydrocarbon ring" refers to a divalent group obtained by removing two hydrogen atoms from one carbon atom of, or removing one hydrogen atom from each of two different carbon atoms of "cycloalkane", "cycloalkene" or "aromatic hydrocarbon ring", and the like. Specifically, for example,

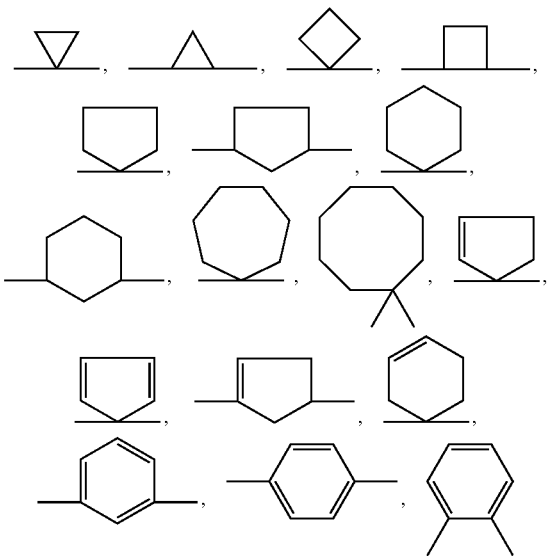

and the like are used, preferably,

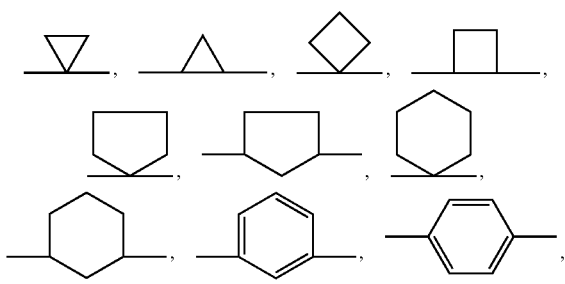

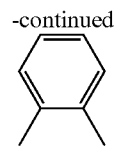

and the like are used, and more preferably,

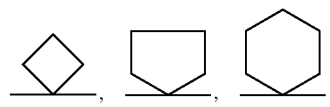

and the like are widely used.

As the "substituent" of the "divalent hydrocarbon group", those similar to the "substituent" of the aforementioned "hydrocarbon group optionally having substituent(s)" can be mentioned.

The "divalent hydrocarbon group" may have, for example, 1 to 4, preferably 1 to 3, of the above-mentioned substituents at substitutable positions, and when the number of substituents is 2 or more, the respective substituents may be the same or different.

As the divalent hydrocarbon group optionally having substituent(s), $C_{1-15}$ alkylene group optionally substituted by oxo group, and the like are preferable. Particularly, $C_{1-6}$ alkylene optionally substituted by oxo group, and the like are preferable.

In the present invention, as the "heterocyclic group" of the "heterocyclic group optionally having substituent(s)", for example, a monovalent group obtained by removing optional one hydrogen atom from a 5- to 14-membered (monocyclic, bicyclic or tricyclic) heterocycle containing, besides carbon atom(s), 1 or 2 kinds of 1 to 4 hetero atoms selected from nitrogen atom, sulfur atom and oxygen atom, preferably (i) a 5- to 14-membered (preferably 5- to 10-membered) aromatic heterocycle, (ii) a 5- to 10-membered non-aromatic heterocycle or (iii) a 7- to 10-membered bridged heterocycle, and the like can be mentioned.

As the above-mentioned "5 to 14-membered (preferably 5 to 10-membered) aromatic heterocycle", for example, an aromatic heterocycle such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, a ring formed by condensation of these rings (preferably monocycle) with one or plural (preferably 1 or 2) aromatic rings (e.g., benzene ring etc.) and the like can be mentioned.

As the above-mentioned "5- to 10-membered non-aromatic heterocycle", for example, pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole and the like can be mentioned.

As the above-mentioned "7 to 10-membered crosslinked heterocycle", for example, quinuclidine, 7-azabicyclo[2.2.1]heptane and the like can be mentioned.

The preferable "heterocyclic group" is a 5 to 14-membered (preferably 5- to 10-membered) (monocyclic or bicyclic) heterocyclic group preferably containing, besides carbon atom(s), 1 or 2 kinds of 1 to 4 hetero atoms selected from nitrogen atom, sulfur atom and oxygen atom. Specific examples include aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, non-aromatic heterocyclic groups such as 1-pyrrolizinyl, 2-pyrrolizinyl, 3-pyrrolizinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like, and the like.

Of these, for example, a 5- or 6-membered heterocyclic group containing, besides carbon atom(s), 1 to 3 hetero atoms selected from nitrogen atom, sulfur atom and oxygen atom, and the like are more preferable. Specifically, 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolizinyl, 2-pyrrolizinyl, 3-pyrrolizinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like can be mentioned.

As the "substituent" of the "heterocyclic group optionally having substituent(s)", those similar to the "substituent" of the aforementioned "hydrocarbon group optionally having substituent(s)" can be mentioned.

The "heterocyclic group" may have, for example, 1 to 5, preferably 1 to 3, of the above-mentioned substituents at substitutable positions, and when the number of substituents is 2 or more, the respective substituents may be the same or different.

In the present invention, as the "acyl group", for example, an acyl group represented by the formula: —(C=O)—$R^7$, —(C=O)—$OR^7$, —(C=O)—$NR^7R^8$, —(C=S)—$NHR^7$ or —$SO_2$—$R^9$ wherein $R^7$ is a hydrogen atom, a hydrocarbon group optionally having substituent(s) or a heterocyclic group optionally having substituent(s), $R^8$ is a hydrogen atom or $C_{1-6}$ alkyl group, and $R^9$ is a hydrocarbon group optionally having substituent(s) or a heterocyclic group optionally having substituent(s), and the like can be mentioned.

As the "hydrocarbon group optionally having substituent(s)" and "heterocyclic group optionally having substituent(s)", those similar to the aforementioned can be used.

As the "$C_{1-6}$ alkyl group", methyl, ethyl, propyl, isopropyl, butyl, isobutyl, sec-butyl, tert-butyl, pentyl, hexyl and the like can be mentioned.

In the present invention, as the "amino group optionally having substituent(s)", (1) an amino group optionally having 1 or 2 substituents and (2) a cyclic amino group optionally having substituent(s) can be mentioned.

As the "substituent" of the "amino group optionally having 1 or 2 substituents" of the above-mentioned (1), for example, a hydrocarbon group optionally having substituent(s), a heterocyclic group optionally having substituent(s), an acyl group, an alkylidene group optionally having substituent(s) and the like can be mentioned. As these "hydrocarbon group optionally having substituent(s)", "heterocyclic group optionally having substituent(s)" and "acyl group", those similar to the aforementioned can be respectively used.

As the "alkylidene group" of the "alkylidene group optionally having substituents", for example, $C_{1-6}$ alkylidene (e.g., methylidene, ethylidene, propylidene etc.) and the like can be mentioned. As the "substituent" of the "alkylidene group optionally having substituents", those similar to the "substituent" of the aforementioned "hydrocarbon group optionally having substituent(s)" can be mentioned. The "alkylidene group" can be substituted by 1 to 5, preferably 1 to 3, of these substituents.

When the number of "substituents" of the above-mentioned "amino group optionally having 1 or 2 substituents" is 2, the respective substituents may be the same or different.

As the "cyclic amino group" of the "cyclic amino group optionally having substituent(s)" of the above-mentioned (2), a 5- to 7-membered non-aromatic cyclic amino group optionally containing, besides one nitrogen atom and carbon atom(s), 1 or 2 kinds of 1 to 4 hetero atoms selected from nitrogen atom, sulfur atom and oxygen atom can be mentioned. As specific examples, pyrrolidin-1-yl, piperidino, piperazin-1-yl, morpholino, thiomorpholino, hexahydroazepin-1-yl, imidazolidin-1-yl, 2,3-dihydro-1H-imidazol-1-yl, tetrahydro-1(2H)-pyrimidinyl, 3,6-dihydro-1(2H)-pyrimidinyl, 3,4-dihydro-1(2H)-pyrimidinyl and the like can be mentioned.

As the "substituent" of the "cyclic amino group optionally having substituent(s)", for example, those similar to the "substituent" of the "5- to 7-membered saturated cyclic amino optionally having substituents" explained in detail as the "substituent" of the aforementioned "hydrocarbon group optionally having substituent(s)", and the like can be mentioned, wherein the "cyclic amino group is preferably substituted by 1 to 3 of these substituents.

As specific examples of a 5- to 7-membered non-aromatic cyclic amino group having one oxo, 2-oxoimidazolidin-1-yl, 2-oxo-2,3-dihydro-1H-imidazol-1-yl, 2-oxotetrahydro-1(2H)-pyrimidinyl, 2-oxo-3,6-dihydro-1(2H)-pyrimidinyl, 2-oxo-3,4-dihydro-1(2H)-pyrimidinyl, 2-oxopyrrolidin-1-yl, 2-oxopiperidino, 2-oxopiperazin-1-yl, 3-oxopiperazin-1-yl, 2-oxo-2,3,4,5,6,7-hexahydroazepin-1-yl and the like can be mentioned.

In the present invention, as the "aromatic group" of the "aromatic group optionally having substituent(s)", for example, aromatic hydrocarbon group, aromatic heterocyclic group and the like can be mentioned.

As the "aromatic hydrocarbon group", for example, a monocyclic or fused polycyclic (di- or tri-cyclic) aromatic hydrocarbon group having 6 to 14 carbon atoms and the like can be mentioned. As specific examples, $C_{6-14}$ aryl such as phenyl, 1-naphthyl, 2-naphthyl, 2-biphenylyl, 3-biphenylyl, 4-biphenylyl, 2-anthryl and the like, and the like, preferably $C_{6-10}$ aryl (e.g., phenyl, 1-naphthyl, 2-naphthyl and the like, preferably phenyl etc.), and the like can be mentioned.

As the "aromatic heterocyclic group", a monovalent group obtained by removing one optional hydrogen atom from a 5- to 14-membered (preferably 5- to 10-membered) aromatic heterocycle containing, besides carbon atom(s), 1 or 2 kinds of 1 to 4 hetero atoms selected from nitrogen atom, sulfur atom and oxygen atom, and the like can be mentioned.

As the "5- to 14-membered (preferably 5- to 10-membered) aromatic heterocycle", for example, aromatic heterocycle such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, a ring formed by condensation of these rings (preferably monocycle) with one or plural (preferably 1 or 2) aromatic rings (e.g., benzene ring etc.), and the like can be mentioned.

As the preferable "aromatic heterocyclic group", a 5- to 14-membered (preferably 5- to 10-membered) (monocyclic or bicyclic) aromatic heterocyclic group preferably containing, besides carbon atom(s), 1 or 2 kinds of 1 to 4 hetero atoms selected from nitrogen atom, sulfur atom and oxygen atom, and the like, specifically, an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like can be mentioned.

As the "substituent" of the "aromatic group optionally having substituent(s)", 1 to 5, preferably 1 to 3, of those similar to the "substituent" of the aforementioned "hydrocarbon group optionally having substituent(s)" can be mentioned. When the number of the substituents is 2 or more, the respective substituents may be the same or different.

In the present invention, as the "substituent" of the "nitrogen atom optionally having substituent(s)", a hydrocarbon group optionally having substituent(s), a heterocyclic group optionally having substituent(s), acyl group and the like can be mentioned.

As the "hydrocarbon group optionally having substituent(s)", "heterocyclic group optionally having substituent(s)" and "acyl group", those similar to the aforementioned are respectively used.

In the present invention, as the "substituent" of the "carbon atom optionally having substituent(s)", a hydrocarbon group optionally having substituent(s), a heterocyclic group optionally having substituent(s), amino group optionally having substituent(s), acyl group, halogen atom (e.g., fluorine, chlorine, bromine, iodine etc.), $C_{1-3}$ alkylenedioxy (e.g., methylenedioxy, ethylenedioxy etc.), nitro, cyano, optionally halogenated $C_{1-8}$ alkoxy, $C_{1-6}$ alkoxy-carbonyl-$C_{1-6}$ alkoxy (e.g., ethoxycarbonylmethyloxy etc.), hydroxy, $C_{6-14}$ aryloxy (e.g., phenyloxy, 1-naphthyloxy, 2-naphthyloxy-etc.), $C_{7-16}$ aralkyloxy (e.g., benzyloxy, phenethyloxy etc.), mercapto, optionally halogenated $C_{1-6}$ alkylthio, $C_{6-14}$ arylthio (e.g., phenylthio, 1-naphthylthio, 2-naphthylthio etc.), $C_{7-16}$ aralkylthio (e.g., benzylthio, phenethylthio etc.), carboxy, $C_{1-6}$ alkylsulfonyl (e.g., methylsulfonyl, ethylsulfonyl etc.), $C_{1-6}$ alkylsulfinyl (e.g., methylsulfinyl, ethylsulfinyl etc.), $C_{6-14}$ arylsulfonyl (e.g., phenylsulfonyl, 1-naphthylsulfonyl, 2-naphthylsulfonyl etc.), $C_{6-14}$ arylsulfinyl (e.g., phenylsulfinyl, 1-naphthylsulfinyl, 2-naphthylsulfinyl etc.), $C_{1-6}$ alkylsulfonylamino (e.g., methylsulfonylamino, ethylsulfonylamino etc.), $C_{6-14}$ arylsulfonylamino (e.g., phenylsulfonylamino, 2-naphthylsulfonylamino, 1-naphthylsulfonylamino etc.), $C_{1-6}$ alkyl-carbonyloxy (e.g., acetoxy, propionyloxy etc.), $C_{6-14}$ aryl-carbonyloxy (e.g., benzoyloxy, naphthylcarbonyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkylcarbamoyloxy (e.g., methylcarbamoyloxy, ethylcarbamoyloxy etc.), di-$C_{1-6}$ alkyl-carbamoyloxy (e.g., dimethylcarbamoyloxy, diethylcarbamoyloxy etc.), $C_{6-14}$ aryl-carbamoyloxy (e.g., phenylcarbamoyloxy, naphthylcarbamoyloxy etc.), nicotinoyloxy, sulfo, sulfamoyl, sulfinamoyl, sulfenamoyl, a group wherein 2 or more (e.g., 2–3) of these substituents are bonded, and the like can be mentioned.

As the above-mentioned "hydrocarbon group optionally having substituent(s)", "heterocyclic group optionally having substituent(s)", "amino group optionally having substituent(s)", "acyl group", "optionally halogenated $C_{1-8}$ alkoxy" and "optionally halogenated $C_{1-6}$ alkylthio", those similar to the aforementioned are respectively used.

In the present invention, as the "substituent" of the "pyridyl group optionally having substituent(s)", those similar to the "substituent" of the aforementioned "hydrocarbon group optionally having substituent(s)" can be mentioned.

The "pyridyl group" may have 1 to 5, preferably 1 to 3, of the above-mentioned substituents at substitutable positions, and when the number of the substituents is 2 or more, the respective substituents may be the same or different. The nitrogen atom in the ring of the "pyridyl group" may be N-oxidized.

In the present invention, as the "aromatic hydrocarbon group" of the "aromatic hydrocarbon group optionally having substituent(s)", for example, a monocyclic or fused polycyclic (di- or tricyclic) aromatic hydrocarbon group having 6 to 14 carbon atoms and the like can be mentioned. As specific examples, $C_{6-14}$ aryl such as phenyl, 1-naphthyl, 2-naphthyl, 2-biphenylyl, 3-biphenylyl, 4-biphenylyl, 2-anthryl and the like, and the like, preferably $C_{6-10}$ aryl and the like (e.g., phenyl, 1-naphthyl, 2-naphthyl and the like, preferably phenyl etc.) can be mentioned.

As the "substituent" of the "aromatic hydrocarbon group optionally having substituent(s)", those similar to the "substituent" of the aforementioned "hydrocarbon group optionally having substituent (s)" can be mentioned. The "aromatic hydrocarbon group" can be substituted by 1 to 5, preferably 1 to 3, of these substituents. When the number of the substituents is 2 or more, the respective substituents may be the same or different.

In the present invention, as the "divalent acyclic hydrocarbon group" of the "divalent acyclic hydrocarbon group optionally having substituent(s)", for example, $C_{1-15}$ alkylene group (e.g., methylene, ethylene, trimethylene, tetramethylene, pentamethylene, hexamethylene, heptamethylene, octamethylene and the like, preferably $C_{1-6}$ alkylene etc.), $C_{2-16}$ alkenylene group (e.g., vinylene, propenylene, 1-butenylene, 2-butenylene, 1-pentenylene, 2-pentenylene, 3-pentenylene etc.), $C_{2-16}$ alkynylene group (ethynylene, propynylene, 1-butynylene, 2-butynylene, 1-pentynylene, 2-pentynylene, 3-pentynylene etc.) and the like, preferably $C_{1-15}$ alkylene group, particularly preferably $C_{1-6}$ alkylene group and the like can be mentioned.

As the "substituent" of the "divalent acyclic hydrocarbon group", those similar to the "substituent" of the aforementioned "hydrocarbon group optionally having substituent(s)" can be mentioned. The "divalent acyclic hydrocarbon group" can be substituted by 1 to 5, preferably 1 to 3, of these substituents. When the number of the substituents is 2 or more, the respective substituents may be the same or different.

In the present invention, as the "cyclic hydrocarbon group" of the "cyclic hydrocarbon group optionally having substituent(s)", cycloalkyl group, aromatic hydrocarbon group and the like can be mentioned.

As the "cycloalkyl", for example, $C_{3-8}$ cycloalkyl (e.g., cyclopropyl, cyclobutyl, cyclopentyl, cyclohexyl, cycloheptyl, cyclooctyl etc.) and the like are preferable.

As the "aromatic hydrocarbon group", a monocyclic or fused polycyclic (di- or tricyclic) aromatic hydrocarbon group having 6 to 14 carbon atoms and the like can be mentioned. As specific examples, $C_{6-14}$ aryl such as phenyl, 1-naphthyl, 2-naphthyl, 2-biphenylyl, 3-biphenylyl, 4-biphenylyl, 2-anthryl and the like, and the like, preferably $C_{6-10}$ aryl (e.g., phenyl, 1-naphthyl, 2-naphthyl and the like, preferably phenyl etc.) and the like can be mentioned.

As the "substituent" of the "cyclic hydrocarbon group", those similar to the "substituent" of the aforementioned "hydrocarbon group optionally having substituent(s)" can be mentioned. The "cyclic hydrocarbon group" can be substituted by 1 to 5, preferably 1 to 3, of these substituents. When the number of the substituents is 2 or more, the respective substituents may be the same or different.

In the present invention, the "optionally oxidized sulfur atom" methods S, SO and $SO_2$.

In compound (I), as the basic backbone of the "azole compound", for example,

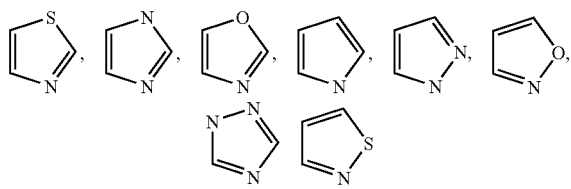

and the like can be mentioned. Of these,

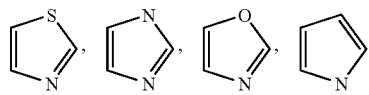

and the like are preferable, particularly

is preferable.

The position of substitution in the azole backbone, where the "nitrogen-containing aromatic group having substituent(s)" is attached, is not particularly limited. For example, the positions shown with→in the following are preferable.

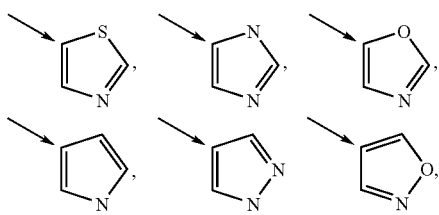

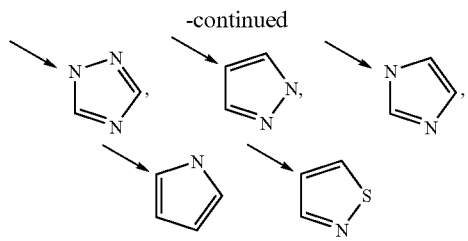

The "aromatic ring" denoted by ring B consists of $N^1$, $X^1$, $X^2$, $X^3$ and carbon atom, and specifically forms an azole backbone. As such azole backbone, those similar to the basic backbone of the aforementioned "azole compound" are used.

As the "nitrogen-containing aromatic group" of the "nitrogen-containing aromatic group having substituent(s)", for example, 5- to 14-membered (preferably 5- to 10-membered) (monocyclic or bicyclic) nitrogen-containing aromatic heterocyclic group containing one nitrogen atom and 1 or 2 kinds of preferably 1 to 4 atoms selected from carbon atom, nitrogen atom, sulfur atom and oxygen atom, and the like can be mentioned. Specifically, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl and the like can be mentioned. Of these, 4-pyridyl group, 4-pyrimidinyl group and the like are preferable. The nitrogen atom of these nitrogen-containing aromatic groups may be N-oxidized.

As the "substituent" of the "nitrogen-containing aromatic group", for example, a group represented by the formula: —Z—W—$R^3$ wherein Z is a bond, —$NR^4$— wherein $R^4$ is a hydrogen atom or a hydrocarbon group optionally having substituent(s), an oxygen atom or an optionally oxidized sulfur atom, W is a divalent hydrocarbon group optionally having substituent(s) or a bond, and $R^3$ is a hydrocarbon group optionally having substituent(s) or a heterocyclic group optionally having substituent(s), as well as halogen atom, $C_{1-3}$ alkylenedioxy, nitro, cyano, hydroxy, mercapto, amino, formyl, carboxy, $C_{6-14}$ aryloxy-carbonyl, $C_{7-16}$ aralkyloxy-carbonyl, carbamoyl, thiocarbamoyl, mono-$C_{1-6}$ alkylcarbamoyl, di-$C_{1-6}$ alkyl-carbamoyl, mono- or di-$C_{6-14}$ aryl-carbamoyl, a mono- or di-5- or 6-membered heterocyclic carbamoyl, $C_{1-6}$ alkylsulfonyl, $C_{1-6}$ alkylsulfinyl, $C_{6-14}$ arylsulfonyl, $C_{6-14}$ arylsulfinyl, formylamino, $C_{1-6}$ alkoxy-carbonylamino, $C_{1-6}$ alkylsulfonylamino, $C_{6-14}$ arylsulfonylamino, $C_{1-6}$ alkoxy-carbonyloxy, mono-$C_{1-6}$ alkyl-carbamoyloxy, di-$C_{1-6}$ alkyl-carbamoyloxy, mono- or di-$C_{6-14}$ aryl-carbamoyloxy, nicotinoyloxy, a 5- to 7-membered saturated cyclic amino optionally having substituents, sulfo, sulfamoyl, sulfinamoyl, sulfenamoyl, a group wherein 2 or more (e.g., 2–3) of these substituents are bonded and the like, which are exemplified as the substituent of the aforementioned ring A, can be mentioned. Particularly, a group represented by the formula: —Z—W—$R^3$ is preferable.

Particularly, a substituent represented by the formula: —Z—W—$R^3$ is preferably present adjacent to the nitrogen atom of the nitrogen-containing aromatic group (particularly, 4-pyridyl group or 4-pyrimidinyl group).

The above-mentioned "nitrogen-containing aromatic group" may have, for example, 1 to 5, preferably 1 to 3, of the above-mentioned substituents at substitutable positions.

When the number of the substituents is 2 or more, the respective substituents may be the same or different.

The azole compound (I) may have "substituent(s)" besides the "nitrogen-containing aromatic group having substituent(s)", and the "hydrocarbon group optionally having substituent(s)", "heterocyclic group optionally having substituent(s)", "acyl group", "amino group optionally having substituent(s)", as well as halogen atom, $C_{1-3}$ alkylenedioxy, nitro, cyano, optionally halogenated $C_{1-8}$ alkoxy, $C_{1-6}$ alkoxycarbonyl-$C_{1-6}$ alkoxy, hydroxy, $C_{6-14}$ aryloxy, $C_{7-16}$ aralkyloxy, mercapto, optionally halogenated $C_{1-6}$ alkylthio, $C_{6-14}$ arylthio, $C_{7-16}$ aralkylthio, formyl, carboxy, carbamoyl, thiocarbamoyl, mono-$C_{1-6}$ alkyl-carbamoyl, di-$C_{1-6}$ alkyl-carbamoyl, mono- or di-$C_{6-14}$ aryl-carbamoyl, mono- or di-5- or 6-membered heterocyclic carbamoyl, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkylcarbamoyloxy, mono- or di-$C_{6-14}$ aryl-carbamoyloxy, nicotinoyloxy, 5- to 7-membered saturated cyclic amino optionally having substituent(s), sulfo etc., sulfamoyl, sulfinamoyl, sulfenamoyl, a group wherein 2 or more (e.g., 2-3) of these substituents are bonded and the like, which are exemplified as the substituent of the aforementioned ring A, can be mentioned. The number of the substituents is 1 to 3, preferably 1 or 2, and when the number of the substituents is 2 or more, the respective substituents may be the same or different.

As the Compound (I) (except compounds described in the above-mentioned reference (WO01/91749)), for example, the following Compounds (I'), (I"), (Ia)–(IL) and the like are specifically used. Each symbol in each formula designates the same meaning as above.

As specific examples of Compound (I'), Compounds (Ia) [including (Ia'), (Ia") and (Ia'")], (Ib), (Ic), (Id), (Ii), (Ij), (Ik) and (IL) as well as (I") can be mentioned.

As preferable compounds of Compounds (I"), Compounds (Ie) [including (Ie'), (Ie") and (Ie'")], (If) [including (If')], (Ig) [including (Ig')] and (Ih) [including (Ih')] can be mentioned.

As Compound (I), compounds (Ij), (Ik) and (IL) are particularly preferable.

[1] Compound (I')

An optionally N-oxidized compound represented by the formula:

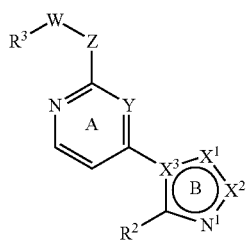

(I')

wherein $N^1$ is a nitrogen atom optionally having a substituent or a hydrogen atom, $X^1$ is (i) a carbon atom optionally having substituent(s) or hydrogen atom(s), (ii) an oxygen atom, (iii) a sulfur atom or (iv) a nitrogen atom optionally having a substituent or a hydrogen atom, $X^2$ is (i) a carbon atom optionally having substituent(s) or hydrogen atom(s), (ii) an oxygen atom, (iii) a sulfur atom or (iv) a nitrogen atom optionally having a substituent or a hydrogen atom, $X^3$ is (i) a carbon atom or (ii) a nitrogen atom, wherein
(1) when $X^1$ is an oxygen atom or a sulfur atom, $X^2$ is a carbon atom optionally having substituent(s) or hydrogen atom(s), $X^3$ is a carbon atom and $N^1$ is a nitrogen atom,
(2) when $X^1$ is a nitrogen atom having a substituent or a hydrogen atom and $X^3$ is a carbon atom, $X^2$ is a carbon atom optionally having substituent(s) or hydrogen atom(s) and $N^1$ is a nitrogen atom,
(3) when $X^1$ and $X^3$ are each a nitrogen atom, $X^2$ is a carbon atom optionally having substituent(s) or hydrogen atom(s) and $N^1$ is a nitrogen atom,
(4) when $X^1$ is a carbon atom optionally having substituent(s) or hydrogen atom(s) and $X^2$ is an oxygen atom or a sulfur atom, $X^3$ is a carbon atom and $N^1$ is a nitrogen atom,
(5) when $X^1$ is a carbon atom optionally having substituent(s) or hydrogen atom(s) and $X^3$ is a carbon atom, one of $N^1$ and $X^2$ is a nitrogen atom, and the other is a nitrogen atom having a substituent or a hydrogen atom,
(6) when $X^1$ and $X^2$ are each a carbon atom optionally having substituent(s) or hydrogen atom(s) and $X^3$ is a carbon atom, $N^1$ is a nitrogen atom having a substituent or a hydrogen atom, and
(7) when $X^1$ and $X^2$ are each a carbon atom optionally having substituent(s) or hydrogen atom(s) and $X^3$ is a nitrogen atom, $N^1$ is a nitrogen-atom, ring A optionally further has substituent(s), ring B is an aromatic ring, Y is (i) a carbon atom optionally having substituent(s) or hydrogen atom(s) or (ii) a nitrogen atom, Z is a bond, —$NR^4$— ($R^4$ is a hydrogen atom or a hydrocarbon group optionally having substituent(s)), an oxygen atom or an optionally oxidized sulfur atom, W is a bond or a divalent hydrocarbon group optionally having substituent(s), $R^2$ is an aromatic group optionally having substituent(s), and $R^3$ is a hydrocarbon group optionally having substituent(s) or a heterocyclic group optionally having substituent(s), except the compound described in the above-mentioned reference (WO01/91749).

[2] Compound (Ia)

An optionally N-oxidized compound represented by the formula:

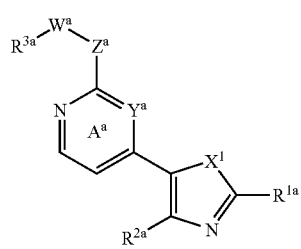

(Ia)

wherein $X^a$ is (i) an oxygen atom, (ii) a sulfur atom, (iii) a nitrogen atom optionally having a substituent or a hydrogen atom, ring $A^a$ optionally further has substituent(s), $Y^a$ is (i) a carbon atom optionally having substituent(s) or hydrogen atom(s) or (ii) a nitrogen atom, $Z^a$ is a bond, —NR$^{4a}$— (R$^{4a}$ is a hydrogen atom or a hydrocarbon group optionally having substituent(s)), an oxygen atom or an optionally oxidized sulfur atom, W$^a$ is a bond or a divalent hydrocarbon group optionally having substituent(s), R$^{1a}$ is a hydrogen atom, a hydrocarbon group optionally having substituent(s), a heterocyclic group optionally having substituent(s), an amino group optionally having substituent(s) or an acyl group, R$^{2a}$ is an aromatic group optionally having substituent(s), R$^{3a}$ is a hydrocarbon group optionally having substituent(s) or a heterocyclic group optionally having substituent(s) except the compound described in the above-mentioned reference (WO01/91749).

[3] Compound (I')

An optionally N-oxidized compound represented by the formula:

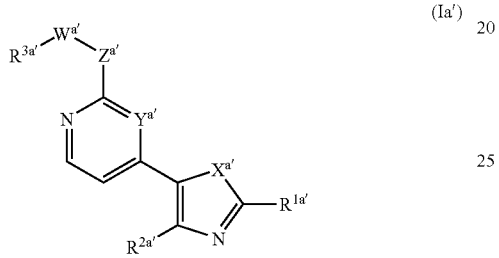

(Ia')

wherein

X$^{a'}$ is (i) an oxygen atom or (ii) a sulfur atom,

Y$^{a'}$ is a carbon atom or a nitrogen atom,

Z$^{a'}$ is a bond, —NR$^{4a'}$— (R$^{4a'}$ is a hydrogen atom or a hydrocarbon group optionally having substituent(s)), an oxygen atom or an optionally oxidized sulfur atom, W$^{a'}$ is a bond or a divalent hydrocarbon group optionally having substituent(s), R$^{1a'}$ is a hydrogen atom, a hydrocarbon group optionally having substituent(s), a heterocyclic group optionally having substituent(s), an amino group optionally having substituent(s) or an acyl group, R$^{2a'}$ is an aromatic group optionally having substituent(s), and R$^{3a'}$ is a hydrocarbon group optionally having substituent(s) or a heterocyclic group optionally having substituent(s).

[4] Compound (I')

An optionally N-oxidized compound represented by the formula:

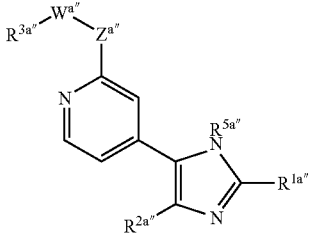

(Ia'')

wherein

Z$^{a''}$ is a bond, —NR$^{4a''}$— (R$^{4a''}$ is a hydrogen atom or a hydrocarbon group optionally having substituent(s)), an oxygen atom or an optionally oxidized sulfur atom, W$^{a''}$ is a bond or a divalent hydrocarbon group optionally having substituent(s).

R$^{1a''}$ is a hydrogen atom, a hydrocarbon group optionally having substituent(s), a heterocyclic group optionally having substituent(s), an amino group optionally having substituent(s) or an acyl group, R$^{2a''}$ is an aromatic group optionally having substituent(s), R$^{3a''}$ is a hydrocarbon group optionally having substituent(s) or a heterocyclic group optionally having substituent(s), R$^{5a''}$ is a hydrogen atom, a hydrocarbon group optionally having substituent(s) or a heterocyclic group optionally having substituent(s).

[5] Compound (I')

An optionally N-oxidized compound represented by the formula:

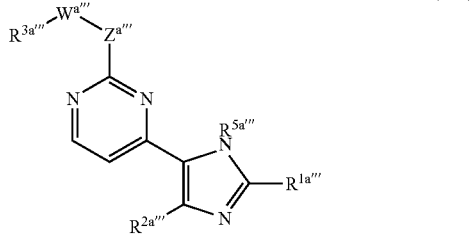

(Ia''')

wherein

Z$^{a'''}$ is a bond, —NR$^{4a'''}$— (R$^{4a'''}$ is a hydrogen atom or a hydrocarbon group optionally having substituent(s)), an oxygen atom or an optionally oxidized sulfur atom, W$^{a'''}$ is a bond or a divalent hydrocarbon group optionally having substituent(s), R$^{1a'''}$ is a hydrogen atom, a hydrocarbon group optionally having substituent(s) other than a non-aromatic heterocyclic group, an aromatic heterocyclic group optionally having substituent(s), an amino group optionally having substituent(s) or an acyl group, R$^{2a'''}$ is an aromatic group optionally having substituent(s), R$^{3a'''}$ is a hydrocarbon group optionally having substituent(s) or a heterocyclic group optionally having substituent(s), and R$^{5a'''}$ is a hydrogen atom, a hydrocarbon group optionally having substituent(s) or a heterocyclic group optionally having substituent(s).

The above-mentioned "hydrocarbon group optionally having substituent(s) other than a non-aromatic heterocyclic group" methods the same as the aforementioned "hydrocarbon group optionally having substituent(s)" except that the substituent does not include a "non-aromatic heterocyclic group".

As the "aromatic heterocyclic group" of the above-mentioned "aromatic heterocyclic group optionally having substituent(s)", a monovalent group obtained by removing one optional hydrogen atom from a 5- to 14-membered aromatic ring exemplified as the "heterocyclic group" of the aforementioned "a heterocyclic group optionally having substituent(s)", and the like can be mentioned.

As the "substituent" of the above-mentioned "aromatic heterocyclic group optionally having substituent(s)", those similar to the substituent of the aforementioned "heterocyclic group optionally having substituent(s)" can be mentioned.

As specific examples of the above-mentioned "aromatic heterocyclic group optionally having substituent(s)", for example, thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like can be mentioned.

[6] Compound (Ib)

An optionally N-oxidized compound represented by the formula:

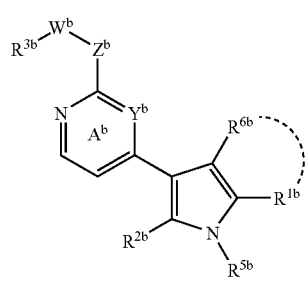

(Ib)

wherein ring $A^b$ optionally further has substituent(s), $Y^b$ is (i) a carbon atom optionally having substituent(s) or hydrogen atom(s) or (ii) a nitrogen atom, $Z^b$ is a bond, —$NR^{4b}$— ($R^{4b}$ is a hydrogen atom or a hydrocarbon group optionally having substituent(s)), an oxygen atom or an optionally oxidized sulfur atom, $W^b$ is a bond or a divalent hydrocarbon group optionally having substituent(s), $R^{1b}$ is a hydrogen atom, a hydrocarbon group optionally having substituent(s), a heterocyclic group optionally having substituent(s), an amino group optionally having substituent(s) or an acyl group, $R^{2b}$ is an aromatic group optionally having substituent(s), $R^{3b}$ is a hydrocarbon group optionally having substituent(s) or a heterocyclic group optionally having substituent(s), $R^{5b}$ is a hydrogen atom, a hydrocarbon group optionally having substituent(s) or a heterocyclic group optionally having substituent(s), $R^{6b}$ is a hydrogen atom, a hydrocarbon group optionally having substituent(s), a heterocyclic group optionally having substituent(s), an amino group optionally having substituent(s) or an acyl group, and $R^{1b}$ and $R^{6b}$ are optionally linked to form a ring.

In the formula, as the ring formed by $R^{1b}$ and $R^{6b}$ linked to each other, a 5- to 9-membered (preferably 5- or 6-membered) ring optionally containing, besides carbon atom(s), 1 to 3 hetero atoms selected from nitrogen atom, oxygen atom, sulfur atom and the like, and the like are used.

Specifically, for example, a ring represented by

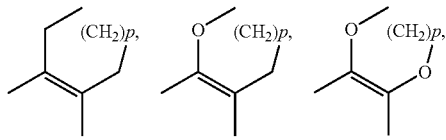

-continued

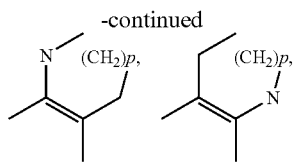

wherein p is an integer of 1 to 5, and the like are used. As p, 1 or 2 is preferable.

[7] Compound (Ic)

An optionally N-oxidized compound represented by the formula:

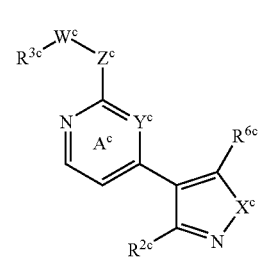

(Ic)

wherein ring $A^c$ optionally further has substituent(s), $X^c$ is (i) an oxygen atom, (ii) a sulfur atom or (iii) a nitrogen atom optionally having a substituent or a hydrogen atom, $Y^c$ is (i) a carbon atom optionally having substituent(s) or hydrogen atom(s) or (ii) a nitrogen atom, $Z^c$ is a bond, —$NR^{4c}$— ($R^{4c}$ is a hydrogen atom or a hydrocarbon group optionally having substituent(s)), an oxygen atom or an optionally oxidized sulfur atom, $W^c$ is a bond or a divalent hydrocarbon group optionally having substituent(s), $R^{2c}$ is an aromatic group optionally having substituent(s), $R^{3c}$ is a hydrocarbon group optionally having substituent(s) or a heterocyclic group optionally having substituent(s), and $R^{6c}$ is a hydrogen atom, a hydrocarbon group optionally having substituent(s), a heterocyclic group optionally having substituent(s), an amino group optionally having substituent(s) or an acyl group.

[8] Compound (Id)

An optionally N-oxidized compound represented by the formula:

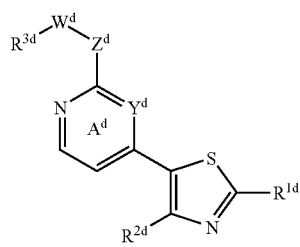

(Id)

wherein
ring Ad optionally further has substituent(s),
$Y^d$ is (i) a carbon atom optionally having substituent(s) or hydrogen atom(s) or (ii) a nitrogen atom,
$Z^d$ is a bond, $-NR^{4d}-$ ($R^{4d}$ is a hydrogen atom or a hydrocarbon group optionally having substituent(s)), an oxygen atom or an optionally oxidized sulfur atom,
$W^d$ is a bond or a divalent hydrocarbon group optionally having substituent(s),
$R^{1d}$ is a hydrogen atom, a hydrocarbon group optionally having substituent(s), a heterocyclic group optionally having substituent(s), an amino group optionally having substituent(s) or an acyl group,
$R^{2d}$ is an aromatic group optionally having substituent(s), and
$R^{3d}$ is a hydrocarbon group optionally having substituent(s) or a heterocyclic group optionally having substituent(s).

[9] Compound (I″)

An optionally N-oxidized compound represented by the formula:

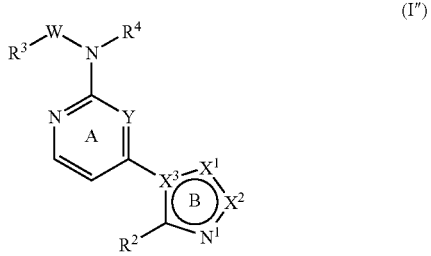

(I″)

wherein
$N^1$ is a nitrogen atom optionally having a substituent or a hydrogen atom,
$X^1$ is (i) a carbon atom optionally having substituent(s) or hydrogen atom(s), (ii) an oxygen atom, (iii) a sulfur atom or (iv) a nitrogen atom optionally having a substituent or a hydrogen atom,
$X^2$ is (i) a carbon atom optionally having substituent(s) or hydrogen atom(s), (ii) an oxygen atom, (iii) a sulfur atom or (iv) a nitrogen atom optionally having a substituent or a hydrogen atom,
$X^3$ is (i) a carbon atom or (ii) a nitrogen atom, wherein
  (1) when $X^1$ is an oxygen atom or a sulfur atom, $X^2$ is a carbon atom optionally having substituent(s) or hydrogen atom(s), $X^3$ is a carbon atom and $N^1$ is a nitrogen atom,
  (2) when $X^1$ is a nitrogen atom having a substituent or a hydrogen atom and $X^3$ is a carbon atom, $X^2$ is a carbon atom optionally having substituent(s) or hydrogen atom(s), and $N^1$ is a nitrogen atom,
  (3) when $X^1$ and $X^3$ is a nitrogen atom, $X^2$ is a carbon atom optionally having substituent(s) or hydrogen atom(s), and $N^1$ is a nitrogen atom,
  (4) when $X^1$ is a carbon atom optionally having substituent(s) or hydrogen atom(s) and $X^2$ is an oxygen atom or a sulfur atom, $X^3$ is a carbon atom, and $N^1$ is a nitrogen atom,
  (5) when $X^1$ is a carbon atom optionally having substituent(s) or hydrogen atom(s) and $X^3$ is a carbon atom, one of $N^1$ and $X^2$ is a nitrogen atom, and the other is a nitrogen atom having a substituent or a hydrogen atom,
  (6), when $X^1$ and $X^2$ are each a carbon atom optionally having substituent(s) or hydrogen atom(s) and $X^3$ is a carbon atom, $N^1$ is a nitrogen atom having a substituent or a hydrogen atom, and
  (7) when $X^1$ and $X^2$ are each a carbon atom optionally having substituent(s) or hydrogen atom(s) and $X^3$ is a nitrogen atom,
$N^1$ is a nitrogen atom,
ring A optionally further has substituent(s),
ring B is an aromatic ring,
Y is (i) a carbon atom optionally having substituent(s) or hydrogen atom(s) or (ii) a nitrogen atom,
W is a bond or a divalent hydrocarbon group optionally having substituent (s),
$R^2$ is an aromatic group optionally having substituent(s),
$R^3$ is a hydrocarbon group optionally having substituent(s) or a heterocyclic group optionally having substituent(s), and
$R^4$ is a hydrogen atom or a hydrocarbon group optionally having substituent(s), except the compound described in the above-mentioned reference (WO01/91749).

[10] Compound (Ie)

An optionally N-oxidized compound represented by the formula:

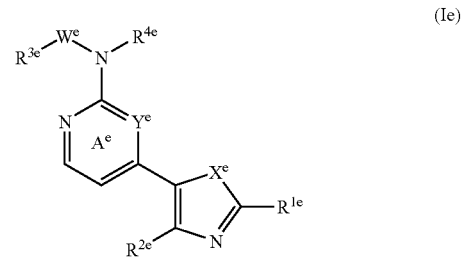

(Ie)

wherein
ring $A^e$ optionally further has substituent(s),
$X^e$ is (i) an oxygen atom, (ii) a sulfur atom or (iii) a nitrogen atom optionally having a substituent or a hydrogen atom,
$Y^e$ is (i) a carbon atom optionally having substituent(s) or hydrogen atom(s) or (ii) a nitrogen atom,
$W^e$ is a bond or a divalent hydrocarbon group optionally having substituent(s),
$R^{1e}$ is a hydrogen atom, a hydrocarbon group optionally having substituent(s), a heterocyclic group optionally having substituent(s), an amino group optionally having substituent(s) or an acyl group,
$R^{2e}$ is an aromatic group optionally having substituent(s),
$R^{3e}$ is a hydrocarbon group optionally having substituent(s) or a heterocyclic group optionally having substituent(s), and
$R^{4e}$ is a hydrogen atom or a hydrocarbon group optionally having substituent(s), except the compound described in the above-mentioned reference (WO01/91749).

[11] Compound (Ie′)

An optionally N-oxidized compound represented by the formula:

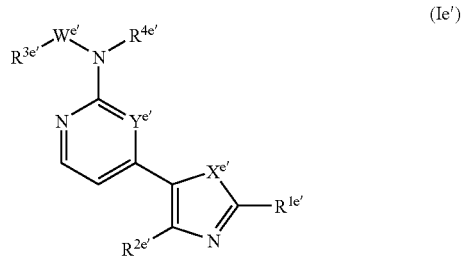

(Ie′)

wherein $X^{e'}$ is (i) an oxygen atom or (ii) a sulfur atom, $Y^{e'}$ is a carbon atom optionally having substituent(s) or hydrogen atom(s), or nitrogen atom $W^{e'}$ is a bond or a divalent hydrocarbon group optionally having substituent(s), $R^{1e'}$ is a hydrogen atom, a hydrocarbon group optionally having substituent(s), a heterocyclic group optionally having substituent(s), an amino group optionally having substituent(s) or an acyl group, $R^{2e'}$ is an aromatic group optionally having substituent(s), $R^{3e'}$ is a hydrocarbon group optionally having substituent(s) or a heterocyclic group optionally having substituent(s), and $R^{4e'}$ is a hydrogen atom or a hydrocarbon group optionally having substituent(s).

[12] Compound (Ie″)

An optionally N-oxidized compound represented by the formula:

$$\text{(Ie″)}$$

wherein $W^{e''}$ is a bond or a divalent hydrocarbon group optionally having substituent(s), $R^{1e''}$ is a hydrogen atom, a hydrocarbon group optionally having substituent(s), a heterocyclic group optionally having substituent(s), an amino group optionally having substituent(s) or an acyl group, $R^{2a''}$ is an aromatic group optionally having substituent(s), $R^{3e''}$ is a hydrocarbon group optionally having substituent(s) or a heterocyclic group optionally having substituent(s), $R^{4e''}$ is a hydrogen atom or a hydrocarbon group optionally having substituent(s), and $R^{5e''}$ is a hydrogen atom, a hydrocarbon group optionally having substituent(s) or a heterocyclic group optionally having substituent(s).

[13] Compound (Ie‴)

An optionally N-oxidized compound represented by the formula:

$$\text{(Ie‴)}$$

wherein $W^{e'''}$ is a bond or a divalent hydrocarbon group optionally having substituent (s), $R^{1e'''}$ is a hydrogen atom, a hydrocarbon group optionally having substituent(s) other than a non-aromatic heterocyclic group, an aromatic heterocyclic group optionally having substituent(s), an amino group optionally-having substituent(s) or an acyl group, $R^{2e'''}$ is an aromatic group optionally having substituent(s), $R^{3e'''}$ is a hydrocarbon group optionally having substituent(s) or a heterocyclic group optionally having substituent(s), $R^{4e'''}$ is a hydrogen atom or a hydrocarbon group optionally having substituent(s), and $R^{5e'''}$ is a hydrogen atom, a hydrocarbon group optionally having substituent(s) or a heterocyclic group optionally having substituent(s).

The above-mentioned "hydrocarbon group optionally having substituent(s) other than a non-aromatic heterocyclic group" methods the same as the aforementioned "hydrocarbon group optionally having substituent(s)" except that the substituent does not include a "non-aromatic heterocyclic group".

As the "aromatic heterocyclic group" of the above-mentioned aromatic heterocyclic group optionally having substituent(s)", a monovalent group obtained by removing one optional hydrogen atom from a 5- to 14-membered aromatic ring, exemplified as the "heterocyclic group" of the aforementioned "heterocyclic group optionally having substituent(s)", and the like can be mentioned.

As the "substituent" of the above-mentioned "aromatic heterocyclic group optionally having substituent(s)", those similar to the "substituent" of the aforementioned "heterocyclic group optionally having substituent(s)" can be mentioned.

As specific examples of the above-mentioned "aromatic heterocyclic group optionally having substituent(s)", thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like can be mentioned.

[14] Compound (If)

An optionally N-oxidized compound represented by the formula:

$$\text{(If)}$$

wherein ring $A^f$ optionally further has substituent(s)

$Y^f$ is (i) a carbon atom optionally having substituent(s) or hydrogen atom(s) or (ii) a nitrogen atom, $W^f$ is a bond or a divalent hydrocarbon group optionally having substituent(s), $R^{1f}$ is a hydrogen atom, a hydrocarbon group optionally having substituent(s), a heterocyclic group optionally having substituent(s), an amino group optionally having substituent(s) or an acyl group, $R^{2f}$ is an aromatic group optionally having substituent(s), $R^{3f}$ is a hydrocarbon group optionally having substituent(s) or a heterocyclic group optionally having substituent(s), and $R^{4f}$ is a hydrogen atom or a hydrocarbon group optionally having substituent(s).

[15] Compound (Ig)

An optionally N-oxidized compound represented by the formula:

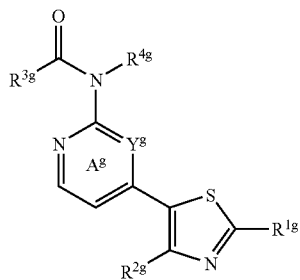

(Ig)

wherein ring Ag optionally further has substituent(s), $Y^g$ is (i) a carbon atom optionally having substituent(s) or hydrogen atom(s) or (ii) a nitrogen atom, $R^{1g}$ is a hydrogen atom, a hydrocarbon group optionally having substituent(s), a heterocyclic group optionally having substituent(s), an amino group optionally having substituent(s) or an acyl group, $R^{2g}$ is an aromatic group optionally having substituent(s), $R^{3g}$ is a hydrocarbon group optionally having substituent(s) or a heterocyclic group optionally having substituent(s), and $R^{4g}$ is a hydrogen atom or a hydrocarbon group optionally having substituent(s).

[16] Compound (Ih)

An optionally N-oxidized compound represented by the formula:

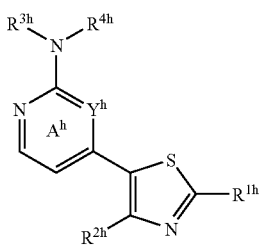

(Ih)

wherein ring A optionally further has substituent(s), $Y^h$ is (i) a carbon atom optionally having substituent(s) or hydrogen atom(s) or (ii) a nitrogen atom, $R^{1h}$ is a hydrogen atom, a hydrocarbon group optionally having substituent(s), a heterocyclic group optionally having substituent(s), an amino group optionally having substituent(s) or an acyl group, $R^{2h}$ is an aromatic group optionally having substituent(s), $R^{3h}$ is a hydrocarbon group optionally having substituent(s) or a heterocyclic group optionally having substituent(s), and $R^{4h}$ is a hydrogen atom or a hydrocarbon group optionally having substituent(s).

[17] Compound (Ii)

An optionally N-oxidized compound represented by the formula:

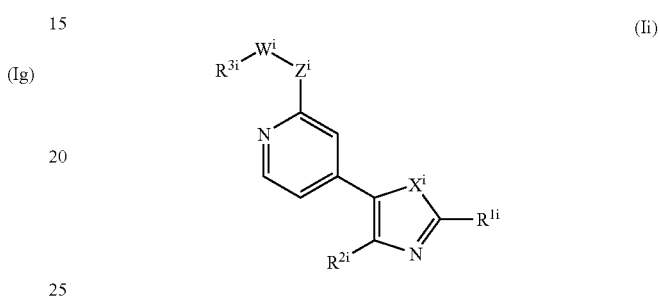

(Ii)

wherein $X^i$ is an oxygen atom or an optionally oxidized sulfur atom, $Z^i$ is a bond, —$NR^{4i}$— ($R^{4i}$ is a hydrogen atom or a hydrocarbon group optionally having substituent(s)), an oxygen atom or an optionally oxidized sulfur atom, $W^i$ is a bond or a divalent acyclic hydrocarbon group optionally having substituent(s), $R^{1i}$ is a hydrogen atom, a hydrocarbon group optionally having substituent(s), a heterocyclic group optionally having substituent(s), an amino group optionally having substituent(s) or an acyl group, $R^{2i}$ is a pyridyl group optionally having substituent(s) or an aromatic hydrocarbon group optionally having substituent(s), and $R^{3i}$ is a hydrocarbon group optionally having substituent(s) or a heterocyclic group optionally having substituent(s).

In the formula (Ii), $R^{1i}$ is preferably a hydrogen atom, an amino group optionally having substituent(s), an aryl group optionally having substituent(s), an alkyl group optionally having substituent(s) and the like.

More preferable "amino group optionally having substituent(s)" is an amino group optionally having 1 or 2 acyl groups represented by the formula: —(C=O)—$R^7$, —(C=O)—$OR^7$, —(C=O)—$NR^7R^8$, —(C=S)—$NHR^7$ or —$SO_2$—$R^9$ wherein each symbol is as defined above. Particularly preferably, it is an amino group optionally having 1 or 2 acyl groups represented by the formula: —(C=O)—$R^7$ or —(C=O)—$NR^7R^8$ wherein each symbol is as defined above.

Preferable "aryl group optionally having substituent(s)" is, for example, $C_{6-14}$ aryl group (preferably phenyl etc.) optionally having 1 to 5 substituents selected from $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl, carboxy and the like, and the like.

As the "alkyl group optionally having substituent(s)", for example, $C_{1-6}$ alkyl group (e.g., methyl, ethyl, propyl, isopropyl, butyl, isobutyl, sec-butyl, tert-butyl and the like) optionally substituted by 1 to 3 substituents selected from halogen atom, $C_{1-6}$ alkoxy, hydroxy, carboxy and $C_{1-6}$ alkoxycarbonyl and the like is preferable, and $C_{1-3}$ alkyl group such as methyl, ethyl and the like are particularly preferable.

Particularly, as $R^{1i}$, (i) $C_{1-6}$ alkyl group (e.g., $C_{1-4}$ alkyl group such as methyl, ethyl, propyl, butyl and the like, and the like), (ii) $C_{6-14}$ aryl group (e.g., phenyl group and the like) optionally substituted by a substituent selected from $C_{1-6}$ alkylthio (e.g., methylthio and the like), $C_{1-6}$ alkylsulfonyl (e.g., methylsulfonyl and the like) and halogen atom (e.g., chlorine atom, fluorine atom and the like) or (iii) an amino group optionally having one or two acyl groups represented by the formula: —(C=O)—$R^{7i}$ wherein $R^{7i}$ is (1) $C_{1-6}$ alkyl group (e.g., $C_{1-3}$ alkyl group such as methyl and the like, and the like), (2) $C_{6-14}$ aryl group (e.g., phenyl group and the like) or (3) a 5- to 14-membered heterocyclic group containing, besides carbon atom(s), 1 or 2 kinds of 1 to 4 hetero atoms selected from nitrogen atom, sulfur atom and oxygen atom (e.g., 5- or 6-membered heterocyclic group containing, besides carbon atom(s), 1 or 2 hetero atoms selected from nitrogen atom, sulfur atom and oxygen atom such as pyridyl group etc., and the like), and the like are preferable. As $R^{7i}$, phenyl group optionally having substituent(s) and pyridyl group optionally having substituent(s) are preferable.

As $R^{2i}$ in the formula (Ii), (1) $C_{6-14}$ aryl group optionally having substituent(s) and (2) a 5 to 14-membered aromatic heterocyclic group optionally having substituent(s), which contains, besides carbon atom(s), 1 or 2 kinds of 1 to 4 hetero atoms selected from nitrogen atom, sulfur atom and oxygen atom are preferable. Of these, (1) $C_{6-14}$ aryl group (e.g., phenyl group, naphthyl group and the like) optionally substituted by halogen atom (e.g., chlorine atom, fluorine atom and the like), $C_{1-6}$ alkyl (e.g., methyl, ethyl and the like) or $C_{1-6}$ alkoxy (e.g., methoxy and the like), (2) a 5- to 14-membered aromatic heterocyclic group containing, besides carbon atom(s), 1 or 2 kinds of 1 to 4 hetero atoms selected from nitrogen atom, sulfur atom and oxygen atom (e.g., a. 5- or 6-membered aromatic heterocyclic group containing, besides carbon atom(s), 1 or 2 hetero atoms selected from nitrogen atom, sulfur atom and oxygen atom such as pyridyl group, thienyl group etc., and the like) and the like are preferable, particularly, phenyl group optionally having substituent(s), pyridyl group optionally having substituent(s) and the like are preferable.

As $R^{3i}$ in the formula (Ii), $C_{6-14}$ aryl group optionally having substituent(s) and $C_{3-8}$ cycloalkyl group optionally having substituent(s) are preferable. Of these, $C_{6-14}$ aryl group optionally substituted by one or two $C_{1-6}$ alkyl (e.g., methyl, ethyl and the like) or $C_{1-6}$ alkoxy (e.g., methoxy, ethoxy and the like), or $C_{3-8}$ cycloalkyl group optionally substituted by 1 to 5 halogen atoms (e.g., fluorine atom, chlorine atom, bromine atom, iodine atom and the like) or $C_{1-6}$ alkyl (e.g., methyl, ethyl and the like), and the like are preferable. Particularly, phenyl group (e.g., 3-methoxyphenyl, 2-methylphenyl, 2,4-dimethylphenyl and the like) optionally substituted by one or two $C_{1-6}$ alkyl or $C_{1-6}$ alkoxy, and $C_{3-6}$ cycloalkyl group (e.g., cyclopropyl, cyclopentyl, cyclohexyl and the like) optionally substituted by 1 to 3 halogen atom(s) or $C_{1-6}$ alkyl, and the like are preferable.

As $X^i$ in the formula (Ii), an optionally oxidized sulfur atom is preferable. More preferably, it is a sulfur atom (S).

As $Z^i$ in the formula (Ii), an oxygen atom, an optionally oxidized sulfur atom, a group represented by the formula: —$NR^{4i}$— wherein $R^{4i}$ is as defined above, and the like are preferable. Of these, an oxygen atom, an optionally oxidized sulfur atom, a group represented by the formula: —$NR^{4i'}$— ($R^{4i'}$ is a hydrogen atom or a $C_{1-6}$ alkyl group) and the like are preferable, an oxygen atom, S, $SO_2$, NH, N($CH_3$) and the like are more preferable and O and NH are particularly preferable.

As $w^i$ in the formula (Ii), a bond or a lower alkylene group (e.g., $C_{1-6}$ alkylene group such as methylene, ethylene, trimethylene and the like, particularly $C_{1-3}$ alkylene group and the like) optionally having a substituent such as $C_{1-3}$ alkyl (e.g., methyl and the like), oxo and the like is preferable, and a bond or a $C_{1-6}$ alkylene group (e.g., $C_{1-3}$ alkylene group such as methylene, ethylene, trimethylene and the like, particularly methylene and the like) optionally having oxo is particularly preferable.

More specifically, as $W^i$, a bond, —$CH_2$—, —$(CH_2)_2$—, —$(CH_2)_3$—, —CO—, —$CH_2CO$—, —$(CH_2)_2CO$—, —CH($CH_3$)— and the like are used, and a bond, —$CH_2$—, —CO—, —$CH_2CO$— and the like are particularly preferable.

The nitrogen atom in Compound (Ii) may be N-oxidized. For example, the nitrogen atom as a ring-constituting atom of the substituent: 4-pyridyl group at the 5-position of a ring represented by the formula:

wherein the symbols are as defined above, may be N-oxidized, and Compound (Ii), for example, a compound represented by the formula:

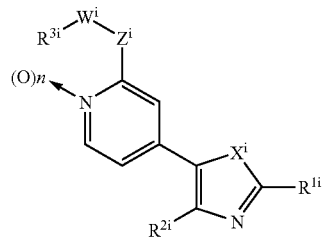

wherein n denotes 0 or 1 and other symbols are as defined above, or a salt thereof and the like are preferable.

As Compound (Ii), for example, the compounds shown in the following (A)–(E) and the like are preferably used.

(A) Compound (Ii) wherein $R^{1i}$ is an amino group optionally having substituent(s), $R^{2i}$ is $C_{6-14}$ aryl group optionally having substituent(s), $R^{3i}$ is $C_{6-14}$ aryl group optionally having substituent(s), or $C_{3-8}$ cycloalkyl group optionally having substituent(s), $X^i$ is sulfur atom, $Z^i$ is oxygen atom or a group represented by the formula: —$NR^{4i}$— wherein $R^{4i}$ is as defined above and/or $w^i$ is lower alkylene group optionally having substituent(s) or a bond.

(B) Compound (Ii) wherein $R^{1i}$ is (i) $C_{1-6}$ alkyl group (e.g., $C_{1-4}$ alkyl group such as methyl, ethyl, propyl, butyl and the like, and the like), (ii) $C_{6-14}$ aryl group (e.g., phenyl group and the like) optionally substituted by a substituent selected from $C_{1-6}$ alkylthio (e.g., methylthio and the like), $C_{1-6}$ alkylsulfonyl (e.g., methylsulfonyl and the like) and halogen atom (e.g., chlorine atom, fluorine atom and the like) or (iii) an amino group optionally having one or two acyl represented by the formula: —(C=O)—$R^{5i'}$ wherein $R^{5i}$ is (1) $C_{1-6}$ alkyl group (e.g., $C_{1-3}$ alkyl group such as methyl and the like, and the like), (2) $C_{6-14}$ aryl group (e.g., phenyl group and the like) or (3) a 5- or 14-membered heterocyclic group containing, besides carbon atom(s), 1 or 2 kinds of 1 to 4 hetero atoms selected from nitrogen atom, sulfur atom and oxygen atom (e.g., 5- or 6-membered heterocyclic group containing, besides carbon atom(s), 1 or 2 hetero atoms selected from nitrogen atom, sulfur atom and oxygen atom, such as pyridyl group and the like), and the like;

$R^{2i}$ is $C_{6-14}$ aryl group (particularly, phenyl group) optionally substituted by 1 or 2 halogen atoms (e.g., fluorine atom, chlorine atom and the like), $C_{1-6}$ alkyl (e.g., methyl and the like) or $C_{1-6}$ alkoxy (e.g., methoxy and the like);

$R^{3i}$ is $C_{6-14}$ aryl group (e.g., phenyl group, naphthyl group and the like) optionally substituted by a halogen atom (e.g., chlorine atom, fluorine atom and the like), $C_{1-6}$ alkyl (e.g., methyl, ethyl and the like) or $C_{1-6}$ alkoxy (e.g., methoxy and the like), a 5 to 14-membered aromatic heterocyclic group containing, besides carbon atom(s), 1 or 2 kinds of 1 to 4 hetero atoms selected from nitrogen atom, sulfur atom and oxygen atom (e.g., a 5- or 6-membered aromatic heterocyclic group containing, besides carbon atom(s), 1 or 2 hetero atoms selected from nitrogen atom, sulfur atom and oxygen atom, such as pyridyl group, thienyl group and the like, and the like) or $C_{3-8}$ cycloalkyl group;

$X_i$ is a sulfur atom;

$Z^i$ is an oxygen atom, an optionally oxidized sulfur atom or a group represented by the formula: $NR^{4i}$ ($R^{4i}$ is a hydrogen atom or $C_{1-6}$ alkyl group) (particularly, oxygen atom, S, $SO_2$, NH, $N(CH_3)$ and the like);

$W^i$ is $C_{1-6}$ alkylene group (particularly, $C_{1-3}$ alkylene group) optionally having oxo or $C_{1-6}$ alkyl (e.g., $C_{1-3}$ alkyl such as methyl and the like, and the like), or a bond.

(C) Compound (Ii) wherein $R^{1i}$ is an amino group optionally having one or two acyl represented by the formula: —(C=O)—$R^{5i''}$ wherein $R^{5i''}$ is (1) $C_{6-14}$ aryl group (e.g., phenyl group and the like) or (2) a 5- to 14-membered heterocyclic group containing, besides carbon atom(s), 1 or 2 kinds of 1 to 4 hetero atoms selected from nitrogen atom, sulfur atom and oxygen atom (e.g., a 5- or 6-membered heterocyclic group containing, besides carbon atom(s), 1 or 2 hetero atoms selected from nitrogen atom, sulfur atom and oxygen atom, such as pyridyl group and the like, and the like);

$R^{2i}$ is $C_{6-14}$ aryl group (particularly, phenyl group) optionally substituted by 1 or 2 halogen atoms (e.g., fluorine atom, chlorine atom and the like), $C_{1-6}$ alkyl (e.g., methyl and the like) or $C_{1-6}$ alkoxy (e.g., methoxy and the like);

$R^{3i}$ is $C_{6-14}$ aryl group (e.g., phenyl group and the like), a 5 to 14-membered aromatic heterocyclic group containing, besides carbon atom(s), 1 or 2 kinds of 1 to 4 hetero atoms selected from nitrogen atom, sulfur atom and oxygen atom (e.g., a 5- or 6-membered aromatic heterocyclic group containing, besides carbon atom(s), 1 or 2 hetero atoms selected from nitrogen atom, sulfur atom and oxygen atom, such as pyridyl group and the like, and the like) or $C_{3-8}$ cycloalkyl group (e.g., cyclopropyl group, cyclopentyl group, cyclohexyl group and the like);

$X_i$ is a sulfur atom;

$Z^i$ is O, NH or S; and $W^i$ is a bond or $C_{1-6}$ alkylene group optionally having oxo (particularly, $C_{1-3}$ alkylene group, such as methylene, ethylene and the like, optionally having oxo).

(D) Compounds produced according to Examples 1–79 of (E) The following Example compounds produced according to WO00/64894.

[4-(3,5-dimethylphenyl)-5-(2-phenylmethyloxy-4-pyridyl)-1,3-thiazol-2-yl]amine (Example compound 1), N-[4-[2-benzoylamino-4-(4-methoxyphenyl)-1,3-thiazol-5-yl]-2-pyridyl]benzamide (Example compound 2), N-[4-(4-methoxyphenyl)-5-[2-[(3-pyridylcarbonylamino)]-4-pyridyl]-1,3-thiazol-2-yl]nicotinamide (Example compound 3), N-[4-[2-amino-4-(4-methoxyphenyl)-1,3-thiazol-5-yl]-2-pyridyl]benzamide (Example compound 4), N-[4-[2-amino-4-(3,5-dimethylphenyl)-1,3-thiazol-5-yl]-2-pyridyl]benzamide (Example compound 5), N-[4-[2-amino-4-(3,5-dimethylphenyl)-1,3-thiazol-5-yl]-2-pyridyl]benzylamine (Example compound 6), N-[4-[2-amino-4-(3,5-dimethylphenyl)-1,3-thiazol-5-yl]-2-pyridyl]benzamide hydrochloride (Example compound 7), N-[4-[2-amino-4-(3,5-dimethylphenyl)-1,3-thiazol-5-yl]-2-pyridyl]benzylamine dihydrochloride (Example compound 8).

(F) N-[5-(2-benzoylamino-4-pyridyl)-4-(3,5-dimethylphenyl)-1,3-thiazol-2-yl]acetamide (Example compound 9), N-[5-(2-benzylamino-4-pyridyl)-4-(3,5-dimethylphenyl)-1,3-thiazol-2-yl]acetamide (Example compound 10), N-[4-[4-(4-methoxyphenyl)-2-methyl-1,3-thiazol-5-yl]-2-pyridyl]benzamide (Example compound 13), N-[4-[2-(4-fluorophenyl)-4-(3-methylphenyl)-1,3-thiazol-5-yl]-2-pyridyl]phenylacetamide (Example compound 14), N-[4-[2-ethyl-4-(3-methylphenyl)-1,3-thiazol-5-yl]-2-pyridyl]phenylacetamide (Example compound 15-2), N-[4-[4-(3-methylphenyl)-2-propyl-1,3-thiazol-5-yl]-2-pyridyl]phenylacetamide (Example compound 15-3), N-[4-[2-butyl-4-(3-methylphenyl)-1,3-thiazol-5-yl]-2-pyridyl]phenylacetamide (Example compound 15-4), N-[4-[4-(3-methylphenyl)-2-(4-methylthiophenyl)-1,3-thiazol-5-yl]-2-pyridyl]phenylacetamide (Example compound 15-6), N-[4-[2-ethyl-4-(3-methylphenyl)-1,3-thiazol-5-yl]-2-pyridyl]benzamide (Example compound 16-1), N-[4-[2-ethyl-4-(3-methylphenyl)-1,3-thiazol-5-yl]-2-pyridyl]-3-phenylpropionamide (Example compound 16-2), N-[4-[2-ethyl-4-(3-methylphenyl)-1,3-thiazol-5-yl]-2-pyridyl]-3-(4-methoxyphenyl)propionamide (Example compound 16-3), N-[4-[2-ethyl-4-(3-methylphenyl)-1,3-thiazol-5-yl]-2-pyridyl]-4-phenylbutylamide (Example compound 16-5), N-[4-[4-(3-methylphenyl)-2-propyl-1,3-thiazol-5-yl]-2-pyridyl]-benzamide (Example compound 16-7), N-[4-[4-(3-methylphenyl)-2-propyl-1,3-thiazol-5-yl]-2-pyridyl]-3-phenylpropionamide (Example compound 16-8), N-[4-[2-butyl-4-(3-methylphenyl)-1,3-thiazol-5-yl]-2-pyridyl]benzamide (Example compound 16-9), N-[4-[2-butyl-4-(3-methylphenyl)-1,3-thiazol-5-yl]-2-pyridyl]-3-phenylpropionamide (Example compound 16-10), N-[4-[2-(4-fluorophenyl)-4-(3-methylphenyl)-1,3-thiazol-5-yl]-2-pyridyl]benzamide (Example compound 16-11), N-[4-[2-(4-fluorophenyl)-4-(3-methylphenyl)-1,3-thiazol-5-yl]-2-pyridyl]-3-phenylpropionamide (Example compound 16-12), N-[4-[4-(3-methylphenyl)-2-(4-methylthiophenyl)-1,3-thiazol-5-yl]-2-pyridyl]benzamide (Example compound 16-15), N-[4-[4-(3-methylphenyl)-2-(4-methylthiophenyl)-1,3-thiazol-5-yl]-2-pyridyl]-3-phenylpropionamide (Example compound 16-16), N-benzyl-N-[4-[2-ethyl-4-(3-methylphenyl)-1,3-thiazol-5-yl]-2-pyridyl]amine (Example compound 19-2), N-[4-[2-ethyl-4-(3-methylphenyl)-1,3-thiazol-5-yl]-2-pyridyl]N-(2-phenylethyl)amine (Example compound 19-3), N-[4-[2-ethyl-4-(3-methylphenyl)-1,3-thiazol-5-yl]-2-pyridyl]-N-(3-phenylpropyl)amine (Example compound 19-4), N-benzyl-N-[4-[4-(3-methylphenyl)-2-propyl-1,3-thiazol-5-yl]-2-pyridyl]amine (Example compound 19-5), N-[4-[4-(3-methylphenyl)-2-propyl-1,3-thiazol-5-yl]-2-pyridyl]-N-(2-phenylethyl)amine (Example compound 19-6), N-[4-[4-(3-methylphenyl)-2-propyl-1,3-thiazol-5-yl]-2-pyridyl]-N-(3-phenylpropyl)amine (Example compound 19-7), N-benzyl-N-[4-[2-butyl-4-(3-methylphenyl)-1,3-thiazol-5-yl]-2-pyridyl]amine (Example compound 19-8), N-[4-[2-butyl-4-(3-methylphenyl)-1,3-thiazol-5-yl]-2-pyridyl]-N-(2-phenylethyl)amine (Example compound 19-9), N-[4-[2-butyl-4-(3-methylphenyl)-1,3-thiazol-5-yl]-2-pyridyl]-N-(3-phenylpropyl)amine (Example compound 19-10), N-benzyl-N-[4-[4-(3-methylphenyl)-2-(4-methylthiophenyl)-1,3-thiazol-5-yl]-2-pyridyl]amine (Example compound 19-17), N-[4-[4-(3-methylphenyl)-2-(4-methylthiophenyl)-1,3-thiazol-5-yl]-2-pyridyl]-N-(2-phenylethyl)amine (Example compound 19-18), N-[4-[4-(3-methylphenyl)-2-(4-methylthiophenyl)-1,3-thiazol-5-yl]-2-pyridyl]-N-(3-phenylpropyl)amine (Example compound 19-19), N-[4-[4-(3-methylphenyl)-2-(4-methylsulfonylphenyl)-1,3-thiazol-5-yl]-2-pyridyl]benzamide (Example compound 20), N-[4-[4-(3-methylphenyl)-2-(4-methylsulfonylphenyl)-1,3-thiazol-5-yl]-2-pyridyl]phenylacetamide (Example compound 21-1), N-[4-[4-(3-methylphenyl)-2-(4-methylsulfonylphenyl)-1,3-thiazol-5-yl]-2-pyridyl]-3-phenylpropionamide (Example compound 21-2), N-benzyl-N-[4-[4-(3-methylphenyl)-2-(4-methylsulfonylphenyl)-1,3-thiazol-5-yl]-2-pyridyl]amine (Example compound 21-5), N-[4-[4-(3-methylphenyl)-2-(4-methylsulfonylphenyl)-1,3-thiazol-5-yl]-2-pyridyl]-N-(3-phenylpropyl)amine (Example compound 21-6), N-[4-[4-(3-methylphenyl)-2-(4-methylsulfonylphenyl)-1,3-thiazol-5-yl]-2-pyridyl]-N-(2-phenylethyl)amine (Example compound 25-1), N-(4-fluorobenzyl)-N-[4-[4-(3-methylphenyl)-2-(4-methylsulfonylphenyl)-1,3-thiazol-5-yl]-2-pyridyl]amine (Example compound 25-2).

[18] Compound (Ij)

An optionally N-oxidized compound represented by the formula:

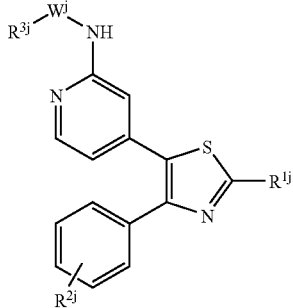

(Ij)

wherein $W^j$ is a bond, a divalent hydrocarbon group optionally having substituent(s), $R^{1j}$ is a hydrogen atom, a hydrocarbon group optionally having substituent(s), a heterocyclic group optionally having substituent(s), an amino group optionally having substituent(s) or an acyl group, $R^{2j}$ is a hydrogen atom or substituent, and $R^{3j}$ is a hydrocarbon group optionally having substituent(s) or a heterocyclic group optionally having substituent(s).

As the substituent denoted by $R^{2j}$, those similar to the "substituent" of the aforementioned "aromatic group optionally having substituent(s)" are used.

As $R^{1j}$, an amino group optionally having substituent(s), an alkyl group optionally having substituent(s), a heterocyclic group optionally having substituent(s) and the like are preferable.

As the "amino group optionally having substituent(s)", an amino group optionally having one or two acyl groups represented by the formula: —(C=O)—$R^7$, —(C=O)—$OR^7$, —(C=O)—$NR^7R^8$, —(C=S)—$NHR^7$ or —$SO_2$—$R^9$ wherein each symbol is as defined above, is more preferable. An amino group optionally having one or two acyl represented by the formula: —(C=O)—$R^7$ wherein each symbol is as defined above, is particularly preferable.

As the "alkyl group optionally having substituent(s)", for example, $C_{1-6}$ alkyl group (e.g., methyl, ethyl, propyl, isopropyl, butyl, isobutyl, sec-butyl, tert-butyl and the like) optionally substituted by 1 to 3 substituents selected from halogen atom, $C_{1-6}$ alkoxy, hydroxy, carboxy, $C_{1-6}$ alkoxycarbonyl and the like, and the like are preferable, and $C_{1-3}$ alkyl group such as methyl, ethyl, propyl and the like are particularly preferable.

As the "heterocyclic group optionally having substituent(s)", for example, preferably, 5- to 10-membered non-aromatic heterocyclic group (e.g., pyrrolidinyl, imidazolyl, pyrazolidyl, pyrazolyl, piperidinyl, piperazinyl, morpholyl, thiomorpholyl, dioxazolyl, oxadiazolyl, thiadiazolyl, triazolyl, thiadiazolyl, dithiazolyl and the like, more preferably, a 5- or 6-membered non-aromatic nitrogen-containing heterocyclic group such as piperidinyl (e.g., 4-piperidinyl etc.) and the like, which optionally has substituent(s) such as $C_{1-6}$ alkyl (e.g., $C_{1-4}$ alkyl such as methyl, ethyl, propyl, butyl etc., and the like), and the like can be mentioned.

Of these, as the $R^{1j}$, (i) an amino group, (ii) an amino group having 1 or 2 acyl groups represented by the formula: —(C=O)—$R^{7j}$ wherein $R^{7j}$ is a 5- to 14-membered heterocyclic group containing, besides carbon atom(s), 1 or 2 kinds of 1 to 4 hetero atoms selected from nitrogen atom, sulfur atom and oxygen atom (e.g., a 5- or 6-membered heterocyclic group containing, besides carbon atom(s), 1 or 2 hetero atoms selected from nitrogen atom, sulfur atom and oxygen atom, such as pyridyl group and the like, etc.), which is optionally substituted by a halogen atom (preferably chlorine atom), (iii) $C_{1-6}$ alkyl group (preferably $C_{1-3}$ alkyl group such as methyl, ethyl, propyl and the like), (iv) a 5- to 10-membered non-aromatic heterocyclic group optionally substituted by $C_{1-6}$ alkyl (preferably $C_{1-3}$ alkyl such as methyl, ethyl, propyl and the like) and the like (preferably a 5- or 6-membered non-aromatic nitrogen-containing heterocyclic group, such as piperidinyl (e.g., 4-piperidinyl etc.) and the like, and the like are preferable.

As $R^{2j}$, halogen atom (e.g., chlorine atom, fluorine atom etc.), $C_{1-6}$ alkyl group (preferably $C_{1-3}$ alkyl group such as methyl, ethyl, propyl and the like), $C_{1-6}$ alkoxy (e.g., methoxy etc.) and the like are preferable, and halogen atom (e.g., chlorine atom, fluorine atom etc.), $C_{1-6}$ alkyl group (preferably $C_{1-3}$ alkyl group such as methyl, ethyl, propyl, isopropyl and the like) are particularly preferable.

As $R^{3j}$, (i) $C_{1-6}$ alkyl group, (ii) $C_{3-8}$ cycloalkyl group (e.g., cyclopentyl, cyclohexyl and the like) optionally substituted by halogen atom (e.g., chlorine atom, fluorine atom and the like), $C_{1-6}$ alkyl (e.g., methyl, ethyl and the like) or $C_{1-6}$ alkoxy (e.g., methoxy, ethoxy and the like), (iii) $C_{6-14}$ aryl group (e.g., phenyl group and the like) optionally substituted by halogen atom (e.g., chlorine atom, fluorine atom and the like), $C_{1-6}$ alkyl (e.g., methyl, ethyl and the like) or $C_{1-6}$ alkoxy (e.g., methoxy, ethoxy and the like), (iv) a 5- or 6-membered heterocyclic group (e.g., thienyl group and the like) containing, besides carbon atom(s), 1 or 2 kinds of 1 to 4 hetero atoms selected from nitrogen atom, sulfur atom and oxygen atom, which is optionally substituted by halogen atom (e.g., chlorine atom, fluorine atom and the like), $C_{1-6}$ alkyl (e.g., methyl, ethyl and the like), $C_{1-6}$ alkoxy (e.g., methoxy, ethoxy and the like), and the like are preferable of these, (i) $C_{1-6}$ alkyl group (preferably $C_{1-3}$ alkyl group such as methyl, ethyl, propyl and the like), (ii) $C_{3-8}$ cycloalkyl group (e.g., cyclopentyl, cyclohexyl and the like), (iii) $C_{6-14}$ aryl group (e.g., phenyl group and the like), (iv) a 5- or 6-membered heterocyclic group (e.g., thienyl group and the like) containing, besides carbon atom(s), 1 or 2 kinds of 1 to 4 hetero atoms selected from nitrogen atom, sulfur atom and oxygen atom, and the like are preferable.

As $W^j$, a bond or $C_{1-6}$ alkylene optionally substituted by oxo is preferable. Particularly, a bond, —$(CH_2)_n$— (n is an integer of 1-3), —$(CH_2)_nCO$— (n is an integer of 0-3) and the like are preferable, and a bond, —CO—, —$CH_2CO$—, —$CH(CH_3)$— and the like are particularly preferable.

Particularly, Reference Example compounds 32 to 45 and 62 to 74 shown in Tables 1 and 2 are preferable.

[19] Compound (Ik)

An optionally N-oxidized compound represented by the formula:

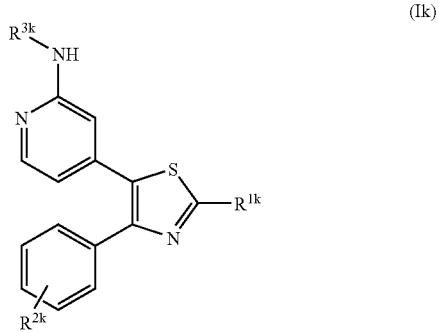

(Ik)

wherein $R^{1k}$ is a hydrogen atom, a hydrocarbon group optionally having substituent(s), a heterocyclic group optionally having substituent(s), an amino group optionally having substituent(s) or an acyl group, $R^{2k}$ is a hydrogen atom or substituent, and $R^{3k}$ is a cyclic hydrocarbon group optionally having substituent(s) or a heterocyclic group optionally having substituent(s).

As the substituent denoted by $R^{2k}$, those similar to the "substituent" of the aforementioned "aromatic group optionally having substituent(s)" are used.

As $R^{1k}$, an amino group optionally having substituent(s) and alkyl group optionally having substituent(s), aryl group optionally having substituent(s) and the like are preferable.

As the "amino group optionally having substituent(s)", an amino group optionally having one or two acyl groups represented by the formula: —(C═O) —$R^7$, —(C═O)—$OR^7$, —(C═O)—$NR^7R^8$, —(C═S)—$NHR^7$ or —$SO_2$—$R^9$ wherein each symbol is as defined above, is more preferable. An amino group optionally having one or two acyl groups represented by the formula: —(C═O)—$R^7$ wherein each symbol is as defined above, is particularly preferable.

As the "alkyl group optionally having substituent(s)", for example, $C_{1-6}$ alkyl group (e.g., methyl, ethyl, propyl, isopropyl, butyl, isobutyl, sec-butyl, tert-butyl and the like) optionally substituted by 1 to 3 substituents selected from halogen atom, $C_{1-6}$ alkoxy, hydroxy, carboxy and $C_{1-6}$ alkoxy-carbonyl and the like is preferable, and $C_{1-3}$ alkyl groups such as methyl, ethyl, propyl and the like are particularly preferable.

Of these, as $R^{1k}$, (i) an amino group, (ii) an amino group having one or two acyl represented by the formula: —(C═O)—$R^{7k}$ wherein $R^{7k}$ is a 5 to 14-membered heterocyclic group containing, besides carbon atom(s), 1 or 2 kinds of 1 to 4 hetero atoms selected from nitrogen atom, sulfur atom and oxygen atom (e.g., a 5- or 6-membered heterocyclic group containing, besides carbon atom(s), 1 or 2 hetero atoms selected from nitrogen atom, sulfur atom and oxygen atom, such as pyridyl group and the like, and the like), which is optionally substituted by a halogen atom (preferably chlorine atom) or (iii) $C_{1-6}$ alkyl group (preferably $C_{1-3}$ alkyl group such as methyl, ethyl, propyl and the like), and the like are preferable.

As $R^{2k}$, a halogen atom (e.g., chlorine atom, fluorine atom, iodine and the like), $C_{1-6}$ alkyl group (preferably $C_{1-3}$ alkyl group such as methyl, ethyl, propyl and the like), $C_{1-6}$ alkoxy (e.g., methoxy and the like) and the like are preferable, particularly, halogen atom (preferably fluorine atom, chlorine atom), $C_{1-6}$ alkyl group (preferably $C_{1-3}$ alkyl group such as methyl, ethyl, propyl and the like) are preferable.

As $R^{3k}$, $C_{3-8}$ cycloalkyl group (e.g., cyclopentyl, cyclohexyl and the like) or $C_{6-14}$ aryl group (e.g., phenyl group and the like) optionally substituted by a halogen atom (e.g., chlorine atom, fluorine atom and the like), $C_{1-6}$ alkyl (e.g., methyl, ethyl and the like), $C_{1-6}$ alkoxy (e.g., methoxy, ethoxy and the like), and the like are preferable, and unsubstituted $C_{3-8}$ cycloalkyl group (e.g., cyclopentyl, cyclohexyl and the like) and the like are preferable.

Particularly, Reference Example compounds 32-1, 32-2, 33, 42, 43 and 62 to 69-3, 74 shown in Tables 1 and 2 are referable.

[20] Compound (IL)

An optionally N-oxidized compound represented by the formula:

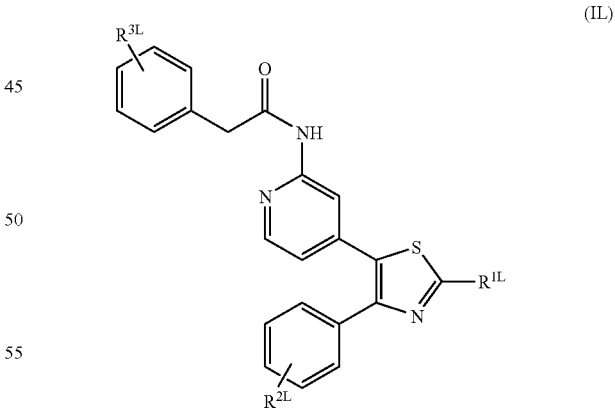

(IL)

wherein $R^{1L}$ is a hydrogen atom, a hydrocarbon group optionally having substituent(s), a heterocyclic group optionally having substituent(s), an amino group optionally having substituent(s) or an acyl group, $R^{2L}$ is a hydrogen atom or substituent, and $R^{3L}$ is a hydrogen atom or substituent.

As the substituent denoted by $R^2L$, those similar to the "substituent" of the aforementioned "aromatic group optionally having substituent(s)" are used.

As the substituent denoted by $R^{3L}$, those similar to the "substituent" of the aforementioned "hydrocarbon group optionally having substituent(s)" are used.

As $R_{1L}$, alkyl group optionally having substituent(s) and the like are preferable. For example, $C_{1-6}$ alkyl group (e.g., methyl, ethyl, propyl, isopropyl, butyl, isobutyl, sec-butyl, tert-butyl and the like) optionally substituted by 1 to 3 substituents selected from halogen atom, $C_{1-6}$ alkoxy, hydroxy, carboxy, $C_{1-6}$ alkoxy-carbonyl and the like are preferable. Particularly, $C_{1-3}$ alkyl group such as methyl, ethyl, propyl, isopropyl and the like are preferable.

As $R^{2L}$, halogen atom (e.g., chlorine atom, fluorine atom and the like), $C_{1-6}$ alkyl group (preferably $C_{1-3}$ alkyl group such as methyl, ethyl, propyl and the like), $C_{1-6}$ alkoxy (e.g., methoxy and the like) and the like are preferable, particularly halogen atom (e.g., chlorine atom, fluorine atom and the like), and $C_{1-6}$ alkyl group (preferably $C_{1-3}$ alkyl group such as methyl, ethyl, propyl and the like) are preferable.

As $R^{2L}$, $C_{6-14}$ aryl group (e.g., phenyl group and the like) optionally substituted by halogen atom (e.g., chlorine atom, fluorine atom and the like), $C_{1-6}$ alkyl (e.g., methyl, ethyl and the like), $C_{1-6}$ alkoxy (e.g., methoxy, ethoxy and the like), and the like are preferable. Particularly, unsubstituted $C_{6-14}$ aryl group (e.g., phenyl group and the like) and the like are preferable.

Particularly, Reference Example compounds 35, 37-1, 37-2, 37-3, 37-4, 37-5, 40-1, 40-2 and 68-1 to 68-10 shown in Tables 1 and 2 are preferable.

[21] Compound (Im)

An optionally N-oxidized compound represented by the formula:

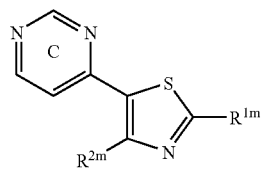

(Im)

wherein
ring C is a 4-pyrimidinyl group optionally having substituent(s),
$R^{1m}$ is a hydrogen atom, a hydrocarbon group optionally having substituent(s), a heterocyclic group optionally having substituent(s), an amino group optionally having substituent(s) or an acyl group, and
$R^{2m}$ is an aromatic group optionally having substituent(s).

[22] Compound (In)

An optionally N-oxidized compound represented by the formula:

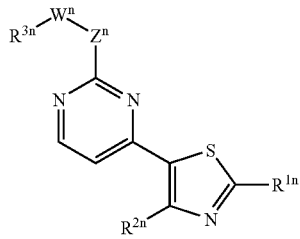

(In)

wherein
$Z^n$ is a bond, —$NR^{4n}$— ($R^{44n}$ is a hydrogen atom or a hydrocarbon group optionally having substituent(s)), an oxygen atom or an optionally oxidized sulfur atom, $W^n$ is a bond or a divalent hydrocarbon group optionally having substituent(s),
$R^{1n}$ is a hydrogen atom, a hydrocarbon group optionally having substituent(s), a heterocyclic group optionally having substituent(s), an amino group optionally having substituent(s) or an acyl group,
$R^{2n}$ is an aromatic group optionally having substituent(s), and
$R^{3n}$ is a hydrogen atom, a hydrocarbon group optionally having substituent(s) or a heterocyclic group optionally having substituent(s).

Of the above-mentioned compound (If), (Ig) and (Ih), compounds (If'), (Ig') and (Ih') wherein Y is a nitrogen atom are novel compounds.

As the salt of Compound (I), for example, a metal salt, an ammonium salt, a salt with an organic base, a salt with an inorganic acid, a salt with an organic acid, a salt with a basic or acidic amino acid and the like can be mentioned. As examples of suitable metal salt, alkali metal salts such as sodium salt, potassium salt and the like; alkaline earth metal salts such as calcium salt, magnesium salt, barium salt and the like; aluminum salt and the like can be mentioned. As a suitable example of a salt with an organic base, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine etc., and the like can be mentioned. As a suitable example of the salt with an inorganic acid, for example, salts with hydrochloric acid, hydrobromic acid, nitric acid, sulfuric acid, phosphoric acid etc., and the like can be mentioned. As a suitable example of the salt with an organic acid, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid etc., and the like can be mentioned. As a suitable example of the salt with a basic amino acid, for example, salts with arginine, lysine, ornithine etc., and the like can be mentioned. As a suitable example of the salt with an acidic amino acid, for example, salts with aspartic acid, glutamic acid etc., and the like can be mentioned.

Of these, pharmaceutically acceptable salts are preferable. For example, when a compound has an acidic functional group therein, inorganic salts such as alkali metal salts (e.g., sodium salt, potassium salt and the like), alkaline earth metal salts (e.g., calcium salt, magnesium salt, barium salt and the like), and the like, ammonium salts and the like can be mentioned, and when a compound has a basic functional group therein, salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like, and the like can be mentioned.

The production methods of compound (I) of the present invention and a salt thereof are explained in the following.

Compound (I) includes Compounds (I'), (I''), (Ia) [including (Ia'), (Ia'') and (Ia''')], (Ib), (Ic), (Id), (Ie), (If) [including (If')], (Ig) [including (Ig')], (Ih) [including (Ih')], (Ii), (Ij), (Ik), (IL), (Im) and (In), except the compound described in the above-mentioned reference (WO01/91749).

For example, Compound (I) of the present invention wherein ring B is an imidazole ring can be obtained by the methods described in WO98/56788, WO99/1130, WO99/1131, WO99/61437, WO00/26209, WO00/63204 and the like or a method analogous thereto and the like. A compound wherein ring B is an oxazole ring can be obtained by the methods described in WO00/63204 and the like or a method analogous thereto, a compound wherein ring B is a thiazole ring can be obtained by the methods described in JP-A-S60-58981, JP-A-S61-10580, JP-A-H5-70446, JP-T-H7-503023, DE-A-3601411, WO93/15071, WO00/64894 and the like or a method analogous thereto and the like. A compound wherein ring B is a pyrazole ring can be obtained by the methods described in WO98/52940, WO00/31063, WO99/39116 and the like or a method analogous thereto and the like, and a compound wherein ring B is an isoxazole ring can be obtained by the method described in JP-A-2000-86657 or a method analogous thereto and the like, and a compound wherein ring B is a pyrrole ring can be obtained by the methods described in WO97/5877 and WO99/43680 or a method analogous thereto and the like.

The production methods of novel Compound (Im) (including (In), (If'), (Ig'), (Ih'), and the following compounds (Io), (Ip)), or a salt thereof of the present invention are explained in the following.

Compound (Im) can be obtained by the methods employed for the synthesis of the above-mentioned Compound (I) or a method analogous thereto and the like, as well as a method shown in the following Reaction Schemes 1, 2 and 3 or a method analogous thereto and the like. Here, the production method of Compound (Im) is briefly described.

Compound (Im) or a salt thereof can be produced by a method characterized by reacting a compound represented by the formula:

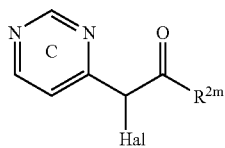

wherein ring C is a 4-pyrimidinyl group optionally having substituent(s),

Hal is a halogen, and $R^{2m}$ is an aromatic group optionally having substituent(s), or a salt thereof with a compound represented by the formula:

$R^{1m}CSNH_2$ wherein $R^{1m}$ is a hydrogen atom, a hydrocarbon group optionally having substituent(s), a heterocyclic group optionally having substituent(s), an amino group optionally having substituent(s) or an acyl group [as regards compound $R^{1m}CSNH_2$, refer to compound (VII) appearing below in the present specification] or a salt thereof (see Reaction Schemes 1, 2, 3 and 4 below for the detail).

Respective symbols in the compounds in Reaction Schemes 1, 2, 3 and 4 are as defined above. The compounds in Reaction Schemes may form a salt, and as the salt, for example, those similar to the salt of Compound (I), and the like can be mentioned. For Compound (II), (III), (IV), (X), (XI), (XV), (XVI), (XVIII) and (XIX), commercially available compounds can be used, or can be produced according to a method known per se or a method analogous thereto.

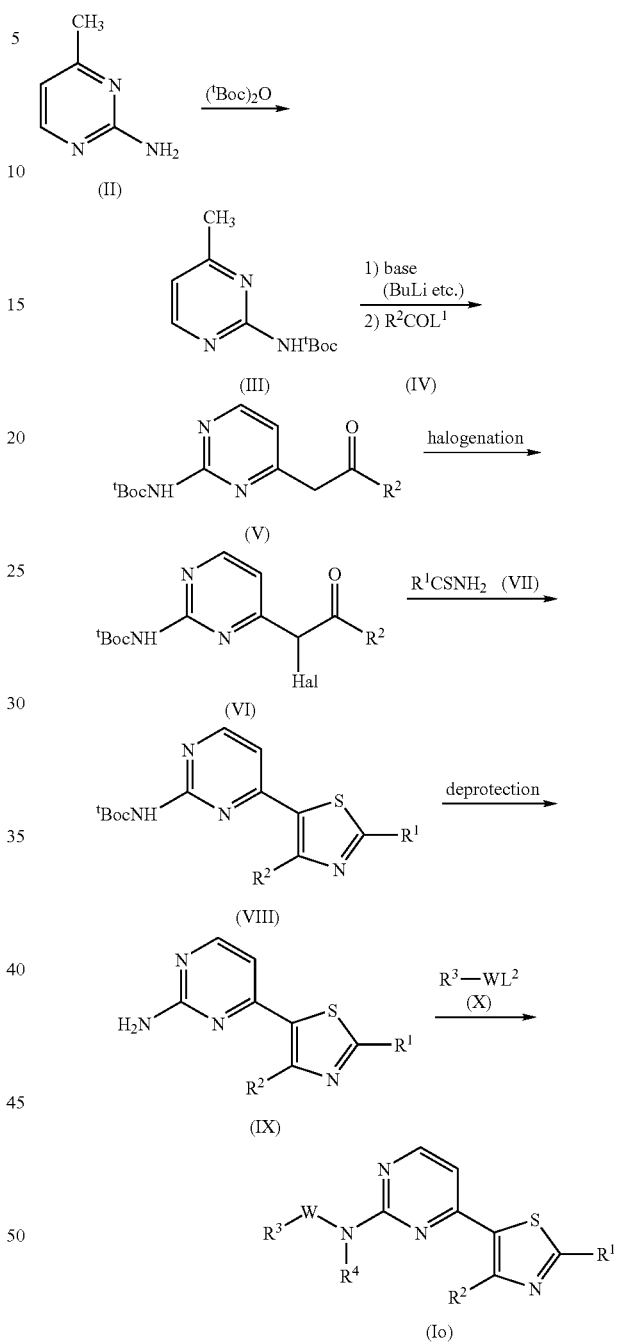

In the following, $L^1$, $L^2$, and $L^3$ (Reaction Scheme 2) each denote a leaving group. The "leaving group" denoted by $L^1$, $L^2$ and $L^3$ is, for example (1) $C_{1-6}$ alkoxy (e.g., methoxy, ethoxy etc.), (2) di-$C_{1-6}$ alkylamino (e.g., dimethylamino, diethylamino etc.), (3) N—$C_{6-10}$ aryl-N—$C_{1-6}$ alkylamino (e.g., N-phenyl-N-methylamino etc.), (4) 3 to 7-membered cyclic amino (e.g., pyrrolidino, morpholino, methylaziridin- 1-yl etc.) optionally substituted by $C_{6-10}$ aryl and/or $C_{1-6}$ alkyl, (5) N-$C_{1-6}$ alkyl-N-$C_{1-6}$ alkoxyamino (N-methoxy-N-methylamino etc.) and the like, (6) hydroxy, (7) halogen atom (e.g., fluorine, chlorine, bromine, iodine etc.), (8) optionally halogenated $C_{1-5}$ alkylsulfonyloxy (e.g., methanesulfonyloxy, ethanesulfonyloxy, trifluoromethanesulfonyloxy etc.), (9) $C_{6-10}$ arylsulfonyloxy optionally having substituent(s), (10) optionally halogenated $C_{1-5}$ alkylsulfonyl (e.g., methanesulfonyl, ethanesulfonyl, trifluoromethanesulfonyl etc.), (11) $C_{6-10}$ arylsulfonyl optionally having substituent(s) and the like can be mentioned.

As the "$C_{6-10}$ arylsulfonyloxy optionally having substituent(s)", for example, $C_{6-10}$ arylsulfonyloxy (e.g., phenylsulfonyloxy, naphthylsulfonyloxy etc.) optionally having 1 to 3 substituent(s) selected from $C_{1-6}$ alkyl, $C_{1-6}$ alkoxy and nitro, and the like can be mentioned. As specific examples, benzenesulfonyloxy, m-nitrobenzenesulfonyloxy, p-toluenesulfonyloxy and the like can be mentioned.

As the "$C_{6-10}$ arylsulfonyl optionally having substituent(s)", for example, $C_{6-10}$ arylsulfonyl (e.g., phenylsulfonyl, naphthylsulfonyl etc.) optionally having 1 to 3 substituent(s) selected from $C_{1-6}$ alkyl, $C_{1-6}$ alkoxy and nitro, and the like can be mentioned. As specific examples, benzenesulfonyl, m-nitrobenzenesulfonyl, p-toluenesulfonyl and the like can be mentioned.

Compound (III) is obtained by protecting Compound (II) with di-t-butyl dicarbonate.

The amount of di-t-butyl dicarbonate to be used is about 0.8 to about 5 moles, preferably about 1 to about 1.5 moles, per 1 mole of Compound (II).

It is advantageous to carry out this reaction without a solvent or in the presence of an inert solvent for the reaction. The solvent is not particularly limited as long as the reaction proceeds, but, for example, aromatic hydrocarbons, ethers, alcohols, esters or a mixture of two or more of them and the like are used.

The reaction temperature is usually about 0 to about 100° C., preferably about 0 to about 60° C. The reaction time is usually about 5 minutes to about 48 hours, preferably about 1 hour to about 24 hours.

Although the product can be used as a reaction solution itself or as a crude product in the next reaction, it can be isolated from the reaction mixture by a conventional method, and can be easily purified by a separating methods such as recrystallization, distillation, chromatography and the like.

To obtain Compound (V), Compound (III) is treated with a base, followed by condensing with Compound (IV).

The amount of base to be used is about 0.8 to about 5 moles, preferably about 2 to about 2.5 moles, per 1 mole of Compound (III).

As the "base" for example, alkyl lithiums such as n-butyl lithium and the like, and metal amides such as sodium amide, lithium diisopropylamide, lithium hexamethyldisilazide and the like are used.

It is advantageous to carry out this reaction without a solvent or in the presence of an inert solvent for the reaction. The solvent is not particularly limited as long as the reaction proceeds, but, for example, aliphatic hydrocarbons, aromatic hydrocarbons, ethers or a mixture of two or more of them and the like are used.

The reaction temperature is usually about −78 to about 60° C., preferably about −78 to about 20° C. The reaction time is usually about 5 minutes to about 24 hours, preferably about 0.5 hour to about 3 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (VI) can be obtained by treating Compound (V) with a halogen or metal halide. Where desired, this reaction is carried out in the presence of a base or a basic salt.

As the "halogen", chlorine, bromine, iodine and the like can be mentioned.

As the "metal halide", copper halides such as copper(II) bromide, copper(II) chloride and the like can be mentioned.

Accordingly, in Compound (VI), Hal methods halogen such as chlorine, bromine, iodine and the like.

The amount of halogen or metal halide to be used is about 1 to about 5 moles, preferably about 1 to about 2 moles, per 1 mole of compound (V).

The amount of a base to be used is about 1 to about 10 moles, preferably about 1 to about 3 moles, per 1 mole of Compound (V).

As the "base", for example, metal hydroxides such as sodium hydroxide, potassium hydroxide, lithium hydroxide and the like, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, ethers, esters, aromatic hydrocarbons, aliphatic hydrocarbons, amides, halogenated hydrocarbons, nitriles, sulfoxides, organic acids, aromatic amines or a mixture of two or more of them and the like are used.

The reaction temperature is about −20 to about 150° C., preferably about 0 to about 100° C. The reaction time is usually about 0.5 minutes to about 24 hours, preferably about 10 minutes to about 5 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (VIII) can be obtained by condensing Compound (VI) with Compound (VII). This reaction is performed optionally in the presence of a base.

When Compound (VII) is commercially available, it can be used as it is, or is obtained by a method known per se or a method according to a known method, or further by a method shown by the following Reaction Scheme 4.

The amount of Compound (VII) to be used is about 0.5 to about 3 moles, preferably about 0.8 to about 2 moles, per 1 mole of Compound (VI).

The amount of a base to be used is about 1 to about 30 moles, preferably about 1 to about 10 moles, per 1 mole of Compound (VI).

As the "base", for example, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N- dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, ethers, amides, alcohols, nitriles or a mixture of two or more of them and the like are used.

The reaction temperature is about −5 to about 200° C., preferably about 5 to about 150° C. The reaction time is usually about 5 minutes to about 72 hours, preferably about 0.5 to about 30 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (IX) is obtained by deprotecting Compound (VIII) using an acid or a base.

The amount of an acid or a base to be used is about 0.1 to about 50 moles, preferably about 1 to about 20 moles, per 1 mole of Compound (VIII).

As the "acid", for example, mineral acids such as hydrochloric acid, hydrobromic acid, sulfuric acid and the like, Lewis acids such as boron trichloride, boron tribromide and the like, the use of Lewis acid together with thiols or sulfides, organic acids such as trifluoroacetic acid, p-toluenesulfonic acid and the like, and the like are used.

As the "base", for example, metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like, and the like are used.

It is advantageous to carry out this reaction without a solvent or in the presence of an inert solvent for the reaction. The solvent is not particularly limited as long as the reaction proceeds, but, for example, alcohols, ethers, aromatic hydrocarbons, aliphatic hydrocarbons, halogenated hydrocarbons, sulfoxides, water or a mixture of two or more of them and the like are used.

The reaction time is usually about 10 minutes to about 50 hours, preferably about 30 minutes to about 12 hours. The reaction temperature is usually about 0 to about 200° C., preferably about 20 to about 120° C.

Compound (Io) can be obtained by condensing Compound (IX) with Compound (X) optionally in the presence of a base.

The amount of Compound (XVIII) to be used is about 0.8 to about 5 moles, preferably about 1 to about 3 moles, per 1 mole of Compound (XVII).

The amount of the base to be used is about 0.1 to about 5 moles, preferably about 0.8 to about 2.5 moles, per 1 mole of Compound (XVII).

As the "base", for example, basic salts such as sodium carbonate, potassium carbonate, cesium carbonate, sodium acetate and the like, metal hydroxides such as sodium hydroxide, potassium hydroxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned.

It is advantageous to carry out this reaction without a solvent or in the presence of an inert solvent for the reaction. The solvent is not particularly limited as long as the reaction proceeds, but, for example, aliphatic hydrocarbons, aromatic hydrocarbons, ethers, amides or a mixture of two or more of them and the like are used.

The reaction temperature is usually about −78 to about 100° C., preferably about −78 to about 70° C. The reaction time is usually about 5 minutes to about 24 hours, preferably about 0.5 to about 20 hours.

Although the product can be used as a reaction solution itself or as a crude product in the next reaction, it can be isolated from the reaction mixture by a conventional method, and can be easily purified by a separating methods such as recrystallization, distillation, chromatography and the like. Thereafter, compounds wherein $R^4$ is other than hydrogen atom can be synthesized by performing alkylation or acylation and the like, if desired.

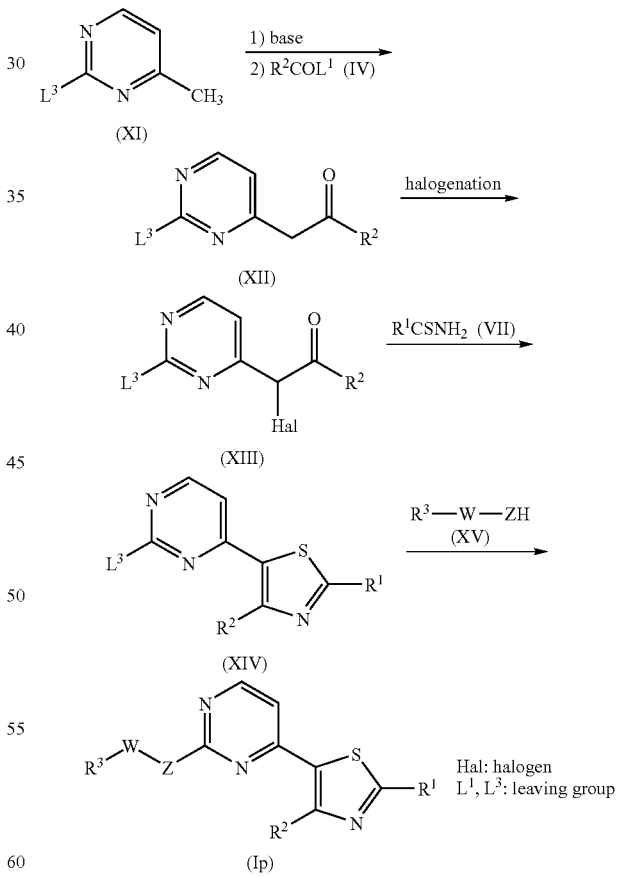

Compound (XII) can be obtained by treating Compound (XI) with a base and condensing Compound (IV).

The amount of the base to be used is about 0.8 to about 3 moles, preferably about 1 to about 1.2 moles, per 1 mole of compound (XI).

As the "base", for example, metal amides such as sodium amide, lithium diisopropylamide, lithium hexamethyldisilazide and the like are used.

It is advantageous to carry out this reaction without a solvent or in the presence of an inert solvent for the reaction. The solvent is not particularly limited as long as the reaction proceeds, but, for example, aliphatic hydrocarbons, aromatic hydrocarbons, ethers or a mixture of two or more of them and the like are used.

The reaction temperature is usually about −78 to about 60° C., preferably about −78 to about 20° C. The reaction time is usually about 5 minutes to about 24 hours, preferably about 0.5 to about 3 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (XIII) can be obtained by treating Compound (XII) with a halogen or metal halides. Where desired, this reaction is carried out in the presence of a base or a basic salt.

As the "halogen", chlorine, bromine, iodine and the like can be mentioned.

As the "metal halide", copper halides such as copper(II) bromide, copper(II) chloride and the like can be mentioned.

Accordingly, in compound (XIII), Hal methods halogen such as chlorine, bromine, iodine and the like.

The amount of halogen or metal halide to be used is about 1 to about 5 moles, preferably about 1 to about 2 moles, per 1 mole of compound (XIII).

The amount of the base to be used is about 1 to about 10 moles, preferably about 1 to about 3 moles, per 1 mole of Compound (XII).

As the "base", for example, metal hydroxides such as sodium hydroxide, potassium hydroxide, lithium hydroxide, barium hydroxide and the like, basic salts such as sodium carbonate, potassium carbonate, cesium carbonate, sodium hydrogen carbonate, sodium acetate and the like, aromatic amines such as pyridine, lutidine and the like, tertiary amines such as a triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, ethers, esters, aromatic hydrocarbons, aliphatic hydrocarbons, amides, halogenated hydrocarbons, nitrites, sulfoxides, organic acids, aromatic amines or a mixture of two or more of them and the like are used.

The reaction temperature is about −20 to about 150° C., preferably about 0 to about 100° C. The reaction time is usually about 5 minutes to about 24 hours, preferably about 10 minutes to about 5 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (XIV) can be obtained by condensing Compound (XIII) with Compound (VII). Where desired, this reaction is carried out in the presence of a base.

The amount of Compound (VII) to be used is about 0.5 to about 3 moles, preferably about 0.8 to about 2 moles, per 1 mole of Compound (XIII).

The amount of the base to be used is about 1 to about 30 moles, preferably about 1 to about 10 moles, per 1 mole of compound (XIII).

As the "base", for example, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, ethers, amides, alcohols, nitrites or a mixture of two or more of them and the like are used.

The reaction temperature is about −5 to about 200° C., preferably about 5 to about 150° C. The reaction time is usually about 5 minutes to about 72 hours, preferably about 0.5 hour to about 30 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (Ip) can be obtained by condensing Compound (XIV) with Compound (XV).

Where desired, this reaction is carried out in the presence of a base.

The amount of Compound (XV) to be used is about 1 to about 100 moles, preferably about 1 to about 30 moles, per 1 mole of Compound (XIV).

As the "base", for example, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like, and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, ethers, sulfoxides, alcohols, nitrites, ketones or a mixture of two or more of them and the like are used.

The reaction temperature is about −5 to about 200° C., preferably about 5 to about 120° C. The reaction time is usually about 5 minutes to about 72 hours, preferably about 0.5 hour to about 30 hours.

Although the product can be used as a reaction solution itself or as a crude product in the next reaction, it can be isolated from the reaction mixture by a conventional method, and can be easily purified by a separating methods such as recrystallization, distillation, chromatography and the like.

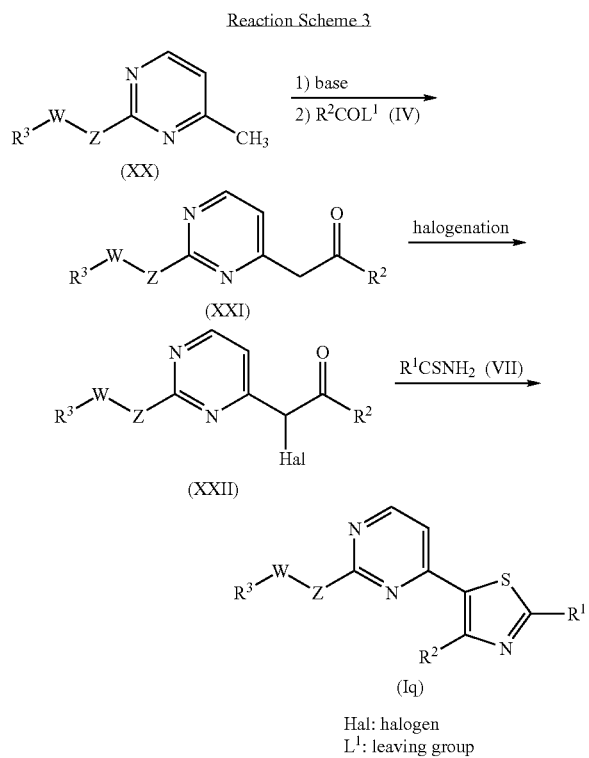

Reaction Scheme 3

Hal: halogen
L¹: leaving group

Compound (XXI) can be obtained by treating Compound (XX) with a base and condensing Compound (IV).

The amount of the base to be used is about 0.8 to about 3 moles, preferably about 1 to about 1.2 moles, per 1 mole of Compound (XX).

As the "base", for example, metal amides such as sodium amide, lithium diisopropylamide, lithium hexamethyldisilazide and the like are used.

It is advantageous to carry out this reaction without a solvent or in the presence of an inert solvent for the reaction. The solvent is not particularly limited as long as the reaction proceeds, but, for example, aliphatic hydrocarbons, aromatic hydrocarbons, ethers or a mixture of two or more of them and the like are used.

The reaction temperature is usually about −78 to about 60° C., preferably about −78 to about 20° C. The reaction time is usually about 5 minutes to about 24 hours, preferably about 0.5 to about 3 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (XXII) can be obtained by treating Compound (XXI) with halogen or metal halide. Where desired, this reaction is carried out in the presence of a base or a basic salt.

As the "halogen", chlorine, bromine, iodine and the like can be mentioned.

As the "metal halide", copper halide such as copper(II) bromide, copper(II) chloride and the like can be mentioned.

Accordingly, Hal in Compound (XXII) methods halogen such as chlorine, bromine, iodine and the like.

The amount of the halogen or metal halide to be used is about 1 to about 5 moles, preferably about 1 to about 2 moles, per 1 mole of Compound (XXI).

The amount of the base to be used is about 1 to about 10 moles, preferably about 1 to about 3 moles, per 1 mole of Compound (XXI).

As the "base", for example, metal hydroxides such as sodium hydroxide, potassium hydroxide, lithium hydroxide, barium hydroxide and the like, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, ethers, esters, aromatic hydrocarbons, aliphatic hydrocarbons, amides, halogenated hydrocarbons, nitrites, sulfoxides, organic acids, aromatic amines or a mixture of two or more of them and the like are used.

The reaction temperature is about −20 to about 150° C., preferably about 0 to about 100° C. The reaction time is usually about 5 minutes to about 24 hours, preferably about 10 minutes to about 5 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Compound (Iq) can be obtained by condensing Compound (XXII) with Compound (VII). Where desired, this reaction is carried out in the presence of a base.

The amount of Compound (VII) to be used is about 0.5 to about 3 moles, preferably about 0.8 to about 2 moles, per 1 mole of Compound (XXII).

The amount of the base to be used is about 1 to about 30 moles, preferably about 1 to about 10 moles, per 1 mole of Compound (XXII).

As the "base", for example, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, ethers, amides, alcohols, nitrites or a mixture of two or more of them and the like are used.

The reaction temperature is about −5 to about 200° C., preferably about 5 to about 150° C. The reaction time is usually about 5 minutes to about 72 hours, preferably about 0.5 hour to about 30 hours.

Although the product can be used as a reaction solution itself or as a crude product in the next reaction, it can be isolated from the reaction mixture by a conventional method, and can be easily purified by a separating methods such as recrystallization, distillation, chromatography and the like.

Reaction Scheme 4

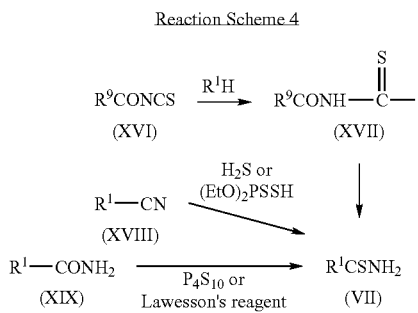

wherein $R^{10}$ is an amino group optionally having substituent(s), and other symbols are as defined above.

Compound (XVII) can be obtained by condensing Compound (XVI) with amines represented by the formula: $R^{10}H$ (e.g., 1-propylamine, 1-butylamine, pyrrolidine, piperidine, piperazine, 4-methylpiperazine, 4-phenylpiperidine and the like, preferably, pyrrolidine, piperidine, piperazine, 4-methylpiperazine etc.).

In Compound (XVII), $R^9$ is an aromatic hydrocarbon group or alkoxy. As the "aromatic hydrocarbon group", phenyl group optionally having substituent(s) and the like can be mentioned. As the "alkoxy", for example, $C_{1-6}$ alkoxy such as methoxy, ethoxy, propoxy, isopropoxy, butoxy and the like, and the like can be mentioned.

The amount of the "amines" to be used is about 1.0 to about 30 moles, preferably about 1.0 to about 10 moles, per 1 mole of Compound (XVI).

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, ethers, amides, alcohols, nitriles, ketones or a mixture of two or more of them and the like are used.

The reaction temperature is about –5 to about 200° C., preferably about 5 to about 120° C. The reaction time is usually about 5 minutes to about 72 hours, preferably about 0.5 to about 30 hours.

Although the product can be used as a reaction solution itself or as a crude product in the next reaction, it can be isolated from the reaction mixture by a conventional methods, and can be easily purified by a separating methods such as recrystallization, distillation, chromatography and the like.

Compound (VII) is obtained by hydrolyzing Compound (XVII) using an acid or a base.

The amount of acid or base to be used is about 0.1 to about 50 moles, preferably about 1 to about 20 moles, per 1 mole of Compound (XVII), respectively.

As the "acid", for example, mineral acids such as hydrochloric acid, hydrobromic acid, sulfuric acid and the like, Lewis acids such as boron trichloride, boron tribromide and the like, the use of Lewis acid together with thiols or sulfides, organic acids such as trifluoroacetic acid, p-toluenesulfonic acid and the like, and the like are used.

As the "base", for example, metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like, and the like are used.

It is advantageous to carry out this reaction without a solvent or in the presence of an inert solvent for the reaction. The solvent is not particularly limited as long as the reaction proceeds, but, for example, alcohols, ethers, aromatic hydrocarbons, aliphatic hydrocarbons, halogenated hydrocarbons, sulfoxides, water or a mixture of two or more of them and the like are used.

The reaction time is usually about 10 minutes to about 50 hours, preferably about 30 minutes to about 12 hours. The reaction temperature is usually about 0 to about 200° C., preferably about 20 to about 120° C.

Compound (VII) can be also obtained by treating Compound (XVIII) with hydrogen sulfide in the presence of a base.

The amount of hydrogen sulfide to be used is about 1 to about 30 moles, per 1 mole of Compound (XVIII).

The amount of base to be used is about 1.0 to about 30 moles, preferably about 1.0 to about 10 moles, per 1 mole of Compound (XVIII).

As the "base", for example, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, ethers, aromatic amines or a mixture of two or more of them and the like are used.

This reaction is performed under atmospheric pressure or under a pressurized condition. The reaction temperature is usually about –20 to about 80° C., preferably about –10 to about 30° C. The reaction time is usually about 5 minutes to about 72 hours, preferably about 0.5 hour to about 30 hours.

Although the product can be used as a reaction solution itself or as a crude product in the next reaction, it can be isolated from the reaction mixture by a conventional methods, and can be easily purified by a separating methods such as recrystallization, distillation, chromatography and the like.

Compound (VII) can be also obtained by treating compound (XVIII) with O,O-diethyl dithiophosphate in the presence of an acid.

The amount of O,O-diethyl dithiophosphate to be used is about 0.9 to about 2 moles, relative to 1 mole of Compound (XVIII).

The amount of acid to be used is about 3.0 to about 30 moles, preferably about 3.0 to about 10 moles, per 1 mole of Compound (XVIII).

As the acid, for example, hydrogen halides such as hydrogen chloride, hydrogen bromide and the like, mineral acids such as hydrochloric acid, hydrobromic acid and the like, and the like are used.

It is advantageous to carry out this reaction without a solvent or in the presence of an inert solvent for the reaction. The solvent is not particularly limited as long as the reaction proceeds, but, for example, halogenated hydrocarbons, alcohols, amides, ethers, esters, water or a mixture of two or more of them and the like are used.

The reaction temperature is generally about 0 to about 80° C., preferably about 0 to about 30° C. The reaction time is generally about 5 minutes to about 72 hours, preferably about 0.5 hour to about 30 hours.

Although the product can be used as a reaction solution itself or as a crude product in the next reaction, it can be isolated from the reaction mixture by a conventional methods, and can be easily purified by a separating methods such as recrystallization, distillation, chromatography and the like.

Compound (VII) can also be obtained by treating Compound (XIX) with phosphorus pentasulfide or Lawesson's reagent.

The amount of the phosphorus pentasulfide or Lawesson's reagent to be used is about 0.5 to about 10 moles, preferably about 0.5 to about 3 moles, per 1 mole of Compound (XIX).

It is advantageous to carry out this reaction without a solvent or in the presence of an inert solvent for the reaction. The solvent is not particularly limited as long as the reaction proceeds, but, for example, ethers, aromatic hydrocarbons, aliphatic hydrocarbons, halogenated hydrocarbons or a mixture of two or more of them and the like are used.

The reaction time is usually 10 minutes to about 50 hours, preferably about 30 minutes to about 12 hours. The reaction temperature is usually 0 to about 150° C., preferably about 20 to about 120° C.

Although the product (VII) can be used as a reaction solution itself or as a crude product in the next reaction, it can be isolated from the reaction mixture by a conventional methods, and can be easily purified by a separating methods such as recrystallization, distillation, chromatography and the like.

When Compound (Im) is an acylamino compound, the objective compound can be also obtained by subjecting the corresponding amine compound to an acylating reaction known per se.

Of Compound (Im), for example, a compound wherein $R^1$ is acylamino group optionally having substituent(s) is obtained by reacting the corresponding 2-thiazolamine and an acylating agent optionally in the presence of a base or an acid.

The amount of the acylating agent to be used is about 1 to about 5 moles, preferably about 1 to about 2 moles, per 1 mole of the corresponding 2-thiazolamine.

As the "acylating agent", for example, carboxylic acids corresponding to an objective acyl group or a reactive derivative thereof (e.g., acid halide, acid anhydride, ester and the like) and the like can be mentioned.

The amount of the base or acid to be used is about 0.8 to about 5 moles, preferable about 1 to about 2 moles, per 1 mole of the corresponding 2-thiazolamine.

As the "base", for example, triethylamine, pyridine, 4-dimethylaminopyridine and the like can be mentioned.

As the "acid", for example, methanesulfonic acid, p-toluenesulfonic acid, camphorsulfonic acid and the like can be mentioned.

It is advantageous to carry out this reaction without a solvent or in the presence of an inert solvent for the reaction. The solvent is not particularly limited as long as the reaction proceeds, but, for example, ethers, aromatic hydrocarbons, aliphatic hydrocarbons, amides, halogenated hydrocarbons, nitriles, sulfoxides, aromatic amines or a mixture of two or more of them and the like are used.

The reaction temperature is about −20 to about 150° C., preferably about 0 to about 100° C. The reaction time is usually 5 minutes to about 24 hours, preferably about 10 minutes to about 5 hours.

Although the product can be used as a reaction solution itself or as a crude product in the next reaction, it can be isolated from the reaction mixture by a conventional methods, and can be easily purified by a separating methods such as recrystallization, distillation, chromatography and the like.

When Compound (Im) is an N-oxide compound, it is obtained by treating the corresponding pyrimidine compound with an organic peroxy acid.

The amount of the organic peroxy acid to be used is about 0.8 to about 10 moles, preferable about 1.0 to about 3.0 moles, per 1 mole of the corresponding pyrimidine compound.

As the "organic peroxy acid", for example, peracetic acid, trifluoroperacetic acid, m-chloroperbenzoic acid and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, organic acids, ethers, amides, sulfoxides, alcohols, nitrites, ketones or a mixture of two or more of them and the like are used.

The reaction temperature is about −20° C. to about 130° C., preferably about 0 to about 100° C. The reaction time is usually 5 minutes to about 72 hours, preferably about 0.5 hour to about 12 hours.

Alternatively, the N-oxide compound is also obtained by treating the corresponding pyrimidine compound with hydrogen peroxide or alkyl hydroperoxide in the presence of a base, an acid or a metal oxide, if desired.

The amount of the hydrogen peroxide or alkyl hydroperoxide to be used is about 0.8 to about 10 moles, preferably about 1.0 to about 3.0 moles, per 1 mole of the corresponding pyrimidine compound.

As the "alkyl hydroperoxide", for example, tert-butyl hydroperoxide, cumene hydroperoxide and the like can be mentioned.

The amount of the base, acid or metal oxide to be used is about 0.1 to about 30 moles, preferably 0.8 to about 5 moles, per 1 mole of the corresponding pyrimidine compound.

As the "base", for example, inorganic bases such as sodium hydroxide, potassium hydroxide and the like, basic salts such as sodium carbonate, potassium carbonate and the like, and the like can be mentioned.

As the "acid", for example, mineral acids such as hydrochloric acid, sulfuric acid, perchloric acid and the like, Lewis acids such as boron trifluoride, aluminum chloride, titanium tetrachloride and the like, organic acids such as formic acid, acetic acid and the like, and the like can be mentioned.

As the "metal oxide", for example, vanadium oxide (e.g., $V_2O_5$ etc.), osmium tetroxide ($OsO_4$), tungsten oxide (e.g., $WO_3$ etc.), molybdenum oxide (e.g., $MoO_3$ etc.), selenium dioxide ($SeO_2$), chromium oxide (e.g., $CrO_3$ etc.) and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, organic acids, ethers, amides, sulfoxides, alcohols, nitriles, ketones or a mixture of two or more of them and the like are used.

The reaction temperature is about −20° C. to about 130° C., preferably about 0° C. to about 100° C. The reaction time is usually 5 minutes to about 72 hours, preferably about 0.5 hour to about 12 hours.

Although the product can be used as a reaction solution itself or as a crude product in the next reaction, it can be a mixture isolated by a conventional method, and can be easily purified by a separating methods such as recrystallization, distillation, chromatography and the like.

When compound (Im) is an S-oxide compound, it can be obtained by treating the corresponding sulfide compound with peroxide.

The amount of peroxide to be used is about 0.8 to about 10 moles, preferably about 1.0 to about 3.0 moles, relative to 1 mole of the corresponding sulfide compound.

As the "peroxide", for example, peracetic acid, trifluoroperacetic acid, m-chloroperbenzoic acid, potassium persulfate, metaperiodic acid and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, organic acids, ethers, amides, sulfoxides, alcohols, nitrites, ketones or a mixture of two or more of them and the like are used.

The reaction temperature is about −20° C. to about 130° C., preferably about 0° C. to about 100° C. The reaction time is usually about 5 minutes to about 72 hours, preferably about 0.5 hour to about 12 hours.

In addition, an S-oxide compound can be obtained by treating the corresponding sulfide compound with hydrogen peroxide or alkyl hydroperoxide in the presence of a base, acid and/or metal oxide, if desired.

The amount of the hydrogen peroxide or alkyl hydroperoxide to be used is about 0.8 to about 10 moles, preferably about 1.0 to about 3.0 moles, per 1 mole of the corresponding sulfide compound.

As the "alkyl hydroperoxide", for example, tert-butyl hydroperoxide, cumene hydroperoxide and the like can be mentioned.

The amount of the "base, acid or metal oxide" to be used is about 0.1 to about 30 moles, preferably about 0.8 to about 5 moles, per 1 mole of the corresponding sulfide compound.

As the "base", for example, inorganic bases such as sodium hydroxide, potassium hydroxide and the like, basic salts such as sodium carbonate, potassium carbonate and the like, and the like can be mentioned.

As the "acid", for example, mineral acids such as hydrochloric acid, sulfuric acid, perchloric acid and the like, Lewis acids such as boron trifluoride, aluminum chloride, titanium tetrachloride and the like, organic acids such as formic acid, acetic acid and the like, and the like can be mentioned.

As the "metal oxide", for example, vanadium oxide (e.g., $V_2O_5$ etc.), osmium tetroxide ($OsO_4$), tungsten oxide (e.g., $WO_3$ etc.), molybdenum oxide (e.g., $MoO_3$ etc.), selenium dioxide ($SeO_2$), chromium oxide (e.g., $CrO_3$ etc.) and the like can be mentioned.

It is advantageous to carry out this reaction without a solvent or in the presence of an inert solvent for the reaction. The solvent is not particularly limited as long as the reaction proceeds, but, for example, halogenated hydrocarbons, aliphatic hydrocarbons, aromatic hydrocarbons, organic acids, ethers, amides, sulfoxides, alcohols, nitriles, ketones or a mixture of two or more of them and the like are used.

The reaction temperature is about −20° C. to about 130° C., preferably about 0° C. to about 100° C. The reaction time is usually about 5 minutes to about 72 hours, preferably about 0.5 to about 12 hours.

Although the product can be used as a reaction solution itself or as a crude product in the next reaction, it can be a mixture isolated by a conventional methods, and can be easily purified by a separating methods such as recrystallization, distillation, chromatography and the like.

In the respective reactions mentioned above, when starting compounds have amino, carboxy, hydroxy as substituents, a protecting groups which are generally used in the peptide chemistry or the like may be introduced into these groups and, after reaction, a desired compound can be obtained by removing protecting groups if needed.

As a protecting group for amino, for example, formyl or $C_{1-6}$ alkyl-carbonyl (e.g., acetyl, propionyl and the like), phenylcarbonyl, $C_{1-6}$ alkoxy-carbonyl (e.g., methoxycarbonyl, ethoxycarbonyl and the like), phenyloxycarbonyl, $C_{7-10}$ aralkyloxy-carbonyl (e.g., benzyloxycarbonyl and the like), trityl, phthaloyl and the like, which may have substituent(s) are used. As these substituent(s), halogen atom(s) (e.g., fluorine, chlorine, bromine, iodine and the like), $C_{1-6}$ alkylcarbonyl (e.g., acetyl, propionyl, valeryl and the like), nitro and the like are used and the number of substituents is 1 to 3.

As a protecting group for carboxy, for example, $C_{1-6}$ alkyl (e.g., methyl, ethyl, propyl, isopropyl, butyl, tert-butyl and the like), phenyl, trityl, silyl and the like, which may have substituent(s), are used. As these substituent(s), halogen atom(s) (e.g., fluorine, chlorine, bromine, iodine and the like), formyl, $C_{1-6}$ alkyl-carbonyl (e.g., acetyl, propionyl, butylcarbonyl and the like), nitro, $C_{1-6}$ alkyl (e.g., methyl, ethyl, tert-butyl and the like), $C_{6-10}$ aryl (e.g., phenyl, naphthyl and the like) and the like are used and the number of substituents is 1 to 3.

As a protecting group for hydroxy, for example, $C_{1-6}$ alkyl (e.g., methyl, ethyl, propyl, isopropyl, butyl, tert-butyl and the like), phenyl, $C_{7-11}$ aralkyl (e.g., benzyl and the like), formyl, $C_{1-6}$ alkyl-carbonyl (e.g., acetyl, propionyl and the like), phenyloxycarbonyl, $C_{7-11}$ aralkyloxy-carbonyl (e.g., benzyloxycarbonyl and the like), tetrahydropyranyl, tetrahydrofuranyl, silyl and the like, which may have substituent(s), are used. As these substituent(s), halogen atom(s) (e.g., fluorine, chlorine, bromine, iodine and the like), $C_{1-6}$ alkyl (e.g., methyl, ethyl, tert-butyl and the like), $C_{7-11}$ aralkyl (e.g., benzyl and the like), $C_{6-10}$ aryl (e.g., phenyl, naphthyl and the like), nitro and the like are used, wherein the number of substituents is 1 to 4.

In addition, as a method of removing a protecting group, a method known per se or a method according to such method is used, and, for example, method by treating with an acid, a base, ultraviolet rays, hydrazine, phenylhydrazine, sodium N-methyldithiocarbamate, tetrabutylammonium fluoride, palladium acetate and the like or a method of reduction is used.

In any case, Compound (I) can be synthesized by optionally applying further known deprotection, acylation, alkylation, hydrogenation, oxidation, reduction, carbon chain extension and substituent exchange reactions alone or a combination of two or more of them. As these reactions, those described in, for example, *Shinjikkenkagakukoza* 14, vol. 15, 1977 (Maruzen Press) and the like are adopted.

As the above "alcohols", for example, methanol, ethanol, propanol, isopropanol, tert-butanol and the like can be mentioned.

As the above "ethers", for example, diethyl ether, diisopropyl ether, diphenyl ether, tetrahydrofuran, dioxane, 1,2-dimethoxyethane and the like can be mentioned.

As the above "halogenated hydrocarbons", for example, dichloromethane, chloroform, 1,2-dichloroethane, carbon tetrachloride and the like can be mentioned.

As the above "aliphatic hydrocarbons", for example, hexane, pentane, cyclohexane and the like can be mentioned.

As the above "aromatic hydrocarbons", for example, benzene, toluene, xylene, chlorobenzene and the like can be mentioned.

As the above "aromatic amines", for example, pyridine, lutidine, quinoline and the like can be mentioned.

As the above "amides", for example, N,N-dimethylformamide, N,N-dimethylacetamide, hexamethylphosphoric triamide and the like can be mentioned.

As the above "ketones", for example, acetone, methyl ethyl ketone and the like can be mentioned.

As the above "sulfoxides", for example, dimethyl sulfoxide and the like can be mentioned.

As the above "nitriles", for example, acetonitrile, propionitrile and the like can be mentioned.

As the above "organic acids", for example, acetic acid, propionic acid, trifluoroacetic acid and the like can be mentioned.

As the above "esters", for example, methyl acetate, ethyl acetate, amyl acetate, methyl propionate and the like can be mentioned.

When a desired product is obtained in a free form by the above reaction, it may be converted into a salt according to conventional methods or, when a desired product is obtained as a salt, it can be converted into a free form or another salt according to conventional methods. Compound (I) of the present invention thus obtained can be isolated and purified from the reaction solution by the known methods, for example, trans-solvation, concentration, solvent extraction, fractional distillation, crystallization, recrystallization, chromatography and the like.

When Compound (I) according to the present invention is present as a configurational isomer (stereoisomer), diastereomer, conformer (conformational isomer) or the like, each can be optionally isolated by the above separation and purification methods. In addition, when Compound (I) according to the present invention is in the form of its racemate, they can be separated into S- and R-forms by any conventional optical resolution.

When Compound (I) according to the present invention includes stereoisomers, both the isomers alone and mixtures of each isomers are included in the scope of the present invention.

In addition, Compound (I) according to the present invention may be a hydrate or non-hydrate.

Compound (I) according to the present invention may be labeled with an isotope (e.g., $^3$H, $^{14}$C, $^{35}$S and the like) or the like.

A prodrug for Compound (I) according to the present invention refers to a compound which is converted to Compound (I) as a result of a reaction with an enzyme, gastric acid etc. under physiological conditions in vivo, thus a compound that undergoes enzymatic oxidation, reduction, hydrolysis etc. to convert into Compound (I) and a compound that undergoes hydrolysis and the like by gastric acid etc. to convert into Compound (I). As a prodrug for Compound (I), a compound obtained by subjecting an amino group in Compound (I) to an acylation, alkylation or phosphorylation (e.g., a compound obtained by subjecting an amino group in Compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in Compound (I) to an acylation, alkylation, phosphorylation and boration (e.g., a compound obtained by subjecting a hydroxy group in Compound (I) to an acetylation, palmitoylation, propanoylation, pivaloylation, succinylation, fumarylation, alanylation, dimethylaminomethylcarbonylation, etc.); a compound obtained by subjecting a carboxyl group in Compound (I) to an esterification or amidation (e.g., a compound obtained by subjecting a carboxyl group in Compound (I) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation, etc.) and the like can be mentioned. Any of these compounds can be produced from Compound (I) by a method known per se.

A prodrug for Compound (I) may also be one which is converted to Compound (I) under physiological conditions as described in "IYAKUHIN no KAIHATSU (Development of Pharmaceuticals)", Vol.7, Design of Molecules, p. 163–198, Published by HIROKAWA SHOTEN (1990).

Compound (I) or a prodrug thereof (hereinafter sometimes to be abbreviated as Compound of the present invention) of the present invention has superior c-Jun N-terminal kinase (JNK) inhibitory activity, shows low toxicity and causes a fewer side effects. Thus, it is useful as a safe pharmaceutical agent, such as a JNK inhibitor.

The pharmaceutical agent of the present invention, which contains the compound of the present invention shows superior JNK inhibitory action in mammals (e.g., mouse, rat, hamster, rabbit, cat, dog, bovine, sheep, monkey, human etc.) and is superior in (oral) absorbability, (metabolic) stability and the like. Thus, it can be used as a prophylactic or therapeutic agent of JNK related diseases, c-Jun related diseases, such as acute pancreatitis, chronic pancreatitis, adult respiratory distress syndrome, pachyderma, lupus erythematosus profundus, chronic thyroiditis, Graves' disease, autoimmune gastritis, autoimmune neutropenia, thrombocytopenia, myasthenia gravis, multiple myeloma, acute myeloblastic leukemia, chronic sarcoma, chronic myelocytic leukemia, metastatic melanoma, Kaposi's sarcoma, degenerative disease, Huntington's disease, a disease associated with ischemia/reperfusion in stroke, myocardial ischemia, ischemic cardiac disease, renal ischemia, neovascular glaucoma, infantile angioma, vascularization, hypercardia, abnormal immune response, fervescence, cellular aging, apoptosis related disease and the like.

Of the compounds of the present invention, moreover, a compound concurrently having, in addition to the JNK inhibitory activity, p38 MAP kinase inhibitory action and/or inflammatory cytokine inhibitory action [e.g., TNF-$_\alpha$ inhibitory action (e.g., TNF-$_\alpha$ production inhibitory action, TNF-$_\alpha$ action inhibitory action and the like), interleukin-1 (IL-1) inhibitory action, interleukin-6 (IL-6) inhibitory action and the like] and the like is preferable.

In this way, the compound of the present invention concurrently having, in addition to the JNK inhibitory action, p38 MAP kinase inhibitory action and/or inflammatory cytokine inhibitory action [e.g., TNF-$_\alpha$ inhibitory action and the like] shows low toxicity and fewer side effects. Thus, it is useful as a safe pharmaceutical product, such as JNK inhibitor, p38 MAP kinase inhibitor, inflammatory cytokine production inhibitor, TNF-$\alpha$ inhibitor (e.g., TNF-$\alpha$ production inhibitor, TNF-$\alpha$ action inhibitor and the like), IL-1 inhibitor, IL-6 inhibitor and the like.

The p38 MAP kinase inhibitor and/or TNF-$\alpha$ inhibitor such as Compounds (I) to be used in the present invention has superior p38 MAP kinase inhibitory action, TNF-$\alpha$ inhibitory action (TNF-$\alpha$ production inhibitory action, TNF-$\alpha$ action inhibitory action), interleukin-1 (IL-1) inhibitory action, interleukin-6 (IL-6) inhibitory action, phosphodiesterase IV (PDE IV) inhibitory action and the like, and shows low toxicity and fewer side effects. Thus, it is useful as a safe pharmaceutical product, p38 MAP kinase inhibitor, TNF-$\alpha$ production inhibitor, IL-1 inhibitor, IL-6 inhibitor, PDE IV inhibitor and the like.

The p38 MAP kinase inhibitor and/or TNF-$\alpha$ inhibitor such as. Compound (I) to be used in the present invention shows superior p38 MAP kinase inhibitory activity and TNF-$\alpha$ inhibitory activity and is also excellent in (oral) absorbability, (metabolic) stability and the like in mammals (e.g., mouse, rat, hamster, rabbit, cat, dog, bovine, sheep, monkey, human and the like) and, therefore, can be used as an agent for the prophylaxis or treatment of p38 MAP kinase related diseases and TNF-$\alpha$ production related diseases, such as asthma, chronic obstructive pulmonary disease (COPD), allergic disease (e.g., allergic dermatitis, allergic rhinitis), atopic dermatitis, inflammation, inflammatory eye disease, Addison's disease, autoimmune hemolytic anemia, systemic lupus erythematosus, Crohn's disease, psoriasis, rheumatism, central nervous disease (e.g., cerebrovascular disease such as cerebral hemorrhage and cerebral infarction, head trauma, spinal cord injury, brain edema, multiple sclerosis and the like), neurodegenerative disease (e.g., Alzheimer's disease, Parkinson's disease, amyotrophic lateral sclerosis (ALS), AIDS encephalopathy), meningitis, diabetes, arthritis (e.g., chronic rheumatoid arthritis, osteoarthritis, rheumatoid-like spondylitis, urarthritis, synovitis), osteoporosis, toxemia (e.g., sepsis, septic shock, endotoxic shock, Gram negative sepsis, toxic shock syndrome), inflammatory bowel disease (e.g., Crohn's disease, ulcerative colitis), inflammatory pulmonary disease (e.g., chronic pneumonia, pulmonary silicosis, pulmonary sarcoidosis, pulmonary tuberculosis) or cachexia (e.g., infectious cachexia, cancerous cachexia, cachexia by acquired immunodeficiency syndrome (AIDS)), arteriosclerosis, Creutzfeldt-Jakob disease, virus infection (e.g., infection with cytomegalovirus, influenzavirus, herpesvirus and the like), angina pectoris, cardiac infarction, congestive heart failure, chronic cardiac deficiency, acute myocardial infarction, prognosis of cardiac infarction, hypertension, acute cardiac deficiency, hepatitis, kidney failure, nephritis, malignant tumor, immunological rejection associated with transplantation, dialysis hypotension, disseminated intravascular coagulation, and the like. Particularly, they can be used as an agent for the prophylaxis or treatment of chronic rheumatoid arthritis, osteoarthritis and the like.

In addition, the p38 MAP kinase inhibitor and/or TNF-$\alpha$ inhibitor such as Compounds (I) to be used in the present invention have PDE IV inhibitory activity and can be used as a prophylactic or therapeutic agent of diseases caused by inflammation, such as bronchial asthma, chronic obstructive pulmonary disease (COPD), chronic rheumatoid arthritis, autoimmune disease, diabetes, graft versus host disease, multiple sclerosis, sepsis, psoriasis, osteoporosis, depression, central hypergasia after cerebrovascular obstruction, cerebrovascular dementia, Alzheimer's dementia, obesity, cardiac failure and the like.

Accordingly, the pharmaceutical composition of the present invention containing the compound of the present invention concurrently having, in addition to the JNK inhibitory activity, p38 MAP kinase inhibitory action and/or inflammatory cytokine inhibitory action [e.g., TNF-$\alpha$ inhibitory action and the like] shows superior JNK inhibitory activity, p38 MAP kinase inhibitory action, inflammatory cytokine inhibitory action and TNF-$\alpha$ inhibitory action in mammals (e.g., mouse, rat, hamster, rabbit, cat, dog, bovine, sheep, monkey, human etc.) and is superior in (oral) absorbability, (metabolic) stability and the like. Thus, it can be used as a prophylactic or therapeutic agent for, for example, inflammatory diseases (e.g., acute pancreatitis, chronic pancreatitis, hepatitis, asthma, adult respiratory distress syndrome, meningitis, arthritis (e.g., gouty arthritis, synovitis and the like), spondylitis (e.g., rheumatoid spondylitis and the like), inflammatory bone disease, inflammatory ophthalmic disease, inflammatory pulmonary diseases (e.g., chronic pneumonia, pulmonary silicosis, pulmonary sarcoidosis, pulmonary tuberculosis and the like), bronchitis and the like), autoimmune diseases (e.g., nephritis, Addison's disease, rheumatoid arthritis, systemic lupus erythematosus, pachyderma, lupus erythematosus profundus, chronic thyroiditis, Graves' disease, autoimmune gastritis, diabetes, autoimmune hemolytic anemia, autoimmune neutropenia, thrombocytopenia, atopic dermatitis, active chronic hepatitis, myasthenia gravis, inflammatory bowel disease, ulcerative colitis, Crohn's disease, psoriasis and the like), destructive bone diseases (e.g., osteoarthrosis, osteoporosis, multiple myeloma and the like), proliferative diseases (e.g., acute myeloblastic leukemia, chronic sarcoma, chronic myelocytic leukemia, metastatic melanoma, Kaposi's sarcoma and the like), degenerative disease, neurodegenerative diseases (e.g., Alzheimer's disease, Parkinson's syndrome, amyotrophic lateral sclerosis, Huntington's disease, Creutzfeldt-Jakob disease, traumatic neurodegenerative disease, a disease associated with ischemia/reperfusion in stroke, and the like), central nervous system disorders (e.g., cerebrovascular disorders such as cerebral hemorrhage and cerebral infarction and the like, a disease associated with ischemia/reperfusion in stroke, brain ischemia, external injury in head, spinal trauma, brain edema multiple sclerosis, multiple sclerosis and the like), cardiac diseases (e.g., myocardial ischemia, ischemic cardiac disease, cardiac infarction, angina pectoris, congestive heart failure, chronic cardiac incompetence, acute cardiac infarction, prognosis of cardiac infarction, acute cardiac incompetence, hypercardia and the like), hypertension, renal ischemia, dialysis hypotension, angiogenesis related diseases (e.g., solid tumor, neovascular glaucoma, infantile angioma and the like), vascularization, arteriosclerosis, disseminated intravascular coagulation, abnormal immune response, toxemia (e.g., sepsis, septic shock, endotoxin shock, gram-negative sepsis, toxic shock syndrome and the like), pulmonary infarction, graft-versus-host reaction, fervescence, infectious disease (e.g., virus infection (e.g., infection with cytomegalovirus, influenza virus, herpesvirus and the like, etc.), bacterial infectious disease and the like), cachexia (e.g., cachexia due to infection, cancer cachexia, cachexia due to acquired immunodeficiency syndrome (AIDS) etc.), dermatitis, actinic dermatitis, bone resorption, cellular aging, apoptosis related disease and the like.

In addition, the novel Compound (Im) [including (In), (If'), (Ig'), (Ih'), (Io) and (Ip)] of the present invention has the above-mentioned p38 MAP kinase inhibitory action, inflammatory cytokine inhibitory action and/or JNK inhibitory action and can be used as a prophylactic or therapeutic agent of the above-mentioned related diseases.

The preparation of the present invention containing the compound of the present invention shows low toxicity, and can be safely administered orally or parenterally (e.g., topical, rectal, intravenous administration etc.) as a pharmaceutical preparation of the compound of the present invention as it is or after admixing with a pharmacologically acceptable carrier to give, for example, tablet (including sugar-coated tablet and film-coated tablet), powder, granule, capsules (including soft capsules), liquid, injection, suppository, sustained-release preparation and the like, according to a methods known per se used for the general production method for pharmaceutical preparations. The content of the Compound of the present invention in a pharmaceutical composition of the present invention is about 0.01 to about 100% by weight relative to the whole preparation. The dose varies depending on administration subjects, administration route, diseases, condition and the like. The preparation may be orally administered, as a prophylactic or therapeutic agent for p38 MAP kinase related diseases, for example, to a patient with arthritis (body weight about 60 kg), about 0.01 to about 30 mg active ingredient (a compound according to the present invention)/kg body weight per day, preferably about 0.1 to about 20 mg/kg body weight per day, more preferably about 1 to about 20 mg/kg body weight per day, which is given once or divided into several doses a day.

As a pharmacologically acceptable carrier which may be used for preparing a preparation of the present invention, the conventional various organic or inorganic carriers as a pharmaceutical material, for example, excipient, lubricant, binder and disintegrating agent in solid preparations, or solvent, solubilizing agent, suspending agent, isotonizing agent, buffer and soothing agent in liquid preparations, and the like can be mentioned. Further, if needed, additives such as the conventional preservative, antioxidant, colorant, sweetening agent, adsorbing agent, wetting agent and the like can be appropriately used at an appropriate amount.

As an excipient, for example, lactose, saccharose, D-mannitol, starch, corn starch, crystalline cellulose, light silicic acid anhydride and the like can be mentioned.

As a lubricant, for example, magnesium stearate, calcium stearate, talc, colloidal silica and the like can be mentioned.

As a binder, for example, crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like can be mentioned.

As a disintegrating agent, for example, starch, carboxymethyl cellulose, calcium carboxymethyl cellulose, sodium carboxymethyl starch, L-hydroxypropylcellulose and the like can be mentioned.

As a solvent, for example, water for injection, alcohol, propylene glycol, macrogol, sesame oil, corn oil, olive oil and the like can be mentioned.

As a solubilizing agent, for example, polyethylene glycol, propylene glycol, D-mannitol, benzyl benzoate, ethanol, tris-aminomethane, cholesterol, triethanolamine, sodium carbonate, sodium citrate and the like can be mentioned.

As a suspending agent, for example, surfactants such as stearyl triethenolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethyl cellulose, methylcellulose, hydroxymethylcellulose, hydroxyethylcellulose, hydoxypropylcellulose and the like, and the like can be mentioned.

As an isotonizing agent, for example, glucose, D-sorbitol, sodium chloride, glycerin, D-mannitol and the like can be mentioned.

As a buffer, for example, buffering solutions such as phosphate, acetate, carbonate, citrate and the like, and the like can be mentioned.

As a soothing agent, for example, benzyl alcohol and the like can be mentioned.

As a preservative, for example, p-hydroxybenzoates, chlorobutanol, benzyl alcohol, phenethyl alcohol, dehydroacetic acid, sorbic acid and the like can be mentioned.

As an antioxidant, for example, sulfites, ascorbic acid, $_\alpha$-tocopherol and the like can be mentioned.

As the colorant, for example, water-soluble food coal-tar dyes, water-insoluble lake dyes, natural pigments (e.g., β-carotene, chlorophiles, colcothar etc.) and the like can be mentioned.

As the sweetening agent, for example, saccharin sodium, dipotassium glycyrrhizinate, aspartam, stevia and the like can be mentioned.

In addition, the Compound of the present invention can be used in combination with a drug other than the compound of the present invention.

The drugs that can be used in combination with the compound of the present invention (hereinafter the drug is sometimes abbreviated as a concomitant drug) include, for example, the following.

(1) Non-Steroidal Antiinflammatory Drugs (NSAIDs)

A. Classical NSAIDs alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

B. cyclooxygenase inhibitor (COX-1 selective inhibitor, COX-2 selective inhibitor and the like)

salicylic acid derivatives (e.g., celecoxib, rofecoxib, aspirin etc.), MK-663, valdecoxib, SC-57666, tiracoxib, S-2474, diclofenac, indomethacin, loxoprofen and the like.

C. drug concurrently having COX inhibitory activity and 5-lipoxygenase inhibitory activity ML-3000, p54 (COX inhibitor & 5-lipoxygenase inhibitor) and the like.

D. nitric oxide-releasing NSAIDs (2) Disease-Modifying Anti-Rheumatic Drugs (DMARDs)

A. Gold preparation

Auranofin and the like.

B. penicillamine

D-penicillamine

C. sulfasalazine

D. antimalarial drug chloroquine and the like.

E. pyrimidine synthesis inhibitor
  leflunomide and the like.
F. prograf (3) Anti-Cytokine Drug
(I) protein drug
(i) TNF inhibitor
  etanercept, infliximab, D2E7, CDP-571, PASSTNF-$\alpha$, soluble TNF-$\alpha$ receptor, TNF-$\alpha$ binding protein, anti-TNF-$\alpha$ antibody and the like.
(ii) interleukin-1 inhibitor
  anakinra (interleukin-1 receptor antagonist), soluble interleukin-1 receptor and the like.
(iii) interleukin-6 inhibitor
  MRA (anti-interleukin-6 receptor antibody), anti-interleukin-6 antibody and the like.
(iv) interleukin-10 drug
  interleukin-10 and the like.
(v) interleukin-12 inhibitor
  anti-interleukin-12 antibody and the like.
(vi) drug concurrently having interferon-$\alpha$ and -$\gamma$ inhibitory activity and TNF-$\alpha$ inhibitory activity (polyclonal antibody)
  AGT-1
(II) non-protein drug
(i) MAP kinase inhibitor
  PD-98059 and the like.
(ii) gene modulator
  SP-100030, inhibitor of molecule involved in signal transduction, such as NF-$\kappa$, NF-$\kappa$B, IKK-1, IKK-2, AP-1 and the like, and the like
(iii) cytokine production inhibitor
  T-614, SR-31747, sonatimod and the like.
(iv) TNF-$\alpha$ converting enzyme inhibitor
(v) interleukin-1$\beta$ converting enzyme inhibitor
  HMR3480/VX-740 and the like.
(vi) interleukin-6 antagonist
  SANT-7 and the like.
(vii) interleukin-8 inhibitor
  IL-8 antagonist, CXCR1 & CXCR2 antagonist and the like.
(viii) chemokine antagonist
  MCP-1 antagonist and the like.
(ix) interleukin-2 receptor antagonist
  denileukin diftitox and the like.
(x) therapeutic vaccines
  TNF-$\alpha$ vaccine and the like.
(xi) gene therapy drug
  gene therapy drugs aiming at promoting the expression of gene having an anti-inflammatory action such as interleukin-4, interleukin-10, soluble interleukin-1 receptor, soluble TNF-$\alpha$ receptor and the like.
(xii) antisense compound
  ISIS-104838 and the like.

(4) Immunomodulator (Immunosuppressant)
(i) T Cell differentiation modulator
  ethyl 6,7-dimethoxy-4-(3,4-dimethoxyphenyl)-2-(1,2,4-triazol-1-ylmethyl)quinoline-3-carboxylate (JP-A-7-118266)
(ii) others
  methotrexate, cyclophosphamide, MX-68, atiprimod dihydrochloride, BMS-188667, CKD-461, rimexolone, cyclosporine, tacrolimus, gusperimus, azathiopurine, antilymphocyte serum, freeze-dried sulfonated normal immunoglobulin, erythropoietin, colony stimulating factor, interleukin, interferon and the like.

(5) Steroid
  dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.

(6) p38 MAP Kinase Inhibitor or TNF-$\alpha$ Production Inhibitor
  compounds described in WO98/57966, WO98/56377, WO98/25619, WO98/07425, WO98/06715, U.S. Pat. No. 5,739,143, WO97/35855, WO97/33883, WO97/32583, WO97/25048, WO97/25046, WO96/10143, WO96/21654, WO95/07922, WO2000/09525, WO99/17776, WO99/01131, WO98/28292, WO97/25047, WO97/25045, U.S. Pat. No. 5,658,903, WO96/21452, WO99/18942, U.S. Pat. No. 5,756,499, U.S. Pat. No. 5,864,036, U.S. Pat. No. 6,046,208, U.S. Pat. No. 5,716,955, U.S. Pat. No. 5,811,549, U.S. Pat. No. 5,670,527, U.S. Pat. No. 5,969,184, WO2000/31072, WO2000/31063, WO2000/20402, WO2000/18738, WO2000/17175, WO2000/12497, WO2000/12074, WO2000/07991, WO2000/07980, WO2000/02561, U.S. Pat. No. 6,096,711, WO99/64400, WO99/61440, WO99/59959, WO99/58523, WO99/58502, WO99/57101, WO99/32111, WO99/32110, WO99/26657, WO99/20624, WO99/18942, WO99/15164, WO99/00357, WO98/52940, WO98/52937, WO98/52558, WO98/06715, WO97/22256, WO96/21452, WO2000/43366, WO2000/42003, WO2000/42002, WO2000/41698, WO2000/41505, WO2000/40243, WO2000/34303, WO2000/25791, WO2000/17204, WO2000/10563, U.S. Pat. No. 6,080,546, WO99/61426, WO99/32463, WO99/32121, WO99/17776, WO98/28292, WO98/27098, WO98/25619, WO98/20868, WO97/35855, WO97/32583, WO97/25048, WO97/25047, WO97/25046, WO97/25045, U.S. Pat. No. 5,658,903, WO96/40143, WO96/21654, WO2000/55153, WO2000/55120, WO2000/26209, U.S. Pat. No. 6,046,208, U.S. Pat. No. 5,756,499, U.S. Pat. No. 5,864,036, JP-A-2000-86657, WO99/59960, WO99/21859, WO99/03837, WO99/01449, WO99/01136, WO99/01130, U.S. Pat. No. 5,905,089, WO98/57966, WO98/52941, WO98/47899, WO98/07425, WO97/33883, WO2000/42213, WO99/58128, WO2000/04025, WO2000/40235, WO2000/31106, WO97/46228, WO2000/59904, WO2000/42003, WO2000/42002, WO2000/41698, WO2000/10563, WO99/61426, WO99/32463, U.S. Pat. No. 6,002,008, WO98/43960, WO98/27098, WO97/35856, WO97/35855, WO96/22985, JP-A-61-145167.

(7) Others
(i) T cell inhibitors
  IR-501 (T cell receptor peptide) and the like.
(ii) inosine monophosphate dehydrogenase (IMPDH) inhibitor
  mycophenolate mofetil, VX-497 and the like.
(iii) adhesion molecule inhibitor
  ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
  BB-3644, CGS-27023A, Bay-12-9566, KB-R7785, L-758354, POL-641 and the like.
(vii) glucose-6-phosphate dehydrogenase inhibitor
  CBF-BS2 and the like.

(viii) hydroorotate dehydrogenase (DHODH) inhibitor
(ix) phosphodiesterase IV (PDE IV) inhibitor
    CG-1088 and the like.
(x) phospholipase $A_2$ inhibitor
(xi) iNOS inhibitor
    NOX-200 and the like.
(xii) microtubule stimulating drug
    paclitaxel and the like.
(xiii) microtubule inhibitor
    reumacon and the like.
(xiv) MHC class II antagonist
    ZD-2315 and the like.
(xv) prostacyclin agonist
    iloprost and the like.
(xvi) CD4 antagonist
    4162W94, keliximab and the like.
(xvii) CD23 antagonist
(xviii) LTB4 receptor antagonist
    CGS-25019C and the like.
(xix) 5-lipoxygenase inhibitor
    zileuton and the like.
(xx) cholinesterase inhibitor
    galanthamine and the like.
(xxi) tyrosine kinase inhibitor
    YT-146 and the like.
(xxii) cathepsin B inhibitor
(xxiii) adenosine deaminase inhibitor
    pentostatin and the like.
(xxiv) osteogenesis stimulator
    (2R,4S)-(−)-N-[4-(diethoxyphosphorylmethyl)phenyl]-1,2,4,5-tetrahydro-4-methyl-7,8-methylenedioxy-5-oxo-3-benzothiepin-2-carboxamide or a salt thereof (JP-A-8-231659) and the like.
(xxv) dipeptidylpeptidase inhibitor
    TMC-2A and the like.
(xxvi) TRK-530, TOK-8801
(xxvii) collagen agonist
    AI-200 and the like.
(xxviii) capsaicin cream
(xxix) hyaluronic acid derivative
    synvisc (hylan G-F 20), orthovisc and the like.
(xxx) glucosamine sulfate
(xxxi) amiprilose Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, anticonvulsant, antidepressant, antiallergic drug, cardiac, vasodilator, vasoconstrictor, antidiabetic drug, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent
A. sulfa drug
    sulfamethizole, sulfisoxazole, sulfamonomethoxine, sulfamethizole, salazosulfapyridine, silver sulfadiazine and the like.
B. quinoline antibacterial agent
    nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like.
C. antiphthisic
    isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
D. antiacidfast bacterium drug
    diaphenylsulfone, rifampicin and the like.
E. antiviral drug
    idoxuridine, acyclovir, vidarabine, gancyclovir and the like.
F. anti-HIV agent
    zidovudine, didanosine, zalcitabine, indinavir sulfate ethanolate, ritonavir and the like.
G. antispirochetele
H. antibiotic
    tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group [*Journal of Antibiotics* (J. Antibiotics), 38, 877–885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) Antifungal Agent
A. polyethylene antibiotic (e.g., amphotericin B, nystatin, trichomycin, etc.)
B. griseofulvin, pyrrolnitrin and the like.
C. cytosine metabolism antagonist (e.g., flucytosine, etc.)
D. imidazole derivative (e.g., econazole, clotrimazole, miconazole nitrate, bifonazole, croconazole, etc.)
E. triazole derivative (e.g. fluconazole, itraconazole, etc.)
F. thiocarbamic acid derivative (e.g. trinaphthol, etc.), and the like (3) Antiprotozoal Agent
    metronidazole, tinidazole, diethylcarbamazine citrate, quinine hydrochloride, quinine sulfate and the like.

(4) Antitussive and Expectorant Drug
    ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline, oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic (6-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine) and the like.

(6-2) General Anesthetic

A. inhalation anesthetic (e.g., ether, halothane, nitrous oxide, isoflurane, enflurane, etc.),
B. intravenous anesthetic (e.g., ketamine hydrochloride, droperidol, thiopental sodium, thiamylal sodium, pentobarbital, etc.) and the like.

(7) Antiulcer Drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) Antiarrhythmic Agent

A. Na channel blocker (e.g., quinidine, procainamide, disopyramide, ajmaline, lidocaine, mexiletine, phenytoin, etc.),
B. β-blocker (e.g., propranolol, alprenolol, bufetolol hydrochloride, oxprenolol, atenolol, acebutolol, metoprolol, bisoprolol, pindolol, carteolol, arotinolol hydrochloride, etc.),
C. K channel blocker (e.g., amiodarone, etc.),
D. Ca channel blocker (e.g., verapamil, diltiazem, etc.) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline, pentolinium, mecamylamine, ecarazine, clonidine, diltiazem, nifedipine, and the like.

(10) Anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug

6-O-(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Antihypolipidemic Drug clofibrate, ethyl 2-chloro-3-[4-(2-methyl-2-phenylpropoxy)-phenyl]propionate [*Chemical and Pharmaceutical Bulletin* (Chem. Pharm. Bull), 38, 2792–2796 (1990)], pravastatin, simvastatin, probucol, bezafibrate, clinofibrate, nicomol, cholestyramine, dextran sulfate sodium and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Anticonvulsant phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac trans-$\pi$-oxocamphor, terephyllol, aminophylline, etilefrine, dopamine, dobutamine, denopamine, aminophylline, bencirin, amrinone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine denopamine and the like.

(22) Antidiabetic Drug tolbutamide, chlorpropamide, acetohexamide, glibenclamide, tolazamide, acarbose, epalrestat, troglitazone, glucagon, glymidine, glipizide, phenformin, buformin, metformin and the like.

(23) Antinarcotic levallorphan, nalorphine, naloxone or a salt thereof and the like.

(24) (Fat-Soluble) Vitamin

A. vitamin A: vitamin $A_1$, vitamin $A_2$ and retinol palmitate
B. vitamin D: vitamin $D_1$, $D_2$, $D_3$, $D_4$ and $D_5$
C. vitamin E: $\alpha$-tocopherol, $\beta$-tocopherol, $\gamma$-tocopherol, $\delta$-tocopherol, dl-$\alpha$-tocopherol nicotinate
D. vitamin K: vitamin $K_1$, $K_2$, $K_3$ and $K_4$
E. folic acid (vitamin M) and the like.

(25) Vitamin Derivative various derivatives of vitamins, for example, vitamin $D_3$ derivatives such as 5,6-trans-cholecalciferol, 2,5-hydroxycholecalciferol, 1-$\alpha$-hydroxycholecalciferol and the like, vitamin $D_2$ derivatives such as 5,6-trans-ergocalciferol and the like, and the like.

(26) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.

(27) Therapeutic Agent for Pollakisuria/Anischuria flavoxate hydrochloride and the like.

(28) Therapeutic Agent for Atopic Dermatitis sodium cromoglicate and the like.

(29) Therapeutic Agent for Allergic Rhinitis sodium cromoglicate, chlorpheniramine maleate, alimemazine tartrate, clemastine fumarate, homochlorcyclizine hydrochloride, terfenadine, mequitazine and the like.

(30) Hypertensive Drug dopamine, dobutamine, denopamine, digitoxin, digoxin, methyldigoxin, lanatoside C, G-strophanthin and the like.

(31) Others hydroycam, diacerein, megestrol acetate, nicergoline, prostaglandins and the like.

By combining the compound of the present invention and a concomitant drug, a superior effect such as (1) the dose can be reduces as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

In the following present specification, a pharmaceutical agent comprising the compound of the present invention and a concomitant drug may be referred to as the "combination agent of the present invention".

As regards the use of the combination agent of the present invention, the administration time of the compound of the present invention and the concomitant drug is not restricted, and the compound of the present invention or the concomitant drug can be administered to an administration subject simultaneously, or may be administered at different times. In addition, the combination agent of the present invention can be used after synovectomy, after treatment with Prosorba column, after mononuclear cell therapy, and the like. The dosage of the concomitant drug may be determined according to the dose clinically used, and can be appropriately selected depending on an administration subject, administration route, disease, combination and the like.

The administration mode of the compound of the present invention and the concomitant drug of the present invention is not particularly restricted, and it is sufficient that the compound of the present invention and the concomitant drug are combined in administration. Examples of such administration mode include the following methods:

(1) The compound of the present invention and the concomitant drug are simultaneously produced to give a single preparation which is administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route only at the different times. (4) The compound of the present invention and the concomitant drug are separately produced to give two kinds of preparations which are administered simultaneously by the different administration routes. (5) The compound of the present invention and the concomitant drug are separately produced to give two kinds of preparations which are administered by the different administration routes only at different times (e.g., the compound of the present invention and the concomitant drug are administered in this order, or in the reverse order).

A combination agent of the present invention has low toxicity, and for example, the compound of the present invention and/or the above-mentioned concomitant drug can be mixed, according to a method known per se, with a pharmacologically acceptable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like). An injection can be administered by intravenous, intramuscular, subcutaneous or intraorgan route, or directly to the lesion.

As a pharmacologically acceptable carrier which may be used for preparing a preparation of a combination agent of the present invention, various conventional organic or inorganic carriers as pharmaceutical materials, such as excipient, lubricant, binder and disintegrating agent in solid preparations, or solvent, solubilizing agent, suspending agent, isotonizing agent, buffer and soothing agent in liquid preparations can be mentioned. Further, if needed, additives such as the conventional preservative, antioxidant, colorant, sweetening agent, adsorbing agent, wetting agent and the like can be appropriately used in an appropriate amount.

As an excipient, for example, lactose, sucrose, D-mannitol, starch, corn starch, microcrystalline cellulose, light anhydrous silicic acid and the like can be mentioned.

As a lubricant, for example, magnesium stearate, calcium stearate, talc, colloidal silica and the like can be mentioned.

As a binder, for example, microcrystalline cellulose, sucrose, D-mannitol, dextrin, hydroxypropylcellulose, hydroxypropylmethylcellulose, polyvinylpyrrolidone, starch, saccharose, gelatin, methylcellulose, sodium carboxymethylcellulose and the like can be mentioned.

As a disintegrating agent, for example, starch, carboxymethylcellulose, calcium carboxymethylcellulose, sodium carboxymethylstarch, L-hydroxypropylcellulose and the like can be mentioned.

As a solvent, for example, water for injection, alcohol, propylene glycol, macrogol, sesame oil, corn oil, olive oil and the like can be mentioned.

As a solubilizing agent, for example, polyethylene glycol, propylene glycol, D-mannitol, benzyl benzoate, ethanol, tris-aminomethane, cholesterol, triethanolamine, sodium carbonate, sodium citrate and the like can be mentioned.

As a suspending agent, for example, surfactants such as stearyl triethenolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydoxypropylcellulose and the like can be mentioned.

As an isotonizing agent, for example, glucose, D-sorbitol, sodium chloride, glycerin, D-mannitol and the like can be mentioned.

As a buffer, for example, buffering solutions such as phosphate, acetate, carbonate, citrate and the like can be mentioned.

As a soothing agent, for example, benzyl alcohol and the like can be mentioned.

As a preservative, for example, p-hydroxybenzoates, chlorobutanol, benzyl alcohol, phenethyl alcohol, dehydroacetic acid, sorbic acid and the like can be mentioned.

As an antioxidant, for example, sulfites, ascorbic acid, $\alpha$-tocopherol and the like can be mentioned.

As the coloring agent, for example, water-soluble food coal-tar dyes, water-insoluble lake dyes, natural pigments (e.g., β-carotene, chlorophiles, colcothar etc.) and the like can be mentioned.

As the sweetening agent, for example, saccharin sodium, dipotassium glycyrrhizinate, aspartam, stevia and the like can be mentioned.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to 100% by weight, preferably from about 0.1 to 50% by weight, further preferably from about 0.5 to 20% by weight, based on the preparation.

The content of the concomitant drug in the combination agent of the present invention differs depending on the form of a preparation, and usually from about 0.01 to 100% by weight, preferably from about 0.1 to 50% by weight, further preferably from about 0.5 to 20% by weight, based on the preparation.

The content of additives such as a carrier and the like in the combination agent of the present invention differs depending on the form of a preparation, and usually from about 1 to 99.99% by weight, preferably from about 10 to 90% by weight, based on the preparation.

In the case when the compound of the present invention and the concomitant drug are separately prepared respectively, the same contents may be adopted.

These preparations can be produced by a method known per se usually used in a preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-hydroxybenzoate, benzoic acid, methyl p-hydroxybenzoate, propyl p-hydroxybenzoate, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and molded into an oily injection.

In the case of a preparation for oral administration, an excipient (e.g., lactose, sucrose, starch and the like), a disintegrating agent (e.g., starch, calcium carbonate and the like), a binder (e.g., starch, acacia, carboxymethylcellulose, polyvinylpyrrolidone, hydroxpropylcellulose and the like), a lubricant (e.g., talc, magnesium stearate, polyethylene glycol 6000 and the like) and the like, for example, can be added to the compound of the present invention or the concomitant drug, according to a method known per se, and the mixture can be compression-molded, then if desirable, the molded product can be coated by a method known per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (methacrylic acid-acrylic acid copolymer, manufactured by Rohm, DE), pigment (e.g., iron oxide red, titanium dioxide, et.) and the like can be used. The preparation for oral administration may be any of a quick release preparation and a sustained release preparation.

For example, in the case of a suppository, the compound of the present invention and the concomitant drug can be made into an oily or aqueous solid, semisolid or liquid suppository according to a method known per se. As the oily substrate used in the above-mentioned composition, for example, glycerides of higher fatty acids [e.g., cacao butter, Witepsols (manufactured by Dynamite Nobel, DE), etc.], intermediate grade fatty acids [e.g., Miglyols (manufactured by Dynamite Nobel, DE), etc.], or vegetable oils (e.g., sesame oil, soy bean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release agent, sustained release microcapsules and the like are listed.

For obtaining a sustained release microcapsule, a method known per se can be adopted, and for example, it is preferably molded into a sustained release preparation shown in the following [2] before administration.

A compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The concomitant drug can be made into the above-mentioned drug form depending on the kind of the drug.

[1] An injection of the compound of the present invention or the concomitant drug, and preparation thereof, [2] a sustained release preparation or quick release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof.

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water. As the above-mentioned salts of benzoic acid and salicylic acid, for example, salts of alkali metals such as sodium, potassium and the like, salts of alkaline earth metals such as calcium, magnesium and the like, ammonium salts, meglumine salts, organic acid salts such as tromethamol etc., and the like are listed.

The concentration of the compound of the present invention or the concomitant drug in an injection is from 0.5 to 50% (w/v), preferably from about 3 to 20% (w/v). The concentration of a benzoate salt or/and salicylate salt is from 0.5 to 50% (w/v), preferably from 3 to 20% (w/v).

Into a preparation of the present invention, additives usually used in an injection, for example, a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, and the like), a dispersing agent (e.g., hydroxypropylmethylcellulose, dextrin, and the like), a pH regulator (e.g., hydrochloric acid, sodium hydroxide and the like), a preservative (e.g., ethyl p-hydroxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, can be appropriately compounded. These additives are generally compounded in a proportion usually used in an injection.

It is advantageous that pH of an injection is controlled from 2 to 12, preferably from 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously be heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation which is divided and administered multiple times.

[2] Sustained Release Preparation or Quick Release Preparation, and Preparation Thereof A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration for a single administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudragits (Rohm Pharma) such as Eudragit RS-100, RL-100, RS-30D, RL-30D, RL-PO, RS-PO (ethyl acrylate-methyl methacrylate-trimethyl chloride methacrylate-ammoniumethyl copolymer), Eudragit NE-30D (methyl methacrylate-ethyl acrylate copolymer), and the like, hardened oils such as hardened castor oil (e.g., Lovery wax (Freunt) and the like), waxes such as carnauba wax, fatty acid glycerin ester, paraffin and the like, polyglycerin fatty acid esters, and the like.

As the swellable polymer, polymers having an acidic dissociating group and showing pH dependent swelling are preferable, and polymers manifesting slight swelling in acidic regions such as in the stomach and greater swelling in neutral regions such as in the small intestine and the large intestine are preferable.

As such a polymer having an acidic dissociating group and showing pH dependent swelling, cross-linkable polyacrylic acid copolymers such as, for example, Carbomer 934P, 940, 941, 974P, 980, 1342 and the like, polycarbophil, calcium polycarbophil (last two are manufactured by BF Goodrich), Hibiswako 103, 104, 105, 304 (all are manufactured by Wako Pure Chemical Co., Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drug as exemplified below, then, coating the resulting nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to 2000 μm, further preferably, from about 500 to about 1400 μm.

Preparation of the nucleus can be effected by a usual production method. For example, a suitable excipient, binding agent, integrating agent, lubricant, stabilizer, anticoagulant, lubricant and the like are mixed into a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose and corn starch are preferable.

As the bonder, for example, polyvinyl alcohol, hydroxypropyl cellulose, polyethylene glycol, polyvinyl pyrrolidone, Pluronic F68, gum Arabic, gelatin, starch and the like are used. As the disintegrating agent, for example, carboxymethylcellulose calcium (ECG505), crosscarmelose sodium (Ac-Di-Sol), crosslinked polyvinylpyrrolidone (Crospovidone), lower substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose, waxes can be used, and the average particle size thereof is preferably from about 100 μm to about 1500 μm.

For separating a drug and a film agent contained in a nucleus, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are used. The protective agent may contain, as a stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be spray coated on a nucleus by, for example, a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer and hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick release preparation may be liquid (e.g., solution, suspension, emulsion and the like) or solid (e.g., particle, pill, tablet and the like). Oral agents and parenteral agents such as an injection and the like are used, and oral agents are preferable.

The quick release preparation, usually, may contain, in addition to an active component drug, also carriers, additives and excipients conventionally used in the production field (hereinafter, sometimes abbreviated as excipient). The preparation excipient used is not particularly restricted providing it is an excipient ordinarily used as a preparation excipient. For example, as the excipient for an oral solid preparation, lactose, starch, corn starch, crystalline cellulose (Acevil PH101, manufactured by Asahi Chemical Industry Co., Ltd., and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4% (w/w), preferably from about 20 to about 98.5% (w/w), further preferably from about 30 to about 97% (w/w), based on the total amount of the quick release preparation.

The content of a drug in the quick release preparation can be appropriately selected in the range from about 0.5 to about 95% (w/w), preferably from about 1 to about 60% (w/w) based on the total amount of the quick release preparation.

When the quick release preparation is an oral solid preparation, it usually contains, in addition to the above-mentioned components, also an integrating agent. As this integrating agent, there are used, for example, carboxymethylcellulose calcium (ECG-505, manufactured by Gotoku Yakuhin), crosscarmelose sodium (e.g., Actisol, manufactured by Asahi Chemical Industry Co., Ltd., and the like), Crospovidone (e.g., Kollidon CL, manufactured by BASF, and the like), lower substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Chemical Industry Co., Ltd.), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and compounding amount of a drug used, design of releasing property, and the like, and for example, from about 0.05 to about 30% (w/w), preferably from about 0.5 to about 15% (w/w), based on the total amount of the quick releasing agent.

When the quick release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., aerosil (Nippon Aerosil), and the like), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar coloring matter, caramel, iron oxide red, titanium oxide, riboflavins, and the like), if necessary, an appetizing agent (e.g., sweetening agent, aroma and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick releasing preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a quick release preparation is formed, for example, into a particle, it can be prepared, according to the same methods as in the above-mentioned method for preparing a nucleus of a sustained release preparation, by mixing the components using a vertical granulator, universal kneader (manufactured by Hata Tekkosho), fluidized bed granulator FD-5S (manufactured by Powrex), and the like, then, subjecting the mixture to a wet extrusion granulation method, fluidized bed granulation method and the like.

Thus obtained quick releasing preparation and sustained releasing preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increase in in vivo use efficiency, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., fine crystalline cellulose and the like) is preferable. As the water-dispersible polymer, gums (e.g., gum tragacanth, acacia gum, cyamoposis gum, and the like), alginates (e.g., sodium alginate, and the like), cellulose derivatives (e.g., methylcellulose, carboxymethylcellulose, hydroxymethylcellulose, hydroxypropylcellulose, hydroxypropylmethylcellulose and the like), gelatin, water-soluble starch, polyacrylic acids (e.g., Carbomer and the like), polymethacrylic acid, polyvinyl alcohol, polyethylene glycol, polyvinylpyrrolidone, polycarbofil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, is desirable, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast, to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbofil, carbopol and the like) may also be contained. In the casting, a solution is poured on the non-adhesive surface, spread to uniform thickness (preferably 10 to 1000 micron) by an application tool such as a doctor blade and the like, then, the solution is dried to form a film. It may be advantageous that thus formed film is dried at room temperature or under heat, and cut into given area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include animal proteins or vegetable proteins such as gelatins, dextrins and, soybean, wheat and psyllium seed protein and the like; rubber substances such as gum Arabic, guar gum, agar, xanthan gum and the like; polysaccharides; alginic acids; carboxymethylcelluloses; carageenans; dextrans; pectins; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such matrix forming agent may be present in addition to a surfactant, or may be present while a surfactant being excluded. The matrix forming agent aids to maintain the compound of the present invention or the concomitant drug in the solution or suspension in diffused condition, in addition to formation of the matrix.

The composition may contain secondary components such as preservative, antioxidant, surfactant, thickening agent, coloring agent, pH controlling agent, flavoring agent, sweetening agent, food taste masking agent and the like.

Preferable preservative includes, for example, p-hydroxybenzoic acid esters, chlorobutanol, benzyl alcohol, phenethyl alcohol, dehydroacetic acid, sorbic acid and the like. Preferable antioxidant includes, for example, sulfite, ascorbic acid and the like. Preferable surfactant includes, for example, polysorbate 80, macrogol and the like. Preferable thickening agents include, for example, natural rubbers, cellulose derivatives and the like. As the suitable coloring agent, red, black and yellow iron oxides, and FD & C dyes such as FD & C Blue 2, FD & C Red 40 and the like manufactured by Elis and Eberald can be mentioned. Examples of suitable flavoring agents include mint, raspberry, licorice, orange, lemon, grape fruit, caramel, vanilla, cherry, grape flavor and combinations thereof. Examples of suitable pH controlling agents include citric acid, tartaric acid, phosphoric acid, hydrochloric acid and maleic acid. Examples of suitable sweetening agents include aspartame, acesulfame K and thaumatin and the like. Examples of suitable food taste masking agents include sodium bicarbonate, ion exchange resin, cyclodextrin-containing compounds, adsorbent substances and microcapsulated apomorphine.

The preparation contains the compound of the present invention or a concomitant drug in an amount generally from about 0.1 to about 50% by weight, preferably from about 0.1 to about 30% by weight, and preferred are preparations (such as the above-mentioned sublingual agent, buccal and the like) which can dissolve 90% or more of the compound of the present invention or the concomitant drug (into water) within the time range of about 1 to about 60 minutes, preferably about 1 to about 15 minutes, more preferably about 2 to about 5 minutes, and intraoral quick disintegrating preparations which are disintegrated within the range of 1 to 60 seconds, preferably 1 to 30 seconds, further preferably 1 to 10 seconds, after placement in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably from about 10 to about 70% by weight. The content of the hydrophilic carrier agent in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to about 5% by weight. The above-mentioned preparation may further contain additives such as a coloring agent, sweetening agent, preservative and the like, if necessary.

The dosage of a combination agent of the present invention differs depending on the kind of the compound according to the present invention, age, body weight, condition, drug form, administration method, administration period and the like, and for example, for one sepsis patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or divided several times in a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times divided in a day.

For administration of a combination agent of the present invention, the compound of the present invention may be administered after administration of the concomitant drug or the concomitant drug may be administered after administration of the compound of the present invention, though they may be administered simultaneously. When administered at a time interval, the interval varies depending on the effective ingredient, drug form and administration method, and, for example, when the concomitant drug is administered first, a method in which the Compound of the present invention is administered within time range of from 1 minute to 3 days, preferably from 10 minutes to 1 day, more preferably from 15 minutes to 1 hour, after administration of the concomitant drug is exemplified. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is exemplified.

In a preferable administration method, for example, the concomitant drug which has been formed into an oral administration preparation is administered orally at a daily dose of about 0.001 to 200 mg/kg, and about 15 minutes after, the compound of the present invention which has been formed into an oral administration preparation is administered orally at a daily dose of about 0.005 to 100 mg/kg.

The present invention is further explained in detail by way of the following Reference Example, Examples, Formulation Examples and Experimental Examples but these are mere examples and do not limit the present invention and can be varied without departing the scope of the present invention.

The "room temperature" in the following Reference Examples and Examples indicates normally about 10° C. to about 35° C. "%" indicates percentage by weight unless otherwise indicated, provided that yield represents mol/mol %.

The method of genetic engineering described in the following Experimental Examples followed the method described in *Molecular Cloning* (Maniatis et al., Cold Spring Harbor Laboratory (1989)) or in protocol attached to the reagent.

Abbreviations used elsewhere mean the following:
s: singlet
d: doublet
t: triplet
q: quartet
dd: double doublet
ddd: double double doublet
dt: double triplet
br: broad J: coupling constant
Hz: Hertz
CDCl$_3$: deuterated chloroform
DMSO-d$_6$: dimethyl sulfoxide-d$_6$
$^1$H-NMR: proton nuclear magnetic resonance
Me: methyl In the Sequence Listing in the present specification, SEQ ID Nos. indicate the following sequences.
[SEQ ID No. 1]
Base sequence of primer JNK1-U.
[SEQ ID No. 2]
Base sequence of primer JNK1-L.
[SEQ ID No. 3]
Base sequence of primer MKK7-U.
[SEQ ID No. 4]
Base sequence of primer MKK7-L.
[SEQ ID No. 5]
Base sequence of primer CAM7-U.
[SEQ ID No. 6]
Base sequence of primer CAM7-L.
[SEQ ID No. 7]
Base sequence of primer c-Jun-U.
[SEQ ID No. 8]
Base sequence of primer c-Jun-L.

EXAMPLES

Reference Example 1

1-bromo-3-ethylbenzene

To an aqueous 50% sulfuric acid solution (43.6 g) containing 3-ethylaniline (10.0 g, 82.5 mmol) was added dropwise an aqueous solution (16.5 mL) of sodium nitrite (6.83 g, 99.0 mmol) at 0° C. over 30 min. The obtained reaction mixture was stirred at 0° C. for 45 min. A solution of this diazonium salt was added by small portions to a 48% hydrobromic acid solution (82.5 mL) containing copper(I) bromide (12.4 g, 86.6 mmol) with heating under gentle reflux. After the addition, the reaction mixture was heated under reflux for 30 min. The reaction mixture was cooled to room temperature and extracted with ethyl ether. The extract was washed successively with 1N aqueous sodium hydroxide solution and saturated brine, filtered, dried and concentrated. The residue was purified by silica gel column chromatography (hexane-ethyl acetate=20:1) to give the title compound (6.13 g, yield 40%).

Oil.
$^1$H-NMR (CDCl$_3$) δ: 1.23 (3H, t, J=7.5 Hz), 2.63 (2H, q, J=7.5 Hz), 7.11–7.20 (2H, m), 7.28–7.38 (2H, m).

Reference Example 2

In accordance with Reference Example 1 and using 3-(1-methylethyl)aniline instead of 3-ethylaniline, the following Reference Example compound 2 was synthesized.

Reference Example Compound 2

1-bromo-3-(1-methylethyl)benzene

Oil.
$^1$H-NMR (CDCl$_3$) δ: 1.24 (6H, d, J=7.0 Hz), 2.77–2.99 (1H, m), 7.03–7.16 (2H, m), 7.27–7.34 (1H, m), 7.37 (1H, s).

Reference Example 3

3-ethyl benzoic acid

Under an argon atmosphere, a solution of 1-bromo-3-ethylbenzene (5.1 g, 28 mmol) in tetrahydrofuran (45 mL) was added dropwise to a mixture of magnesium turnings (0.74 g, 31 mmol) in tetrahydrofuran (5.0 mL), and the mixture was stirred for 30 min. The reaction mixture was added to crushed dry ice and stirred for 1 hr. 1N Hydrochloric acid was added to the reaction mixture and the mixture was extracted with ethyl acetate. The extract was dried, filtered and concentrated. The residue was purified by silica gel column chromatography (hexane-ethyl acetate=5:1) to give the title compound (3.87 g, yield 93%).

Oil.
$^1$H-NMR (CDCl$_3$) δ: 1.28 (3H, t, J=7.5 Hz), 2.73 (2H, q, J=7.5 Hz), 7.34–7.50 (2H, m), 7.92–7.98 (2H, m).

Reference Example 4

In accordance with Reference Example 3 and using 1-bromo-3-(1-methylethyl)benzene and 1-bromo-4-fluoro-3-methylbenzene instead of 1-bromo-3-ethylbenzene, the following Reference Example compounds 4-1 and 4-2 were synthesized respectively.

Reference Example Compound 4-1

3-(1-methylethyl)benzoic acid

Oil.
$^1$H-NMR (CDCl$_3$) δ: 1.29 (6H, d, J=7.0 Hz), 2.98–3.06 (1H, m), 7.38–7.54 (2H, m), 7.90–8.02 (2H, m).

Reference Example Compound 4-2

4-fluoro-3-methylbenzoic acid melting point: 165–167° C.

Reference Example 5

3-ethylbenzoylchloride

3-Ethylbenzoic acid (9.40 g, 62.6 mmol) was slowly added to thionyl chloride (45 mL) at 0° C. and N,N-dimethylformamide (3 drops) was added dropwise. The obtained reaction mixture was heated under reflux for 2 hrs. The reaction mixture was concentrated and used for the next reaction without purification.

Reference Example 6

In accordance with Reference Example 5 and using 3-(1-methylethyl)benzoic acid and 4-fluoro-3-methylbenzoic acid instead of 3-ethylbenzoic acid, the following Reference Example compounds 6-1 and 6-2 were synthesized respectively.

Reference Example Compound 6-1

3-(1-methylethyl)benzoylchloride

Used for the next reaction without purification.

Reference Example Compound 6-2

4-fluoro-3-methylbenzoylchloride

Used for the next reaction without purification.

Reference Example 7

N-(4-chlorobenzoyl)propyleneimine

A solution of propyleneimine (12 mL, 0.15 mol) in tetrahydrofuran (160 mL) was added to 1N aqueous sodium hydroxide solution. To this mixture was added dropwise 4-chlorobenzoyl chloride (25 g, 0.14 mol) at 0° C. After the completion of the dropwise addition, the mixture was further stirred for 30 min. The reaction mixture was extracted with ethyl acetate. The extract was dried and the solvent was evaporated to give the title compound (25 g, yield 89%).

Oil.
$^1$H-NMR (CDCl$_3$) δ: 1.39 (3H, d, J=5.5 Hz), 2.15 (1H, d, J=2.9 Hz), 2.51–2.66 (2H, m), 7.39–7.47 (2H, m), 7.93–8.01 (2H, m).

Reference Example 8

In accordance with Reference Example 7 and using 3-chlorobenzoylchloride, 3-methylbenzoylchloride, 3-ethylbenzoylchloride, 3-(1-methylethyl)benzoylchloride, 4-fluoro-3-methylbenzoylchloride and 3-fluorobenzoylchloride instead of 4-chlorobenzoylchloride, the following Reference Example compounds 8-1 to 8-6 were synthesized respectively.

Reference Example Compound 8-1

N-(3-chlorobenzoyl)propyleneimine

Oil.
$^1$H-NMR (CDCl$_3$) δ: 1.40 (3H, d, J=5.1 Hz), 2.17 (1H, d, J=3.3 Hz), 2.53–2.68 (2H, m), 7.40 (1H, dd, J=7.7, 8.1 Hz), 7.53 (1H, ddd, J=1.5, 2.2, 8.1 Hz), 7.90 (1H, dt, J=7.7, 1.5 Hz), 8.00 (1H, dd, J=1.5, 2.2 Hz).

Reference Example Compound 8-2

N-(3-methylbenzoyl)priopyleneimine

Oil.
$^1$H-NMR (CDCl$_3$) δ: 1.39 (3H, d, J=5.5 Hz), 2.14 (1H, d, J=3.3 Hz), 2.41 (3H, s), 2.51–2.66 (2H, m), 7.32–7.39 (2H, m), 7.79–7.87 (2H, m).

Reference Example Compound 8-3

N-(3-ethylbenzoyl)propyleneimine

Oil.
$^1$H-NMR (CDCl$_3$) δ: 1.27 (3H, t, J=7.5 Hz), 1.40 (3H, d, J=5.5 Hz), 2.14 (1H, d, J=2.9 Hz), 2.52–2.61 (2H, m), 2.71 (2H, q, J=7.5 Hz), 7.32–7.41 (2H, m), 7.81–7.89 (2H, m).

Reference Example Compound 8-4

N-[3-(1-methylethyl)benzoyl]propyleneimine

Oil.
$^1$H-NMR (CDCl$_3$) δ: 1.29 (6H, d, J=7.0 Hz), 1.40 (3H, d, J=5.9 Hz), 2.14 (1H, d, J=3.7 Hz), 2.51–2.64 (2H, m), 2.87–3.10 (1H, m), 7.33–7.46 (2H, m), 7.84 (1H, dt, J=7.0, 1.8 Hz), 7.91 (1H, s).

Reference Example Compound 8-5

N-(4-fluoro-3-methylbenzoyl)propyleneimine

Oil.
$^1$H-NMR (CDCl$_3$) δ: 1.39 (3H, d, J=5.4 Hz), 2.14 (1H, d, J=3.4 Hz), 2.33 (s, 3H), 2.51–2.61 (2H, m), 7.06 (1H, t, J=8.8 Hz), 7.81–7.90 (2H, m).

Reference Example Compound 8-6

N-(3-fluorobenzoyl)propyleneimine

Oil.
$^1$H-NMR (CDCl$_3$) δ: 1.40 (3H, d, J=5.5 Hz), 2.16 (1H, d, J=3.3 Hz), 2.52–2.68 (2H, m), 7.25 (1H, ddd, J=1.1, 2.6, 8.4 Hz), 7.43 (1H, ddd, J=5.5, 7.7, 8.1 Hz), 7.69 (1H, ddd, J=1.5, 2.6, 8.1 Hz), 7.81 (1H, ddd, J=1.1, 1.5, 7.7 Hz).

Reference Example 9

2-fluoro-4-methylpyridine

The title compound was synthesized according to the method described in *Journal of Medicinal Chemistry*, vol. 33, pp. 1667–1675 (1990)
boiling point 82–86° C. (10 kPa).

Reference Example 10

2-tert-butoxycarbonylamino-4-methylpyridine

The title compound was synthesized according to the method described in *Synthesis*, pp. 877–882 (1996) or *Journal of Organic Chemistry*, vol. 61, pp. 4810–4811 (1996).

Reference Example 11

2-(2-fluoro-4-pyridyl)-1-(3-methylphenyl)ethanone

Under an argon atmosphere, a solution of diisopropylamine (44 mL, 0.31 mol) in anhydrous tetrahydrofuran (300 mL) was cooled to −78° C. and, with stirring, a solution of 1.6M n-butyl lithium in hexane (190 mL, 0.31 mol) was added dropwise. After the completion of the dropwise addition, the mixture was stirred for 10 min. and a solution of 2-fluoro-4-methylpyridine (34.5 g, 0.31 mol) in anhydrous tetrahydrofuran (30 mL) was added. The reaction mixture was stirred at −10° C. for 30 min. The reaction solution was cooled to −78° C. and a solution of N-(3-methylbenzoyl)propyleneimine (52 g, 0.30 mol) in anhydrous tetrahydrofuran (30 mL) was added dropwise. After the completion of the dropwise addition, the mixture was stirred at room temperature for 2 hrs. Water (100 mL) was added to the reaction mixture and the mixture was extracted with ethyl acetate. The extract was washed with water, dried and the solvent was evaporated. The residue was recrystallized from isopropyl ether to give the title compound (35 g, yield 52%).
melting point: 66–67° C.

Reference Example 12

In accordance with Reference Example 11 and using N-(3-chlorobenzoyl)propyleneimine instead of N-(3-methylbenzoyl)propyleneimine, the following Reference Example compound 12 was synthesized.

Reference Example Compound 12

1-(3-chlorophenyl)-2-(2-fluoro-4-pyridyl)ethanone melting point: 84–86° C.

Reference Example 13

2-(2-tert-butoxycarbonylamino-4-pyridyl)-1-(3-methylphenyl)ethanone

A solution of 2-tert-butoxycarbonylamino-4-methylpyridine (146 g, 0.700 mol) in anhydrous tetrahydrofuran (1.30 L) was cooled to −78° C. and, with stirring, a solution of 1.6 M n-butyl lithium in hexane (875 mL, 1.40 mol) was added dropwise. After the completion of the dropwise addition, the mixture was stirred at 0° C. for 30 min. and cooled to −78° C. A solution of N-(3-methylbenzoyl)propyleneimine (123 g, 0.700 mol) in anhydrous tetrahydrofuran (130 mL) was added dropwise. After the completion of the dropwise addition, the mixture was stirred at −78° C. for 1 hr., warmed to room temperature and stirred for 1 hr. Saturated brine (1.30 L) was added to the reaction mixture and the organic layer was separated. The aqueous layer was extracted with ethyl acetate and the combined organic layer was dried and concentrated. The crude crystals were recrystallized from ethyl acetate to give the title compound (185 g, yield 81%).

melting point: 144–146° C.

Reference Example 14

In accordance with Reference Example 13 and using N-(3-chlorobenzoyl)propyleneimine, N-[3-(1-methylethyl)benzoyl]propyleneimine, N-(4-fluoro-3-methylbenzoyl)propyleneimine, N-(3-fluorobenzoyl)propyleneimine, N-(4-chlorobenzoyl)propyleneimine and N-(3-ethylbenzoyl)propyleneimine instead of N-(3-methylbenzoyl)propyleneimine, the following Reference Example compounds 14-1 to 14-6 were synthesized respectively.

Reference Example Compound 14-1

2-(2-tert-butoxycarbonylamino-4-pyridyl)-1-(3-chlorophenyl)ethanone melting point: 152–153° C.

Reference Example Compound 14-2

2-(2-tert-butoxycarbonylamino-4-pyridyl)-1-[3-(1-methylethyl)phenyl]ethanone melting point: 176–177° C.

Reference Example Compound 14-3

2-(2-tert-butoxycarbonylamino-4-pyridyl)-1-(4-fluoro-3-methylphenyl)ethanone melting point: 143–144° C.

Reference Example Compound 14-4

2-(2-tert-butoxycarbonylamino-4-pyridyl)-1-(3-fluorophenyl)ethanone melting point: 164–165° C.

Reference Example Compound 14-5

2-(2-tert-butoxycarbonylamino-4-pyridyl)-1-(4-chlorophenyl)ethanone melting point: 155–156° C.

Reference Example Compound 14-6

2-(2-tert-butoxycarbonylamino-4-pyridyl)-1-(3-ethylphenyl)ethanone melting point: 122–123° C.

Reference Example 15

2-(2-amino-4-pyridyl)-1-(3-methylphenyl)ethanone 2-(2-tert-Butoxycarbonylamino-4-pyridyl)-1-(3-methylphenyl)ethanone (50.0 g, 0.153 mol) was added to 2N-hydrochloric acid (260 mL) and the mixture was stirred at 100° C. for 2 hrs. The reaction mixture was neutralized with aqueous sodium hydroxide solution and extracted with ethyl acetate. The extract was dried and concentrated. The crude crystals were washed with isopropyl ether to give the title compound (29.1 g, yield 84%).

melting point: 119–120° C.

Reference Example 16

In accordance with Reference Example 15 and using 2-(2-tert-butoxycarbonylamino-4-pyridyl)-1-(3-chlorophenyl)ethanone instead of 2-(2-tert-butoxycarbonylamino-4-pyridyl)-1-(3-methylphenyl)ethanone, the following Reference Example compound 16 was synthesized.

Reference Example Compound 16

2-(2-amino-4-pyridyl)-1-(3-chlorophenyl)ethanone melting point: 173–175° C.

Reference Example 17

N-[4-[2-(3-methylphenyl)-2-oxoethyl]-2-pyridyl]benzamide

To a solution of 2-(2-amino-4-pyridyl)-1-(3-methylphenyl)ethanone (24.0 g, 0.106 mol) in acetonitrile (500 mL) was added benzoylchloride (27.0 mL, 0.233 mol) at 0° C. Triethylamine (35.6 mL, 0.256 mol) was added dropwise to the obtained mixture and the mixture was stirred at room temperature for 4 hrs. Water was added to the reaction mixture and the precipitated solids were collected by filtration. The aqueous layer was extracted with ethyl acetate and the extract was washed with aqueous sodium hydrogen carbonate solution. The extract was dried and concentrated. The obtained residue and the solid were dissolved in a mixture of tetrahydrofuran (450 mL) and methanol (110 mL) and 1N aqueous sodium hydroxide solution (256 mL) was added. The reaction mixture was stirred for 2 hrs. and concentrated. The residue was extracted with ethyl acetate, dried and concentrated. The residue was purified by silica gel column chromatography (hexane-ethyl acetate=2:1), and the obtained oil was crystallized from ethyl ether to give the title compound (19.5 g, yield 56%).

melting point: 67–69° C.

Reference Example 18

In accordance with Reference Example 17 and using 2-(2-amino-4-pyridyl)-1-(3-chlorophenyl)ethanone instead of 2-(2-amino-4-pyridyl)-1-(3-methylphenyl)ethanone, the following Reference Example compound 18 was synthesized.

Reference Example Compound 18

N-[4-[2-(3-chlorophenyl)-2-oxoethyl]-2-pyridyl]benzamide melting point: 121–123° C.

Reference Example 19

2-(2-amino-4-pyridyl)-2-bromo-1-(3-methylphenyl)ethanone hydrobromide

To a solution of 2-(2-tert-butoxycarbonylamino-4-pyridyl)-1-(3-methylphenyl)ethanone (185 g, 0.566 mol) in acetic acid (400 mL) was added bromine (29.2 mL, 0.566 mol) and the mixture was stirred at 80° C. for 2 hrs. The reaction mixture was concentrated and the residue was crystallized from acetonitrile-ethyl acetate to give the title compound (171 g, yield 78%).

melting point: 182–185° C.

Reference Example 20

In accordance with Reference Example 19 and using 2-(2-fluoro-4-pyridyl)-1-(3-methylphenyl)ethanone, 1-(3-chlorophenyl)-2-(2-fluoro-4-pyridyl)ethanone, 2-(2-tert-butoxycarbonylamino-4-pyridyl)-1-(3-chlorophenyl)ethanone, 2-(2-tert-butoxycarbonylamino-4-pyridyl)-1-[3-(1-methylethyl)phenyl]ethanone, 2-(2-tert-butoxycarbonylamino-4-pyridyl)-1-(3-fluorophenyl)ethanone, 2-(2-tert-butoxycarbonylamino-4-pyridyl)-1-(4-chlorophenyl)ethanone, 2-(2-tert-butoxycarbonylamino-4-pyridyl)-1-(3-ethylphenyl)ethanone and 2-(2-tert-butoxycarbonylamino-4-pyridyl)-1-(4-fluoro-3-methylphenyl)ethanone instead of 2-(2-tert-butoxycarbonylamino-4-pyridyl)-1-(3-methylphenyl)ethanone, the following Reference Example compounds 20-1 to 20-8 were synthesized respectively.

Reference Example Compound 20-1

2-bromo-2-(2-fluoro-4-pyridyl)-1-(3-methylphenyl)ethanone hydrobromide

Used for the next reaction without purification.

Reference Example Compound 20-2

2-bromo-1-(3-chlorophenyl)-2-(2-fluoro-4-pyridyl)ethanone hydrobromide

Amorphous Powder
$^1$H-NMR (DMSO-$d_6$) δ: 7.19 (1H, s), 7.38 (1H, s), 7.52–7.56 (1H, m), 7.64 (1H, t, J=8.0 Hz), 7.77–7.82 (1H, m), 8.05–8.09 (1H, m), 8.16 (1H, t, J=1.8 Hz), 8.32 (1H, d, J=5.2 Hz), 10.23 (1H, br s).

Reference Example Compound 20-3

2-(2-amino-4-pyridyl)-2-bromo-1-(3-chlorophenyl)ethanone hydrobromide melting point: 199–200° C.

Reference Example Compound 20-4

2-(2-amino-4-pyridyl)-2-bromo-1-[3-(1-methylethyl)phenyl]ethanone hydrobromide

Amorphous Powder
$^1$H-NMR (DMSO-$d_6$) δ: 1.24 (6H, d, J=6.6 Hz), 3.00 (1H, septet, J=6.6 Hz), 7.15 (1H, s), 7.17 (1H, s), 7.46–7.65 (2H, m), 7.88–7.98 (4H, m), 8.09 (1H, br s).

Reference Example Compound 20-5

2-(2-amino-4-pyridyl)-2-bromo-1-(3-fluorophenyl)ethanone hydrobromide melting point: 206–207° C.

Reference Example Compound 20-6

2-(2-amino-4-pyridyl)-2-bromo-1-(4-chlorophenyl)ethanone hydrobromide melting point: 202–203° C.

Reference Example Compound 20-7

2-(2-amino-4-pyridyl)-2-bromo-1-(3-ethylphenyl)ethanone hydrobromide melting point: 46–47° C.

Reference Example Compound 20-8

2-(2-amino-4-pyridyl)-2-bromo-1-(4-fluoro-3-methylphenyl)ethanone hydrobromide melting point: 225–226° C.

Reference Example 21

N-[4-[1-bromo-2-(3-methylphenyl)-2-oxoethyl]-2-pyridyl]benzamide hydrobromide

To a solution of N-[4-[2-(3-methylphenyl)-2-oxoethyl]-2-pyridyl]benzamide (19.0 g, 57.5 mmol) in acetic acid (60 mL) was added dropwise bromine (3.0 mL, 57.5 mmol) at room temperature over 1 hr., and the reaction mixture was stirred for 2 hrs. The precipitated crude crystals were collected by filtration and washed with ethyl acetate to give the title compound (25.4 g, yield 90%).

melting point: 203–206° C.

Reference Example 22

In accordance with Reference Example 21 and using N-[4-[2-(3-chlorophenyl)-2-oxoethyl]-2-pyridyl]benzamide instead of N-[4-[2-(3-methylphenyl)-2-oxoethyl]-2-pyridyl]benzamide, the following Reference Example compound 22 was synthesized.

Reference Example Compound 22

N-[4-[1-bromo-2-(3-chlorophenyl)-2-oxoethyl]-2-pyridyl]benzamide hydrobromide melting point: 212–213° C.

Reference Example 23

Thiobutylamide

Butyronitrile (10.0 g, 145 mol) was dissolved in a 4N hydrogen chloride in ethyl acetate solution (100 mL). To this solution was added O,O-diethyl phosphorodithioate (26.7 mL, 0.160 mol), and the mixture was stirred at room temperature for 22 hrs. Water (100 mL) was added to the reaction mixture, and the mixture was extracted with ethyl acetate. The filtrate was washed with saturated brine and aqueous sodium hydrogen carbonate solution, dried, and the solvent was evaporated. The residue was purified by silica gel column chromatography (hexane-ethyl acetate=1:1) to give the title compound (6.68 g, yield 45%).

Oil.

$^1$H-NMR (CDCl$_3$) δ: 0.99 (3H, t, J=7.6 Hz), 1.72–1.93 (2H, m), 2.64 (2H, t, J=7.6 Hz), 7.02 (1H, br s), 7.77 (1H, br s).

Reference Example 24

In accordance with Reference Example 23 and using 1-methylpiperidine-4-cerbonitrile instead of butyronitrile, the following Reference Example compound 24 was synthesized.

Reference Example Compound 24

1-methylpiperidine-4-carbothioamide melting point: 216–220° C.

Reference Example 25

[5-(2-fluoro-4-pyridyl)-4-(3-methylphenyl)-1,3-thiazol-2-yl]amine

To a mixture of 2-bromo-2-(2-fluoro-4-pyridyl)-1-(3-methylphenyl)ethanone hydrobromide [synthesized according to Reference Example 19 using 2-(2-fluoro-4-pyridyl)-1-(3-methylphenyl)ethanbne (8.46 g, 36.9 mmol) instead of 2-(2-tert-butoxycarbonylamino-4-pyridyl)-1-(3methylphenyl) ethanone] and thiourea (3.03 g, 39.8 mmol) in acetonitrile (50 mL) was added triethylamine (5.2 mL, 37.3 mmol), and the mixture was stirred at 80° C. for 2 hrs. Aqueous sodium hydrogen carbonate solution was poured into the reaction mixture and the precipitated solids were collected by filtration. The obtained solid was washed with water and dried. Crude crystals were recrystallized from ethanol to give the title compound (3.67 g, yield 35%).

melting point: 214–218° C.

Reference Example 26

2-ethyl-5-(2-fluoro-4-pyridyl)-4-(3-methylphenyl)-1,3-thiazole

A solution of 2-bromo-2-(2-fluoro-4-pyridyl)-1-(3-methylphenyl)ethanone hydrobromide (11 g, 29 mmol) and thiopropionamide (2.7 g, 30 mmol) in N,N-dimethylformamide (30 mL) was stirred at room temperature for 14 hrs. Aqueous sodium hydrogen carbonate solution was poured into the reaction mixture, and the mixture was extracted with ethyl acetate. The extract was washed with water, dried and the solvent was evaporated. The residue was purified by silica gel column chromatography (hexane-ethyl acetate=4:1) to give the title compound (3.3 g, yield 38%).

Oil.

$^1$H-NMR (CDCl$_3$) δ: 1.64 (3H, t, J=7.6 Hz), 2.34 (3H, s), 3.10 (2H, q, J=7.6 Hz), 6.84–6.86 (1H, m), 7.05–7.09 (1H, m), 7.13–7.25 (3H, m), 7.37 (1H, s), 8.10 (1H, d, J=5.6 Hz).

Reference Example 27

In accordance with Reference Example 26 and using 2-bromo-2-(2-fluoro-4-pyridyl)-1-(3-chlorophenyl)ethanone hydrobromide instead of 2-bromo-2-(2-fluoro-4-pyridyl)-1-(3-methylphenyl)ethanone hydrobromide, the following Reference Example compound 27 was synthesized.

Reference Example Compound 27

2-ethyl-5 (2-fluoro-4-pyridyl)-4-(3-chlorophenyl)-1,3-thiazole melting point: 102–103° C.

Reference Example 28

4-[2-ethyl-4-(3-methylphenyl)-1,3-thiazol-5-yl]-2-pyridylamine

A solution of 2-(2-amino-4-pyridyl)-2-bromo-1-(3-methylphenyl)ethanone hydrobromide (125 g, 0.323 mol) and thiopropionamide (28 g, 0.314 mol) in N,N-dimethylformamide (1200 mL) was stirred at room temperature for 14 hrs. The solvent was evaporated under reduced pressure. Aqueous sodium hydrogen carbonate solution was poured into the residue and the mixture was extracted with ethyl acetate. The extract was washed with saturated aqueous sodium hydrogen carbonate solution, dried and concentrated. Crude crystals were washed with hexane-ethyl acetate=1:1 to give the title compound (76.0 g, yield 82%).

melting point: 144–146° C.

Reference Example 29

In accordance with Reference Example 28 and using thiobutylamide instead of thiopropionamide, the following Reference Example compound 29 was synthesized.

Reference Example Compound 29

4-[4-(3-methylphenyl)-2-propyl-1,3-thiazol-5-yl]-2-pyridylamine melting point: 113–115° C.

Reference Example 30

In accordance with Reference Example 28 and using 2-(2-amino-4-pyridyl)-2-bromo-1-(3-fluorophenyl)ethanone hydrobromide, 2-(2-amino-4-pyridyl)-2-bromo-1-(4-chlorophenyl)ethanone hydrobromide, 2-(2-amino-4-pyridyl)-2-bromo-1-(3-ethylphenyl)ethanone hydrobromide, 2-(2-amino-4-pyridyl)-2-bromo-1-(4-fluoro-3-methylphenyl)ethanone hydrobromide and 2-(2-amino-4-pyridyl)-2-bromo-1-[3-(1-methylethyl)phenyl]ethanone hydrobromide instead of 2-(2-amino-4-pyridyl)-2-bromo-1-(3-methylphenyl)ethanone hydrobromide, the following Reference Example compounds 30-1 to 30-5 were synthesized respectively.

Reference Example Compound 30-1

4-[2-ethyl-4-(3-fluorophenyl)-1,3-thiazol-5-yl]-2-pyridylamine melting point: 153–154° C.

Reference Example Compound 30-2

4-[4-(4-chlorophenyl)-2-ethyl-1,3-thiazol-5-yl]-2-pyridylamine melting point: 136–137° C.

Reference Example Compound 30-3

4-[2-ethyl-4-(3-ethylphenyl)-1,3-thiazol-5-yl]-2-pyridylamine melting point: 128–129° C.

Reference Example Compound 30-4

4-[2-ethyl-4-(4-fluoro-3-methylphenyl)-1,3-thiazol-5-yl]-2-pyridylamine melting point: 134–135° C.

Reference Example Compound 30-5

4-[2-ethyl-4-[3-(1-methylethyl)phenyl]-1,3-thiazol-5-yl]-2-pyridylamine melting point: 80–81° C.

Reference Example 31

[5-(2-benzylamino-4-pyridyl)-4-(3-methylphenyl)-1,3-thiazol-2-yl]amine

A mixture of [5-(2-fluoro-4-pyridyl)-4-(3-methylphenyl)-1,3-thiazol-2-yl]amine (0.29 g, 1.0 mmol) and benzylamine (1.2 mL, 11 mmol) was stirred at 150° C. for 3 hrs. The reaction mixture was cooled to room temperature, saturated aqueous sodium hydrogen carbonate solution was added and the mixture was extracted with ethyl acetate. The extract was washed with water, dried and concentrated. The residue was purified by silica gel column chromatography (hexane-ethyl acetate=1:1) to give the title compound (0.16 g, yield 41%).

melting point: 178–179° C.

Reference Example 32

In accordance with Reference Example 31 and using cyclohexylamine and cyclopentylamine instead of benzylamine, the following Reference Example compounds 32-1 and 32-2 were synthesized respectively.

Reference Example Compound 32-1

[5-(2-cyclohexylamino-4-pyridyl)-4-(3-methylphenyl)-1,3-thiazol-2-yl]amine melting point: 168–169° C.

Reference Example Compound 32-2

[5-(2-cyclopentylamino-4-pyridyl)-4-(3-methylphenyl)-1,3-thiazol-2-yl]amine melting point: 169–170° C.

Reference Example 33

N-cyclopentyl-4-[2-ethyl-4-(3-methylphenyl)-1,3-thiazol-5-yl]2-pyridylamine

A mixture of 2-ethyl-5-(2-fluoro-4-pyridyl)-4-(3-methylphenyl)-1,3-thiazole (0.48 g, 1.6 mmol) and cyclopentylamine (1.6 mL, 16 mmol) was heated under reflux for 14 hrs. The reaction mixture was cooled to room temperature, saturated aqueous sodium hydrogen carbonate solution was added, and the mixture was extracted with ethyl acetate. The extract was washed with water, dried and concentrated. The obtained crude crystals were recrystallized from ethyl acetate to give the title compound (0.19 g, yield 33%).

melting point: 117–118° C.

Reference Example 34

4-[4-(3-chlorophenyl)-2-ethyl-1,3-thiazol-5-yl]-N-[(1S)-1-phenylethyl]-2-pyridylamine hydrochloride A mixture of 4-(3-chlorophenyl)-2-ethyl-5-(2-fluoro-4-pyridyl)-1,3-thiazole (0.35 g, 1.1 mmol) and (S)-1-phenylethylamine (1.4 mL, 11 mmol) was stirred at 150° C. for 16 hrs. The reaction mixture was cooled to room temperature, saturated aqueous sodium hydrogen carbonate solution was added and the mixture was extracted with ethyl acetate. The extract was washed with water, dried and concentrated. The obtained oil was treated with 10% hydrogen chloride-methanol to give the title compound (0.27 g, yield 56%).

melting point: 165–166° C.

Reference Example 35

N-[4-[2-ethyl-4-(3-methylphenyl)-1,3-thiazol-5-yl]-2-pyridyl]phenylacetamide

To a solution of 4-[2-ethyl-4-(3-methylphenyl)-1,3-thiazol-5-yl]-2-pyridylamine (0.80 g, 2.7 mmol) in tetrahydrofuran (8 mL) was added phenylacetyl chloride (0.47 mL, 3.0 mmol), and triethylamine (0.41 mL, 3.0 mmol) was added to the obtained mixture. The reaction mixture was stirred at room temperature for 2 hrs. Saturated aqueous sodium hydrogen carbonate solution was added and the mixture was extracted with ethyl acetate. The extract was washed with saturated brine, dried and concentrated. The residue was purified by silica gel column chromatography (hexane-ethyl acetate 20:1–4:1) and crystallized from isopropyl ether to give the title compound (0.75 g, yield 67%).

melting point: 107–108° C.

Reference Example 36

In accordance with Reference-Example 35 and using propionylchloride instead of phenylacetylchloride, the following Reference Example compound 36 was synthesized.

Reference Example Compound 36

N-[4-[2-ethyl-4-(3-methylphenyl)-1,3-thiazol-5-yl]-2-pyridyl]propionamide melting point: 103–104° C.

Reference Example 37

In accordance with Reference Example 35 and using 4-[4-(3-methylphenyl)-2-propyl-1,3-thiazol-5-yl]-2-pyridylamine, 4-[4-(4-chlorophenyl)-2-ethyl-1,3-thiazol-5-yl]-2-pyridylamine, 4-[2-ethyl-4-(3-fluorophenyl)-1,3-thiazol-5-yl]-2-pyridylamine, 4-[2-ethyl-4-(3-ethylphenyl)-1,3-thiazol-5-yl]-2-pyridylamine and 4-[2-ethyl-4-[3-(1-methylethyl)phenyl]-1,3-thiazol-5-yl]-2-pyridylamine instead of 4-[2-ethyl-4-(3-methylphenyl)-1,3-thiazol-5-yl]-2-pyridylamine, the following Reference Example compounds 37-1 to 37-5 were synthesized respectively.

Reference Example Compound 37-1

N-[4-[2-propyl-4-(3-methylphenyl)-1,3-thiazol-5-yl]-2-pyridyl]phenylacetamide melting point: 109–111° C.

Reference Example Compound 37-2

N-[4-[4-(4-chlorophenyl)-2-ethyl-1,3-thiazol-5-yl]-2-pyridyl]phenylacetamide melting point: 150–151° C.

Reference Example Compound 37-3

N-[4-[2-ethyl-4-(3-fluorophenyl)-1,3-thiazol-5-yl]-2-pyridyl]phenylacetamide melting point: 113–114° C.

Reference Example Compound 37-4

N-[4-[2-ethyl-4-(3-ethylphenyl)-1,3-thiazol-5-yl]-2-pyridyl]phenylacetamide melting point: 155–156° C.

Reference Example Compound 37-5

N-[4-[2-ethyl-4-[3-(1-methylethyl)phenyl]-1,3-thiazol-5-yl]-2-pyridyl]phenylacetamide melting point: 112–113° C.

Reference Example 38

N-[4-[2-ethyl-4-(3-methylphenyl)-1,3-thiazol-5-yl]-2-pyridyl]-2-thiophenecarboxamide To a solution of 4-[2-ethyl-4-(3-methylphenyl)-1,3-thiazol-5-yl]-2-pyridylamine (0.50 g, 1.7 mmol) in tetrahydrofuran (10 mL) was added 2-thiophenecarbonyl chloride (0.36 mL, 3.4 mmol), and triethylamine (0.52 mL, 3.7 mmol) was added to the obtained mixture. The reaction mixture was stirred at room temperature for 10 min. Saturated aqueous sodium hydrogen carbonate solution was added and the mixture was extracted with ethyl acetate. The extract was washed with saturated brine, dried and concentrated. The residue was dissolved in conc. hydrochloric acid (5 mL) and the mixture was stirred at 40° C. for 14 hrs. The reaction mixture was neutralized with aqueous sodium hydroxide solution and extracted with ethyl acetate. The extract was dried and concentrated. The residue was purified by silica gel column chromatography (hexane-ethyl acetate=4:1) and crystallized from isopropyl ether-hexane to give the title compound (0.56 g, yield 82%).

melting point: 102–103° C.

Reference Example 39

In accordance with Reference Example 3.8 and using 3-thiophenecarbonyl chloride, 4-methoxybenzoyl chloride, 4-methylbenzoyl chloride, 3-fluorobenzoyl chloride, 4-fluorobenzoyl chloride and 3,5-dichlorobenzoyl chloride instead of 2-thiophenecarbonyl chloride, the following Reference Example compounds 39-1 to 39-6 were synthesized respectively.

Reference Example Compound 39-1

N-[4-[2-ethyl-4-(3-methylphenyl)-1,3-thiazol-5-yl]-2-pyridyl]-3-thiophenecarboxamide melting point: 99–101° C.

Reference Example Compound 39-2

N-[4-[2-ethyl-4-(3-methylphenyl)-1,3-thiazol-5-yl]-2-pyridyl]-4-methoxybenzamide melting point: 124–125° C.

Reference Example Compound 39-3

N-[4-[2-ethyl-4-(3-methylphenyl)-1,3-thiazol-5-yl]-2-pyridyl]-4-methylbenzamide melting point: 105–106° C.

Reference Example Compound 39-4

N-[4-[2-ethyl-4-(3-methylphenyl)-1,3-thiazol-5-yl]-2-pyridyl]-3-fluorobenzamide melting point: 101–102° C.

Reference Example Compound 39-5

N-[4-[2-ethyl-4-(3-methylphenyl)-1,3-thiazol-5-yl]-2-pyridyl]-4-fluorobenzamide melting point: 110–111° C.

Reference Example Compound 39-6

3,5-dichloro-N-[4-[2-ethyl-4-(3-methylphenyl)-1,3-thiazol-5-yl]-2-pyridyl]benzamide melting point: 77–78° C.

Reference Example 40

In accordance with Reference Example 38 and using benzoylchloride instead of 2-thiophenecarbonylchloride, and 4-[4-(4-chlorophenyl)-2-ethyl-1,3-thiazol-5-yl]-2-pyridylamine and 4-[2-ethyl-4-(4-fluoro-3-methylphenyl)-1,3-thiazol-5-yl]-2-pyridylamine instead of 4-[2-ethyl-4-(3-methylphenyl)-1,3-thiazol-5-yl]-2-pyridylamine, the following Reference Example compounds 40-1 and 40-2 were synthesized respectively.

Reference Example Compound 40-1

N-[4-[4-(4-chlorophenyl)-2-ethyl-1,3-thiazol-5-yl]-2-pyridyl]benzamide melting point: 138–139° C.

Reference Example Compound 40-2

N-[4-[2-ethyl-4-(4-fluoro-3-methylphenyl)-1,3-thiazol-5-yl]-2-pyridyl]benzamide melting point: 108–109° C.

Reference Example 41

N-[5-(2-benzylamino-4-pyridyl)-4-(3-methylphenyl)-1,3-thiazol-2-yl]nicotinamide

To a solution of [5-(2-benzylamino-4-pyridyl)-4-(3-methylphenyl)-1,3-thiazol-2-yl]amine (0.52 g, 1.4 mmol) and 4-dimethylaminopyridine (0.051 g, 0.42 mmol) in N,N-dimethylacetamide (10 mL) was added nicotinoyl chloride hydrochloride (0.37 g, 2.1 mmol), and the mixture was stirred at 80° C. for 14 hrs. Into the reaction mixture was poured aqueous sodium hydrogen carbonate solution and the mixture was extracted with ethyl acetate. The extract was washed with saturated brine, dried and concentrated. The resulting crystals were crystallized from isopropyl ether to give the title compound (0.28 g, yield 59%).

melting point: 220–222° C.

Reference Example 42

6-chloro-N-[5-(2-cyclopentylamino-4-pyridyl)-4-(3-methylphenyl)-1,3-thiazol-2-yl]nicotinamide To a solution of [5-(2-cyclopentylamino-4-pyridyl)-4-(3-methylphenyl)-1,3-thiazol-2-yl]amine (0.50 g, 1.4 mmol) and 4-dimethylaminopyridine (0.052 g, 0.43 mmol) in N,N-dimethylacetamide (10 mL) was added 6-chloronicotinoyl chloride hydrochloride (0.46 g, 2.1 mmol), and the mixture was stirred at 80° C. for 14 hrs. Into the reaction mixture was poured aqueous sodium hydrogen carbonate solution and the mixture was extracted with ethyl acetate. The extract was washed with saturated brine, dried and concentrated. The residue was purified by silica gel column chromatography (hexane-ethyl acetate 4:1) and the resulting crystals were recrystallized from ethanol to give the title compound (0.30 g, yield 42%).

melting point: 211–212° C.

Reference Example 43

In accordance with Reference Example 42 and using [5-(2-cyclohexylamino-4-pyridyl)-4-(3-methylphenyl)-1,3-thiazol-2-yl]amine instead of [5-(2-cyclopentylamino-4-pyridyl)-4-(3-methylphenyl)-1,3-thiazol-2-yl]amine, the following Reference Example compound 43 was synthesized.

Reference Example Compound 43

6-chloro-N-[5-(2-cyclohexylamino-4-pyridyl)-4-(3-methylphenyl)-1,3-thiazol-2-yl]nicotinamide melting point: 255–256° C.

Reference Example 44

N-[4-[4-(3-methylphenyl)-2-(1-methylpiperidin-4-yl)-1,3-thiazol-5-yl]-2-pyridyl]benzamide A solution of N-[4-[1-bromo-2-(3-methylphenyl)-2-oxoethyl]-2-pyridyl]benzamide hydrobromide (0.60 g, 1.2 mmol) and 1-methylpiperidine-4-carbothioamide (0.19 g, 1.18 mmol) in N,N-dimethylformamide (20 mL) was stirred at room temperature for 14 hrs. Into the reaction mixture was poured aqueous sodium hydrogen carbonate solution and the mixture was extracted with ethyl acetate. The extract was washed with saturated aqueous sodium hydrogen carbonate solution, dried and concentrated. The residue was purified by column chromatography (packing: Chromatorex NH DM1020 (product name, manufactured by Fuji Silysia Chemical Ltd.), hexane-ethyl acetate=2:1) and the resulting crystals were recrystallized from ethyl acetate to give the title compound (0.26 g, yield 46%).

melting point: 151–152° C.

Reference Example 45

In accordance with Reference Example 44 and using N-[4-[1-bromo-2-(3-chlorophenyl)-2-oxoethyl]-2-pyridyl]benzamide hydrobromide instead of N-[4-[1-bromo-2-(3-methylphenyl)-2-oxoethyl]-2-pyridyl]benzamide hydrobromide, the following Reference Example compound 45 was synthesized.

Reference Example Compound 45

N-[4-[4-(3-chlorophenyl)-2-(1-methylpiperidin-4-yl)-1,3-thiazol-5-yl]-2-pyridyl]benzamide melting point: 125–127° C.

The compounds produced in Reference Examples 32–45 are shown in Tables 1 and 2.

TABLE 1
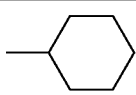
| Ex. compound | R³ | W | Z | R¹ | R² | adduct | melting point/° C. |
|---|---|---|---|---|---|---|---|
| 32-1 | 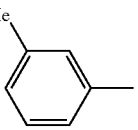 | — | —NH— | —NH₂ | 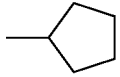 Me | | 168–169 |
| 32-2 | 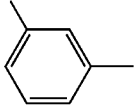 | — | —NH— | —NH₂ | 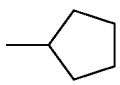 Me | | 169–170 |
| 33 | 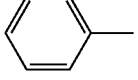 | — | —NH— | —CH₂Me | 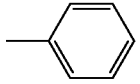 Me | | 117–118 |
| 34 | 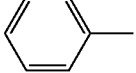 | (S) —CHMe— | —NH— | —CH₂Me | 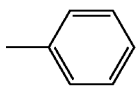 Cl | HCl | 165–166 |
| 35 | 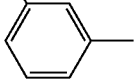 | —CH₂CO— | —NH— | —CH₂Me | 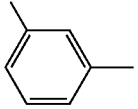 Me | | 107–108 |
| 36 | —CH₂Me | —CO— | —NH— | —CH₂Me | 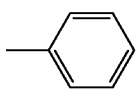 Me | | 103–104 |
| 37-1 | 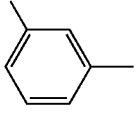 | —CH₂CO— | —NH— | —(CH₂)₂Me | 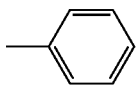 Me | | 109–111 |
| 37-2 | 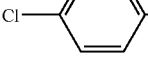 | —CH₂CO— | —NH— | —CH₂Me | 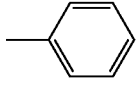 Cl | | 150–151 |
| 37-3 | 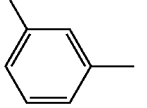 | —CH₂CO— | —NH— | —CH₂Me | F | | 113–114 |

TABLE 1-continued
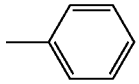
| Ex. compound | R³ | W | Z | R¹ | R² | adduct | melting point/° C. |
|---|---|---|---|---|---|---|---|
| 37-4 | 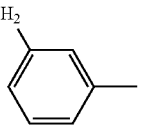 | —CH₂CO— | —NH— | —CH₂Me | 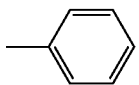 | | 155–156 |
| 37-5 | 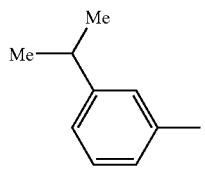 | —CH₂CO— | —NH— | —CH₂Me | 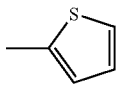 | | 112–113 |
| 38 | 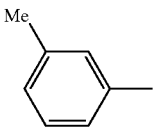 | —CO— | —NH— | —CH₂Me | 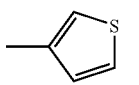 | | 102–103 |
| 39-1 | 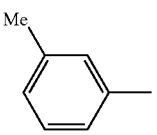 | —CO— | —NH— | —CH₂Me | 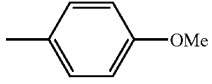 | | 99–101 |
TABLE 2
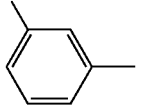
| Ex. compound | R³ | W | Z | R¹ | R² | melting point/° C. |
|---|---|---|---|---|---|---|
| 39-2 | 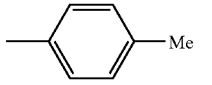 | —CO— | —NH— | —CH₂Me | 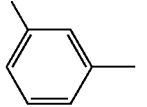 | 124–125 |
| 39-3 | 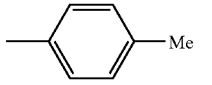 | —CO— | —NH— | —CH₂Me | 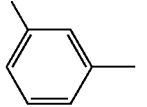 | 105–106 |

TABLE 2-continued
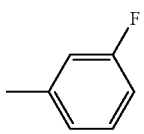
| Ex. compound | R³ | W | Z | R¹ | R² | melting point/° C. |
|---|---|---|---|---|---|---|
| 39-4 | 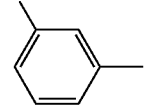 | —CO— | —NH— | —CH₂Me | 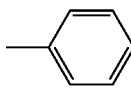 | 101–102 |
| 39-5 | 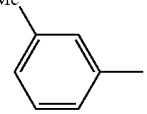 | —CO— | —NH— | —CH₂Me | 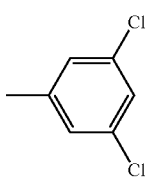 | 110–111 |
| 39-6 | 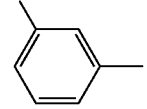 | —CO— | —NH— | —CH₂Me | 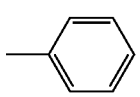 | 77–78 |
| 40-1 | 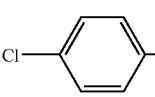 | —CO— | —NH— | —CH₂Me | 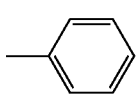 | 138–139 |
| 40-2 | 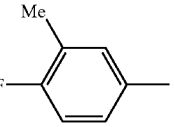 | —CO— | —NH— | —CH₂Me | 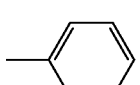 | 108–109 |
| 41 | 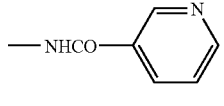 | —CH₂— | —NH— | 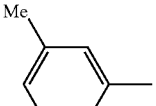 | 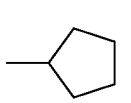 | 220–222 |
| 42 | 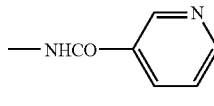 | — | —NH— | 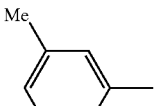 | 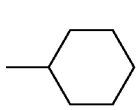 | 211–212 |
| 43 | 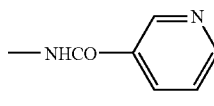 | — | —NH— | 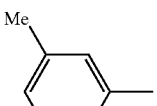 | 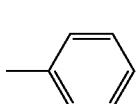 | 255–256 |
| 44 | 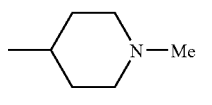 | —CO— | —NH— | 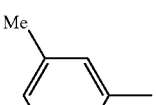 |  | 151–152 |

TABLE 2-continued

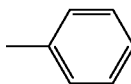

| Ex. compound | R³ | W | Z | R¹ | R² | melting point/° C. |
|---|---|---|---|---|---|---|
| 45 | 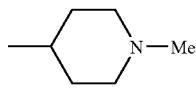 | —CO— | —NH— | 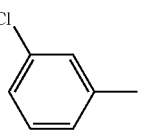 | | 125–127 |

Reference Example 46

In accordance with Reference Example 7 and using benzoylchloride, 3-methoxybenzoylchloride, 4-methylbenzoylchloride, 3-bromobenzoylchloride, 2-thiophenecarbonylchloride and 4-fluorobenzoylchloride instead of 4-chlorobenzoylchloride, the following Reference Example compounds 46-1 to 46-6 were synthesized respectively.

Reference Example Compound 46-1

N-benzoylpropyleneimine

Oil.
$^1$H-NMR (CDCl$_3$) δ: 1.40 (3H, d, J=6.0 Hz), 2.15 (1H, d, J=3.2 Hz), 2.52–2.67 (2H, m), 7.40–7.61 (3H, m), 7.98–8.07 (2H, m).

Reference Example Compound 46-2

N-(3-methoxybenzoyl)propyleneimine

Oil.
$^1$H-NMR (CDCl$_3$) δ: 1.40 (3H, d, J=5.9 Hz), 2.14 (1H, d, J=2.9 Hz), 2.52–2.65 (2H, m), 3.86 (3H, s), 7.10 (1H, ddd, J=1.1, 2.6, 8.4 Hz), 7.37 (1H, dd, J=8.4, 7.3 Hz), 7.55 (1H, dd, J=1.5, 2.6 Hz), 7.63 (1H, ddd, J=1.1, 1.5, 7.3 Hz).

Reference Example Compound 46-3

N-(4-methylbenzoyl)propyleneimine

Oil.
$^1$H-NMR (CDCl$_3$) δ: 1.39 (3H, d, J=5.5 Hz), 2.12 (1H, d, J=2.9 Hz), 2.42 (3H, s), 2.50–2.62 (2H, m), 7.25 (2H, d, J=8.1 Hz), 7.92 (2H, d, J=8.1 Hz).

Reference Example Compound 46-4

N-(3-bromobenzoyl)propyleneimine

Oil.
$^1$H-NMR (CDCl$_3$) δ: 1.40 (3H, d, J=5.2 Hz), 2.16–2.18 (1H, m), 2.53–2.65 (2H, m), 7.34 (1H, t, J=7.9 Hz), 7.65–7.71 (1H, m), 7.95 (1H, d, J=7.9 Hz), 8.16 (1H, t, J=1.8 Hz).

Reference Example Compound 46-5

N-(2-thiophenecarbonyl)propyleneimine

Oil.
$^1$H-NMR (CDCl$_3$) δ: 1.43 (3H, d, J=5.2 Hz), 2.14 (1H, d, J=3.6 Hz), 2.56–2.72 (2H, m), 7.08–7.16 (1H, m), 7.53–7.60 (1H, m), 7.75–7.81 (1H, m).

Reference Example Compound 46-6

N-(4-fluorobenzoyl)propyleneimine

Oil.
$^1$H-NMR (CDCl$_3$) δ: 1.39 (3H, d, J=5.2 Hz), 2.14–2.15 (1H, m), 2.52–2.63 (2H, m), 7.08–7.19 (2H, m), 8.00–8.10 (2H, m).

Reference Example 47

In accordance with Reference Example 11 and using N-(4-fluorobenzoyl)propyleneimine instead of N-(3-methylbenzoyl)propyleneimine, the following Reference Example compound 47 was synthesized.

Reference Example Compound 47

1-(4-fluorophenyl)-2-(2-fluoro-4-pyridyl) ethanone melting point: 100–101° C.

Reference Example 48

In accordance with Reference Example 13 and using N-benzoylpropyleneimine, N-(4-fluorobenzoyl)propyleneimine, N-(3-bromobenzoyl)propyleneimine, N-(2-thiophenecarbonyl)propyleneimine, N-(3-methoxybenzoyl)propyleneimine and N-(4-methylbenzoyl)propyleneimine instead of N-(3-methylbenzoyl)propyleneimine, the following Reference Example compounds 48-1 to 48-6 were synthesized respectively.

Reference Example Compound 48-1

2-(2-tert-butoxycarbonylamino-4-pyridyl)-1-phenylethanone melting point: 162–163° C.

Reference Example Compound 48-2

2-(2-tert-butoxycarbonylamino-4-pyridyl)-1-(4-fluorophenyl)ethanone melting point: 139–141° C.

Reference Example Compound 48-3

1-(3-bromophenyl)-2-(2-tert-butoxycarbonylamino-4-pyridyl)ethanone melting point: 132–133° C.

Reference Example Compound 48-4

2-(2-tert-butoxycarbonylamino-4-pyridyl)-1-(2-thienyl)ethanone melting point: 161–162° C.

Reference Example Compound 48-5

2-(2-tert-butoxycarbonylamino-4-pyridyl)-1-(3-methoxyphenyl)ethanone melting point: 99–100° C.

Reference Example Compound 48-6

2-(2-tert-butoxycarbonylamino-4-pyridyl)-1-(4-methylphenyl)ethanone melting point: 137–138° C.

Reference Example 49

In accordance with Reference Example 19 and using 1-(4-fluorophenyl)-2-(2-fluoro-4-pyridyl)ethanone, 1-(3-bromophenyl)-2-(2-tert-butoxycarbonylamino-4-pyridyl)ethanone, 2-(2-tert-butoxycarbonylamino-4-pyridyl)-1-(4-fluorophenyl)ethanone, 2-(2-tert-butoxycarbonylamino-4-pyridyl)-1-(4-methylphenyl)ethanone, 2-(2-tert-butoxycarbonylamino-4-pyridyl)-1-phenylethanone, 2-(2-tert-butoxycarbonylamino-4-pyridyl)-1-(2-thienyl)ethanone and 2-(2-tert-butoxycarbonylamino-4-pyridyl)-1-(3-methoxyphenyl)ethanone instead of 2-(2-tert-butoxycarbonylamino-4-pyridyl)-1-(3-methylphenyl)ethanone, the following Reference Example compounds 49-1 to 49-7 were synthesized respectively.

Reference Example Compound 49-1

2-bromo-1-(4-fluorophenyl)-2-(2-fluoro-4-pyridyl)ethanone hydrobromide

Amorphous Powder
$^1$H-NMR (DMSO-d$_6$) δ: 7.16 (1H, s), 7.37–7.54 (4H, m), 8.11–8.24 (2H, m), 8.30 (1H, d, J=5.0 Hz).

Reference Example Compound 49-2

2-(2-amino-4-pyridyl)-2-bromo-1-(3-bromophenyl)ethanone hydrobromide

Used for the next reaction without purification.

Reference Example compound 49-3

2-(2-amino-4-pyridyl)-2-bromo-1-(4-fluorophenyl)ethanone hydrobromide melting point: 171–172° C.

Reference Example Compound 49-4

2-(2-amino-4-pyridyl)-2-bromo-1-(4-methylphenyl)ethanone hydrobromide melting point: 200–201° C.

Reference Example Compound 49-5

2-(2-amino-4-pyridyl)-2-bromo-1-phenylethanone hydrobromide melting point: 155–156° C.

Reference Example Compound 49-6

2-(2-amino-4-pyridyl)-2-bromo-1-(2-thienyl)ethanone hydrobromide

Amorphous Powder
$^1$H-NMR (DMSO-d$_6$) δ: 6.96–7.09 (2H, m), 7.24 (1H, s), 7.32–7.43 (1H, m), 7.98 (1H, d, J=6.6 Hz), 8.12–8.36 (2H, m).

Reference Example Compound 49-7

2-(2-amino-4-pyridyl)-2-bromo-1-(3-methoxyphenyl)ethanone hydrobromide melting point: 205–206° C.

Reference Example 50

In accordance with Reference Example 23 and using 4-(methylthio)benzonitrile, valeronitrile and ethylcyanoacetate instead of butyronitrile, the following Reference Example compounds 50-1 to 50-3 were synthesized respectively.

Reference Example Compound 50-1

4-(methylthio)thiobenzamide melting point: 176–178° C.

Reference Example Compound 50-2

Thiovaleramide

Oil.
$^1$H-NMR (CDCl$_3$) δ: 0.94 (3H, t, J=7.3 Hz), 1.31–1.49 (2H, m), 1.68–1.83 (2H, m), 2.67 (2H, t, J=7.7 Hz), 6.92 (1H, br s), 7.73 (1H, br s).

Reference Example Compound-50-3 ethyl 3-amino-3-thioxopropanate

Oil.
¹H-NMR (CDCl₃) δ: 1.31 (3H, t, J=7.1 Hz), 3.85 (2H, s), 4.22 (2H, q, J=7.1 Hz), 7.74 (1H, br s), 8.92 (1H, br s).

Reference Example 51

Ethyl 2-amino-2-thioxoacetate

To a solution of ethyl oxamate (3.21 g, 27.4 mmol) in anhydrous tetrahydrofuran (100 mL) was added Lawesson's reagent (6.10 g, 15.1 mmol), and the mixture was heated under reflux for 2 hrs. The mixture was cooled to room temperature, and saturated aqueous sodium hydrogen carbonate solution was added to the reaction mixture. The mixture was extracted with ethyl acetate. The extract was dried and the solvent was evaporated. The residue was purified by silica gel column chromatography (hexane-ethyl acetate=4:1-2:1) and crystallized from isopropyl ether to give the title compound (2.92 g, yield 80%).
melting point: 60–62° C.

Reference Example 52

In accordance with Reference Example 25 and using 2-bromo-1-(4-fluorophenyl)-2-(2-fluoro-4-pyridyl)ethanone hydrobromide instead of 2-bromo-2-(2-fluoro-4-pyridyl)-1-(3-methylphenyl)ethanone hydrobromide, the following Reference Example compound 52 was synthesized.

Reference Example Compound 52

[4-(4-fluorophenyl)-5-(2-fluoro-4-pyridyl)-1,3-thiazol-2-yl]amine melting point: 243–245° C.

Reference Example 53

In accordance with Reference Example 25 and using N-methylthiourea instead of thiourea, the following Reference Example compound 53 was synthesized.

Reference Example Compound 53

N-methyl-[5-(2-fluoro-4-pyridyl)-4-(3-methylphenyl)-1,3-thiazol-2-yl]amine melting point: 186–187° C.

Reference Example 54

In accordance with Reference Example 28 and using thiovaleramide, ethyl 2-amino-2-thioxoacetate and ethyl 3-amino-3-thioxopropanate instead of thiopropionamide, the following Reference Example compounds 54-1 to 54-3 were synthesized respectively.

Reference Example Compound 54-1

4-[2-butyl-4-(3-methylphenyl)-1,3-thiazol-5-yl]-2-pyridylamine

Oil.
¹H-NMR (CDCl₃) δ: 0.98 (3H, t, J=7.3 Hz), 1.39–1.59 (2H, m), 1.76–1.92 (2H, m), 2.34 (3H, s), 3.04 (2H, t, J=7.4 Hz), 4.14 (2H, br s), 6.44 (1H, s), 6.56 (1H, dd, J=1.5, 5.4 Hz), 7.09–7.26 (3H, m), 7.41 (1H, s), 7.96 (1H, d, J=5.4 Hz).

Reference Example Compound 54-2 ethyl [5-(2-amino-4-pyridyl)-4-(3-methylphenyl)-1,3-thiazol-2-yl]carboxylate melting point: 147–148° C.

Reference Example Compound 54-3 ethyl [5-(2-amino-4-pyridyl)-4-(3-methylphenyl)-1,3-thiazol-2-yl]acetate melting point: 128–129° C.

Reference Example 55

In accordance with Reference Example 28 and using 2-(2-amino-4-pyridyl)-2-bromo-1-(3-chlorophenyl)ethanone hydrobromide, 2-(2-amino-4-pyridyl)-2-bromo-1-(3-bromophenyl)ethanone hydrobromide, 2-(2-amino-4-pyridyl)-2-bromo-1-(4-fluorophenyl)ethanone hydrobromide, 2-(2-amino-4-pyridyl)-2-bromo-1-(4-methylphenyl)ethanone hydrobromide, 2-(2-amino-4-pyridyl)-2-bromo-1-phenylethanone hydrobromide, 2-(2-amino-4-pyridyl)-2-bromo-1-(2-thienyl)ethanone hydrobromide and 2-(2-amino-4-pyridyl)-2-bromo-1-(3-methoxyphenyl)ethanone hydrobromide instead of 2-(2-amino-4-pyridyl)-2-bromo-1-(3-methylphenyl)ethanone hydrobromide, the following Reference Example compounds 55-1 to 55-7 were synthesized respectively.

Reference Example Compound 55-1

4-[4-(3-chlorophenyl)-2-ethyl-1,3-thiazol-5-yl]-2-pyridylamine melting point: 132–133° C.

Reference Example Compound 55-2

4-[4-(3-bromophenyl)-2-ethyl-1,3-thiazol-5-yl]-2-pyridylamine melting point: 132–134° C.

Reference Example Compound 55-3

4-[2-ethyl-4-(4-fluorophenyl)-1,3-thiazol-5-yl]-2-pyridylamine melting point: 140–141° C.

Reference Example Compound 55-4

4-[2-ethyl-4-(4-methylphenyl)-1,3-thiazol-5-yl]-2-pyridylamine melting point: 126–127° C.

Reference Example Compound 55-5

4-(2-ethyl-4-phenyl-1,3-thiazol-5-yl)-2-pyridylamine melting point: 158–159° C.

Reference Example Compound 55-6

4-[2-ethyl-4-(2-thienyl)-1,3-thiazol-5-yl]-2-pyridylamine melting point: 159–160° C.

Reference Example Compound 55-7

4-[2-ethyl-4-(3-methoxyphenyl)-1,3-thiazol-5-yl]-2-pyridylamine melting point: 130–131° C.

Reference Example 56

In accordance with Reference Example 29 and using 2-(2-amino-4-pyridyl)-2-bromo-1-(3-chlorophenyl)ethanone hydrobromide instead of 2-(2-amino-4-pyridyl)-2-bromo-1-(3-methylphenyl)ethanone hydrobromide, the following Reference Example compound 56 was synthesized.

Reference Example Compound 56

4-[4-(3-chlorophenyl)-2-propyl-1,3-thiazol-5-yl]-2-pyridylamine melting point: 99–100° C.

Reference Example 57

In accordance with Reference Example 56 and using 4-(methylthio)thiobenzamide and ethyl 3-amino-3-thioxopropanate instead of thiobutylamide, the following Reference Example compounds 57-1 and 57-2 were synthesized respectively.

Reference Example Compound 57-1

4-[4-(3-chlorophenyl)-2-[4-(methylthio)phenyl]-1,3-thiazol-5-yl]-2-pyridylamine melting point: 183–184° C.

Reference Example Compound 57-2 ethyl [5-(2-amino-4-pyridyl)-4-(3-chlorophenyl)-1,3-thiazol-2-yl]acetate melting point: 154–155° C.

Reference Example 58

[5-(2-amino-4-pyridyl)-4-(3-methylphenyl)-1,3-thiazol-2-yl]acetic acid

To a suspension of ethyl [5-(2-amino-4-pyridyl)-4-(3-methylphenyl)-1,3-thiazol-2-yl]acetate (7.00 g, 19.8 mmol) in ethanol (40 mL) was added 1N aqueous sodium hydroxide solution (40 mL), and the mixture was stirred at room temperature for 2 hrs. The reaction mixture was neutralized with 2N hydrochloric acid (20 mL) and the resulting solid was collected by filtration. The crude product was washed with water and dried to give the title compound (6.10 g, yield 95%).

melting point: 132–133° C.

Reference Example 59

In accordance with Reference Example 58 and using ethyl [5-(2-amino-4-pyridyl)-4-(3-methylphenyl)-1,3-thiazol-2-yl]carboxylate and ethyl [5-(2-amino-4-pyridyl)-4-(3-chlorophenyl)-1,3-thiazol-2-yl]acetate instead of ethyl [5-(2-amino-4-pyridyl)-4-(3-methylphenyl)-1,3-thiazol-2-yl]acetate, the following Reference Example compounds 59-1 and 59-2 were synthesized respectively.

Reference Example Compound 59-1

5-(2-amino-4-pyridyl)-4-(3-methylphenyl)-1,3-thiazole-2-carboxylic acid melting point: 135–136° C.

Reference Example Compound 59-2

[5-(2-amino-4-pyridyl)-4-(3-chlorophenyl)-1,3-thiazol-2-yl]acetic acid

Used for the next reaction without isolation.

Reference Example 60

4-[2-methyl-4-(3-methylphenyl)-1,3-thiazol-5-yl]-2-pyridylamine

[5-(2-Amino-4-pyridyl)-4-(3-methylphenyl)-1,3-thiazol-2-yl]acetic acid (5.0 g, 15 mmol) was stirred at 150° C. for 15 min and cooled to room temperature. The crude product was purified by silica gel column chromatography (ethyl acetate) and subjected to recrystallization from ethyl acetate to give the title compound (4.0 g, yield 93%).

melting point: 152–153° C.

Reference Example 61

In accordance with Reference Example 60 and using 5-(2-amino-4-pyridyl)-4-(3-methylphenyl)-1,3-thiazole-2-carboxylic acid and [5-(2-amino-4-pyridyl)-4-(3-chlorophenyl)-1,3-thiazol-2-yl]acetic acid instead of [5-(2-amino-4-pyridyl)-4-(3-methylphenyl)-1,3-thiazol-2-yl]acetic acid, the following Reference Example compounds 61-1 and 61-2 were synthesized respectively.

Reference Example Compound 61-1

4-[4-(3-methylphenyl)-1,3-thiazol-5-yl]-2-pyridylamine melting point: 91–92° C.

Reference Example Compound 61-2

4-[4-(3-chlorophenyl)-2-methyl-1,3-thiazol-5-yl]-2-pyridylamine melting point: 142–143° C.

Reference Example 62

In accordance with Reference Example 33 and using N-methyl-[5-(2-fluoro-4-pyridyl)-4-(3-methylphenyl)-1,3-thiazol-2-yl]amine instead of 2-ethyl-5-(2-fluoro-4-pyridyl)-4-(3-methylphenyl)-1,3-thiazole, the following Reference Example compound 62 was synthesized.

Reference Example Compound 62

N-methyl-[5-(2-cyclopentylamino-4-pyridyl)-4-(3-methylphenyl)-1,3-thiazol-2-yl]amine melting point: 170–172° C.

Reference Example 63

In accordance with Reference Example 62 and using cyclohexylamine instead of cyclopentylamine, the following Reference Example compound 63 was synthesized.

Reference Example Compound 63

N-methyl-[5-(2-cyclohexylamino-4-pyridyl)-4-(3-methylphenyl)-1,3-thiazol-2-yl]amine melting point: 211–212° C.

Reference Example 64

In accordance with Reference Example 63 and using [4-(4-fluorophenyl)-5-(2-fluoro-4-pyridyl)-1,3-thiazol-2-yl]amine, 2-ethyl-5-(2-fluoro-4-pyridyl)-4-(3-methylphenyl)-1,3-thiazole and 4-(3-chlorophenyl)-2-ethyl-5-(2-fluoro-4-pyridyl)-1,3-thiazole instead of N-methyl-[5-(2-fluoro-4-pyridyl)-4-(3-methylphenyl)-1,3-thiazol-2-yl]amine, the following Reference Example compounds 64-1 to 64-3 were synthesized respectively.

Reference Example Compound 64-1

[5-(2-cyclohexylamino-4-pyridyl)-4-(4-fluorophenyl)-1,3-thiazol-2-yl]amine melting point: 194–195° C.

Reference Example Compound 64-2

N-cyclohexyl-4-[2-ethyl-4-(3-methylphenyl)-1,3-thiazol-5-yl]-2-pyridylamine melting point: 110–112° C.

Reference Example Compound 64-3

N-cyclohexyl-4-[4-(3-chlorophenyl)-2-ethyl-1,3-thiazol-5-yl]-2-pyridylamine melting point: 106–107° C.

Reference Example 65

In accordance with Reference Example 41 and using N-cyclopentyl-4-[2-ethyl-4-(3-methylphenyl)-1,3-thiazol-5-yl]-2-pyridylamine, N-cyclohexyl-4-[2-ethyl-4-(3-methylphenyl)-1,3-thiazol-5-yl]-2-pyridylamine, N-methyl-[5-(2-cyclopentylamino-4-pyridyl)-4-(3-methylphenyl)-1,3-thiazol-2-yl]amine and N-methyl-[5-(2-cyclohexylamino-4-pyridyl)-4-(3-methylphenyl)-1,3-thiazol-2-yl]amine instead of [5-(2-benzylamino-4-pyridyl)-4-(3-methylphenyl)-1,3-thiazol-2-yl]amine, the following Reference Example compounds 65-1 to 65-4 were synthesized respectively.

Reference Example Compound 65-1

N-[5-(2-cyclopentylamino-4-pyridyl)-4-(3-methylphenyl)-1,3-thiazol-2-yl]nicotinamide melting point: 201–203° C.

Reference Example Compound 65-2

N-[5-(2-cyclohexylamino-4-pyridyl)-4-(3-methylphenyl)-1,3-thiazol-2-yl]nicotinamide melting point: 215–216° C.

Reference Example Compound 65-3

N-methyl-N-[5-(2-cyclopentylamino-4-pyridyl)-4-(3-methylphenyl)-1,3-thiazol-2-yl]nicotinamide melting point: 135–136° C.

Reference Example Compound 65-4

N-methyl-N-[5-(2-cyclohexylamino-4-pyridyl)-4-(3-methylphenyl)-1,3-thiazol-2-yl]nicotinamide melting point: 148–149° C.

Reference Example 66

In accordance with Reference Example 42 and using 6-methylnicotinoyl chloride hydrochloride and 6-methoxynicotinoyl chloride hydrochloride instead of 6-chloronicotinoyl chloride hydrochloride, the following Reference Example compounds 66-1 and 66-2 were synthesized respectively.

Reference Example Compound 66-1

N-[5-(2-cyclopentylamino-4-pyridyl)-4-(3-methylphenyl)-1,3-thiazol-2-yl]-6-methylnicotinamide melting point: 213–214° C.

Reference Example Compound 66-2

N-[5-(2-cyclopentylamino-4-pyridyl)-4-(3-methylphenyl)-1,3-thiazol-2-yl]-6-methoxynicotinamide melting point: 219–221° C.

Reference Example 67

In accordance with Reference Example 66 and using [5-(2-cyclohexylamino-4-pyridyl)-4-(3-methylphenyl)-1,3-thiazol-2-yl]amine and N-methyl-[5-(2-cyclopentylamino-4-pyridyl)-4-(3-methylphenyl)-1,3-thiazol-2-yl]amine instead of [5-(2-cyclopentylamino-4-pyridyl)-4-(3-methylphenyl)-1,3-thiazol-2-yl]amine, the following Reference Example compounds 67-1 to 67-3 were synthesized respectively.

Reference Example Compound 67-1

N-[5-(2-cyclohexylamino-4-pyridyl)-4-(3-methylphenyl)-1,3-thiazol-2-yl]-6-methylnicotinamide melting point: 242–243° C.

Reference Example Compound 67-2

N-[5-(2-cyclopentylamino-4-pyridyl)-4-(3-methylphenyl)-1,3-thiazol-2-yl]-N,6-dimethylnicotinamide melting point: 176–177° C.

Reference Example Compound 67-3

N-[5-(2-cyclohexylamino-4-pyridyl)-4-(3-methylphenyl)-1,3-thiazol-2-yl]-6-methoxynicotinamide melting point: 191–192° C.

Reference Example 68

In accordance with Reference Example 35 and using 4-[4-(3-bromophenyl)-2-ethyl-1,3-thiazol-5-yl]-2-pyridylamine, 4-[4-(3-chlorophenyl)-2-ethyl-1,3-thiazol-5-yl]-2-pyridylamine, 4-[4-(3-chlorophenyl)-2-methyl-1,3-thiazol-5-yl]-2-pyridylamine, 4-[2-butyl-4-(3-methylphenyl)-1,3-thiazol-5-yl]-2-pyridylamine, 4-[2-methyl-4-(3-methylphenyl)-1,3-thiazol-5-yl]-2-pyridylamine, 4-[4-(3-methylphenyl)-1,3-thiazol-5-yl]-2-pyridylamine, 4-[2-ethyl-4-(4-fluorophenyl)-1,3-thiazol-5-yl]-2-pyridylamine, 4-[2-ethyl-4-(4-methylphenyl)-1,3-thiazol-5-yl]-2-pyridylamine, 4-(2-ethyl-4-phenyl-1,3-thiazol-5-yl)-2-pyridylamine and 4-[2-ethyl-4-(3-methoxyphenyl)-1,3-thiazol-5-yl]-2-pyridylamine instead of 4-[2-ethyl-4-(3-methylphenyl)-1,3-thiazol-5-yl]-2-pyridylamine, the following Reference Example compounds 68-1 to 68-10 were synthesized respectively.

Reference Example Compound 68-1

N-[4-[4-(3-bromophenyl)-2-ethyl-1,3-thiazol-5-yl]-2-pyridyl]phenylacetamide melting point: 97–99° C.

Reference Example Compound 68-2

N-[4-[4-(3-chlorophenyl)-2-ethyl-1,3-thiazol-5-yl]-2-pyridyl]phenylacetamide melting point: 111–112° C.

Reference Example Compound 68-3

N-[4-[4-(3-chlorophenyl)-2-methyl-1,3-thiazol-5-yl]-2-pyridyl]phenylacetamide melting point: 99–101° C.

Reference Example Compound 68-4

N-[4-[2-butyl-4-(3-methylphenyl)-1,3-thiazol-5-yl]-2-pyridyl]phenylacetamide melting point: 92–93° C.

Reference Example Compound 68-5

N-[4-[2-methyl-4-(3-methylphenyl)-1,3-thiazol-5-yl]-2-pyridyl]phenylacetamide melting point: 114–115° C.

Reference Example Compound 68-6

N-[4-[4-(3-methylphenyl)-1,3-thiazol-5-yl]-2-pyridyl]phenylacetamide melting point: 135–136° C.

Reference Example Compound 68-7

N-[4-[2-ethyl-4-(4-fluorophenyl)-1,3-thiazol-5-yl]-2-pyridyl]phenylacetamide melting point: 178–179° C.

Reference Example Compound 68-8

N-[4-[2-ethyl-4-(4-methylphenyl)-1,3-thiazol-5-yl]-2-pyridyl]phenylacetamide melting point: 128–129° C.

Reference Example Compound 68-9

N-[4-(2-ethyl-4-phenyl-1,3-thiazol-5-yl)-2-pyridyl]phenylacetamide melting point: 162–163° C.

Reference Example Compound 68-10

N-[4-[2-ethyl-4-(3-methoxyphenyl)-1,3-thiazol-5-yl]-2-pyridyl]phenylacetamide melting point: 128–129° C.

Reference Example 69

In accordance with Reference Example 36 and using 4-[4-(3-chlorophenyl)-2-ethyl-1,3-thiazol-5-yl]-2-pyridylamine, 4-[4-(3-chlorophenyl)-2-methyl-1,3-thiazol-5-yl]-2-pyridylamine, 4-[4-(3-chlorophenyl)-2-propyl-1,3-thiazol-5-yl]-2-pyridylamine, 4-[4-(3-chlorophenyl)-2-[4-(methylthio)phenyl]-1,3-thiazol-5-yl]-2-pyridylamine and 4-[2-ethyl-4-(2-thienyl)-1,3-thiazol-5-yl]-2-pyridylamine instead of 4-[2-ethyl-4-(3-methylphenyl)-1,3-thiazol-5-yl]-2-pyridylamine, the following Reference Example compounds 69-1 to 69-5 were synthesized respectively.

Reference Example Compound 69-1

N-[4-[4-(3-chlorophenyl)-2-ethyl-1,3-thiazol-5-yl]-2-pyridyl]propionamide melting point: 132–133° C.

Reference Example Compound 69-2

N-[4-[4-(3-chlorophenyl)-2-methyl-1,3-thiazol-5-yl]-2-pyridyl]propionamide melting point: 134–135° C.

Reference Example Compound 69-3

N-[4-[4-(3-chlorophenyl)-2-propyl-1,3-thiazol-5-yl]-2-pyridyl]propionamide melting point: 103–104° C.

Reference Example Compound 69-4

N-[4-[4-(3-chlorophenyl)-2-[4-(methylthio)phenyl]-1,3-thiazol-5-yl]-2-pyridyl]propionamide melting point: 187–188° C.

Reference Example Compound 69-5

N-[4-[2-ethyl-4-(2-thienyl)-1,3-thiazol-5-yl]-2-pyridyl]propionamide melting point: 187–188° C.

Reference Example 70

In accordance with Reference Example 69 and using acetylchloride, benzoylchloride and pivaloylchloride instead of propionylchloride, the following Reference Example compounds 70-1 to 70-5 were synthesized respectively.

Reference Example Compound 70-1

N-[4-[4-(3-chlorophenyl)-2-ethyl-1,3-thiazol-5-yl]-2-pyridyl]acetamide melting point: 149–150° C.

Reference Example Compound 70-2

N-[4-[4-(3-chlorophenyl)-2-propyl-1,3-thiazol-5-yl]-2-pyridyl]acetamide melting point: 144–145° C.

Reference Example Compound 70-3

N-[4-[4-(3-chlorophenyl)-2-[4-(methylthio)phenyl]-1,3-thiazol-5-yl]-2-pyridyl]acetamide melting point: 207–208° C.

Reference Example Compound 70-4

N-[4-[2-ethyl-4-(2-thienyl)-1,3-thiazol-5-yl]-2-pyridyl]benzamide melting point: 116–117° C.

Reference Example compound 70-5

N-[4-[4-(3-chlorophenyl)-2-[4-(methylthio)phenyl]-1,3-thiazol-5-yl]-2-pyridyl]pivalamide melting point: 119–120° C.

Reference Example 71

N-[4-[4-(3-chlorophenyl)-2-(4-methylsulfonylphenyl)-1,3-thiazol-5-yl]-2-pyridyl]acetamide To a solution of N-[4-[4-(3-chlorophenyl)-2-[4-(methylthio)phenyl]-1,3-thiazol-5-yl]-2-pyridyl]acetamide (0.30 g, 0.66 mmol) in N,N-dimethylformamide (10 mL) was added 70% m-chloroperbenzoic acid (0.34 g, 1.4 mmol) and the mixture was stirred at room temperature for 2 hrs. Into the reaction mixture was poured aqueous sodium hydrogen carbonate solution and the mixture was extracted with ethyl acetate. The extract was washed with water, dried and the solvent was evaporated. The residue was purified by silica gel column chromatography (ethyl acetate) and washed with ethyl acetate-isopropyl ether to give the title compound (0.18 g, yield 55%).

melting point: 216–217° C.

Reference Example 72

In accordance with Reference Example 71 and using N-[4-[4-(3-chlorophenyl)-2-[4-(methylthio)phenyl]-1,3-thiazol-5-yl]-2-pyridyl]propionamide instead of N-[4-[4-(3-chlorophenyl)-2-[4-(methylthio)phenyl]-1,3-thiazol-5-yl]-2-pyridyl]acetamide, the following Reference Example compound 72 was synthesized.

Reference Example Compound 72

N-[4-[4-(3-chlorophenyl)-2-(4-methylsulfonylphenyl)-1,3-thiazol-5-yl]-2-pyridyl]propionamide melting point: 224–225° C.

Reference Example 73

4-(3-chlorophenyl)-2-ethyl-5-[2-(phenylmethylthio)-4-pyridyl]-1,3-thiazole

Sodium hydride (0.24 g, 6.0 mmol) was washed twice with hexane and suspended in N,N-dimethylformamide (10 mL). Phenylmethylthiol (0.58 mL, 4.9 mmol) was added to the suspension at 0° C. and the mixture was stirred at the same temperature for 1 hr. To the obtained solution was added a solution of 4-(3-chlorophenyl)-2-ethyl-5-(2-fluoro-4-pyridyl)-1,3-thiazole (0.78 g, 2.5 mmol) in N,N-dimethylformamide (6 mL) at the same temperature and the mixture was further stirred at room temperature for 1 hr. To the reaction mixture was added 8N aqueous sodium hydroxide solution (5 mL) and the mixture was extracted with isopropyl ether. The extract was washed with saturated aqueous sodium hydrogen carbonate solution and saturated brine, dried and the solvent was evaporated. The residue was purified by silica gel column chromatography (hexane-ethyl acetate=9:1) to give the title compound (0.56 g, yield 54%). Oil.

$^1$H-NMR (CDCl$_3$) δ: 1.44 (3H, t, J=7.6 Hz), 3.07 (2H, q, J=7.6 Hz), 4.39 (2H, s), 6.84–6.87 (1H, m), 7.10–7.11 (1H, m), 7.18–7.41 (8H, m), 7.58–7.60 (1H, m), 8.34–8.37 (1H, m).

Reference Example 74

N-[5-(2-cyclopentylamino-4-pyridyl)-4-(3-methylphenyl)-1,3-thiazol-2-yl]-N'-phenylurea To a solution of [5-(2-cyclopentylamino-4-pyridyl)-4-(3-methylphenyl)-1,3-thiazol-2-yl]amine (0.43 g, 1.2 mmol) in N,N-dimethylacetamide (10 mL) was added phenyl isocyanate (0.19 mL, 1.8 mmol) and the mixture was stirred at 80° C. for 1 hr. Into the reaction mixture was poured aqueous sodium hydrogen carbonate solution and the mixture was extracted with ethyl acetate. The extract was washed with saturated brine, dried and concentrated. The residue was purified by silica gel column chromatography (hexane-ethyl acetate=1:1). The obtained crude crystals were recrystallized from ethyl acetate to give the title compound (0.23 g, yield 39%).

melting point: 198–199° C.

The compounds produced in Reference Examples 62–74 are shown in Tables 3 to 5.

TABLE 3

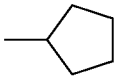

| Ex. compound | R³ | W | Z | R¹ | R² | melting point/° C. |
|---|---|---|---|---|---|---|
| 62 | 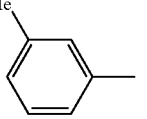 | — | —NH— | —NHMe | 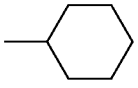 | 170–172 |
| 63 | 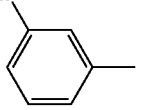 | — | —NH— | —NHMe | 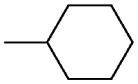 | 211–212 |
| 64-1 |  | — | —NH— | —NH₂ | 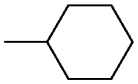 | 194–195 |
| 64-2 | 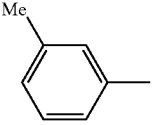 | — | —NH— | —CH₂Me | 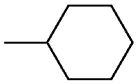 | 110–112 |
| 64-3 | 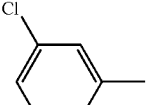 | — | —NH— | —CH₂Me | 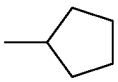 | 106–107 |
| 65-1 | 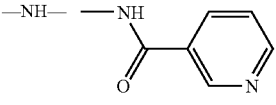 | — | —NH— | 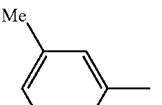 | 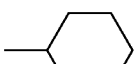 | 215–216 |
| 65-2 | 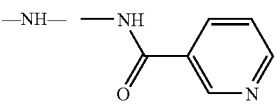 | — | —NH— | 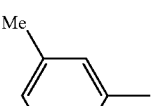 | 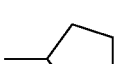 | 201–203 |
| 65-3 | 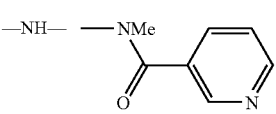 | — | —NH— | 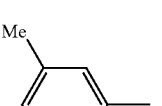 | Me | 150–151 |

TABLE 3-continued
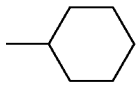
| Ex. compound | R³ | W | Z | R¹ | R² | melting point/° C. |
|---|---|---|---|---|---|---|
| 65-4 | 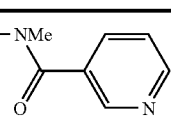 | — | —NH— | 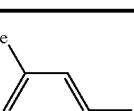 | 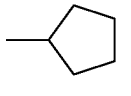 | 135–136 |
| 66-1 | 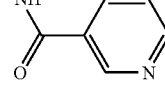 | — | —NH— | 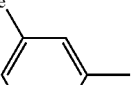 | 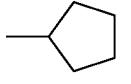 | 213–214 |
| 66-2 | 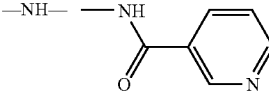 | — | —NH— | 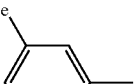 | 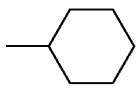 | 219–221 |
| 67-1 | 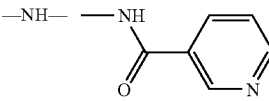 | — | —NH— | 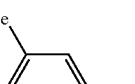 | 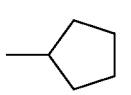 | 242–243 |
| 67-2 | 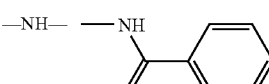 | — | —NH— |  | 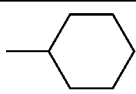 | 176–177 |
TABLE 4
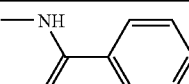
| Ex. compound | R³ | W | Z | R¹ | R² | melting point/° C. |
|---|---|---|---|---|---|---|
| 67-3 | 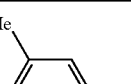 | — | —NH— | (structure) | (structure) | 191–192 |

TABLE 4-continued
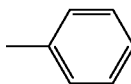
| Ex. compound | R³ | W | Z | R¹ | R² | melting point/° C. |
|---|---|---|---|---|---|---|
| 68-1 | 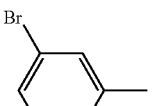 | —CH₂CO— | —NH— | —CH₂Me | 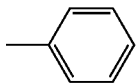 Br | 97–99 |
| 68-2 | 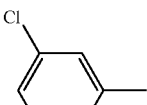 | —CH₂CO— | —NH— | —CH₂Me | 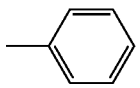 Cl | 111–112 |
| 68-3 | 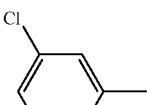 | —CH₂CO— | —NH— | —Me | 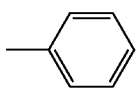 Cl | 99–101 |
| 68-4 | 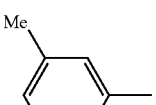 | —CH₂CO— | —NH— | —(CH₂)₃Me | 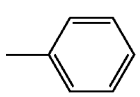 Me | 92–93 |
| 68-5 | 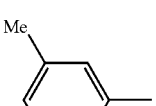 | —CH₂CO— | —NH— | —Me | 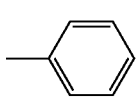 Me | 114–115 |
| 68-6 | 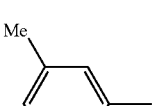 | —CH₂CO— | —NH— | —H | 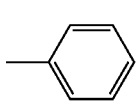 Me | 135–136 |
| 68-7 | 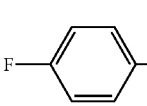 | —CH₂CO— | —NH— | —CH₂Me | 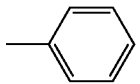 F | 178–179 |
| 68-8 | 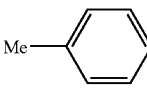 | —CH₂CO— | —NH— | —CH₂Me | 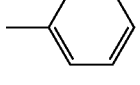 Me | 128–129 |
| 68-9 | 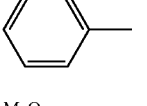 | —CH₂CO— | —NH— | —CH₂Me | 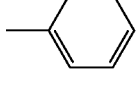 | 162–163 |
| 68-10 | 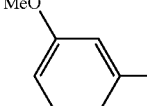 | —CH₂CO— | —NH— | —CH₂Me | MeO— | 128–129 |

TABLE 4-continued
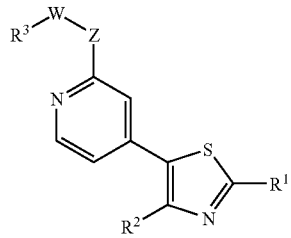
| Ex. compound | R³ | W | Z | R¹ | R² | melting point/° C. |
|---|---|---|---|---|---|---|
| 69-1 | —CH₂Me | —CO— | —NH— | —CH₂Me | 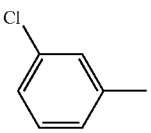 | 132–133 |
| 69-2 | —CH₂Me | —CO— | —NH— | —Me | 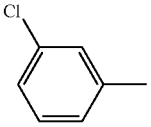 | 134–135 |
TABLE 5
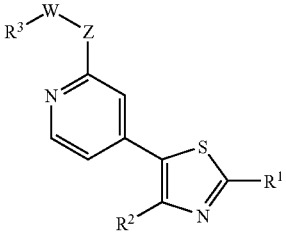
| Ex. compound | R³ | W | Z | R¹ | R² | melting point/° C. |
|---|---|---|---|---|---|---|
| 69-3 | —CH₂Me | —CO— | —NH— | —(CH₂)₂Me | 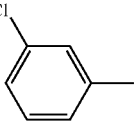 | 103–104 |
| 69-4 | —CH₂Me | —CO— | —NH— | 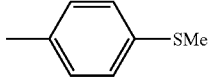 | 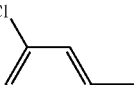 | 187–188 |
| 69-5 | —CH₂Me | —CO— | —NH— | —CH₂Me | 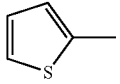 | 187–188 |
| 70-1 | —Me | —CO— | —NH— | —CH₂Me | 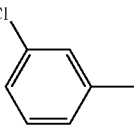 | 149–150 |

TABLE 5-continued

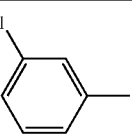

| Ex. compound | R³ | W | Z | R¹ | R² | melting point/° C. |
|---|---|---|---|---|---|---|
| 70-2 | —Me | —CO— | —NH— | —(CH₂)₂Me | 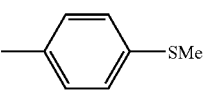 | 144–145 |
| 70-3 | —Me | —CO— | —NH— | 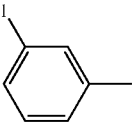 —SMe | 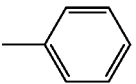 | 207–208 |
| 70-4 | 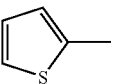 | —CO— | —NH— | —CH₂Me |  | 116–117 |
| 70-5 | 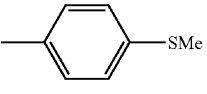 Me, Me, Me | —CO— | —NH— | 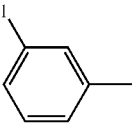 —SMe | 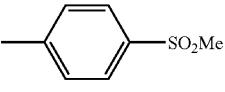 | 119–120 |
| 71 | —Me | —CO— | —NH— | 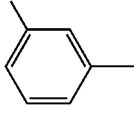 —SO₂Me | 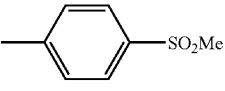 | 216–217 |
| 72 | —CH₂Me | —CO— | —NH— | 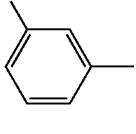 —SO₂Me | 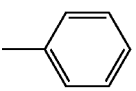 | 224–225 |
| 73 | 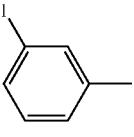 | —CH₂— | —S— | —CH₂Me | 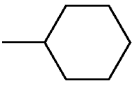 | oil |
| 74 |  | — | —NH— | —NHCONH—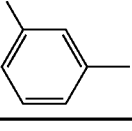 | (Cl-phenyl) | 198–199 |

Reference Example 75

Ethyl 2-acetyl-3-(dimethylamino)acrylate

Ethyl acetoacetate (79 mL, 0.62 mol) was added to N,N-dimethylformamide dimethylacetal (100 mL, 0.68 mol) and the mixture was heated under reflux for 1 hr. The excess amount of acetal was evaporated under reduced pressure and the residue was subjected to distillation under reduced pressure to give the title compound (85 g, yield 74%).

boiling point 125–130° C. (400 Pa)

¹H-NMR (CDCl₃) δ: 1.33 (3H, t, J=7.1 Hz), 2.33 (3H, s), 3.04 (6H, br s), 4.23 (2H, q, J=7.1 Hz), 7.68 (1H, s).

Reference Example 76

Ethyl 2,4-dimethyl-5-pyrimidinecarboxate

Acetamidine hydrochloride was added to a 10% sodium ethoxide-ethanol solution (410 mL, 0.53 mol) at room temperature. Then, ethyl 2-acetyl-3-(dimethylamino)acrylate (98 g, 0.53 mol) was added to the mixture, and the mixture was heated under reflux for 24 hrs. Ethanol was evaporated under reduced pressure. Water was added to the residue and the mixture was extracted with ethyl acetate. The extract was washed with water, dried and the solvent was evaporated. The residue was distilled under reduced pressure to give the title compound (73 g, yield 76%).
boiling point 93–98° C. (130 Pa)
$^1$H-NMR (CDCl$_3$) δ: 1.42 (3H, t, J=7.1 Hz), 2.75 (3H, s), 2.80 (3H, s), 4.41 (2H, q, J=7.1 Hz), 9.05 (1H, s).

Reference Example 77

2,4-dimethyl-5-pyrimidinecarboxylic acid

A solution of potassium hydroxide (67 g, 1.0 mol) in 95% ethanol (300 mL) was added to a solution of ethyl 2,4-dimethyl-5-pyrimidinecarboxate (73 g, 0.40 mol) in 95% ethanol (100 mL) and the mixture was heated under reflux for 5 hrs. Ethanol was evaporated under reduced pressure, and the residue was dissolved in water, and the aqueous solution was acidified with conc. hydrochloric acid. Precipitated solids were collected by filtration, washed with water and dried to give the title compound (36 g, yield 58%).
$^1$H-NMR (CDCl$_3$) δ: 2.63 (3H, s), 2.69 (3H, s), 8.97 (1H, s).

Reference Example 78

2,4-dimethylpyrimidine 2,4-Dimethyl-5-pyrimidinecarboxylic acid was heated at 160° C. for 4 hrs. The reaction mixture was distilled under atmospheric pressure to give the title compound (17 g, yield 49%).
boiling point 152–153° C.
$^1$H-NMR (CDCl$_3$) δ: 2.50 (3H, s), 2.70 (3H, s), 6.98 (1H, d, J=5.1 Hz), 8.49 (1H, d, J=5.1 Hz).

Reference Example 79 tert-butyl 4-methyl-2-pyrimidinylcarbamate

Di(tert-butyl) dicarbamate (12 mL, 50 mmol) was added dropwise to a solution of 4-methyl-2-pyrimidinylamine (5.0 g, 46 mmol) in tert-butanol over 1 hr. and the solution was stirred at room temperature for 14 hrs. The solvent was evaporated under reduced pressure and the obtained residue was purified by silica gel column chromatography (hexane-ethyl acetate=1:1). Crystallization from isopropyl ether-hexane gave the title compound (6.7 g, yield 70%).
melting point: 87–88° C.

Reference Example 80

1-(3-methylphenyl)-2-(4-pyrimidinyl)ethenol

A solution of diisopropylamine (16 mL, 0.12 mol) in anhydrous tetrahydrofuran (100 mL) was cooled to −50° C. and, with stirring, a 1.6 M n-butyl lithium in hexane solution (73 mL, 0.117 mol) was added dropwise. After the completion of the dropwise addition, the mixture was stirred for 10 min. Then, a solution of 4-methylpyrimidine (10 g, 0.11 mol) in anhydrous tetrahydrofuran (10 mL) was added dropwise at −30° C. The mixture was stirred for 0.5 hrs. and the reaction mixture was cooled to −78° C. A solution of N-(3-methylbenzoyl)propyleneimine (19 g, 0.11 mol) in anhydrous tetrahydrofuran (10 mL) was added dropwise. After the completion of the dropwise addition, the mixture was stirred at −78° C. for 2 hrs. The reaction mixture was heated to room temperature, and water (100 mL) was added. The mixture was extracted with ethyl acetate. The extract was washed with water, dried and the solvent was evaporated. The obtained residue was purified by silica gel column chromatography (hexane-ethyl acetate=7:3). Crystallization from isopropyl ether gave the title compound (11 g, yield 49%).
melting point: 66–67° C.

Reference Example 81

In accordance with Reference Example 80 and using 2,4-dimethylpyrimidine and tert-butyl 4-methyl-2-pyrimidinylcarbamate instead of 4-methylpyrimidine, the following Reference Example compounds 81-1 and 81-2 were synthesized respectively.

Reference Example Compound 81-1

1-(3-methylphenyl)-2-(2-methyl-4-pyrimidinyl)ethenol melting point: 88–89° C.

Reference Example Compound 81-2 tert-butyl 4-[2-hydroxy-2-(3-methylphenyl)ethenyl]-2-pyrimidinylcarbamate melting point: 194–195° C.

Example 1

JNK Inhibitor 1

| | |
|---|---|
| (1) compound of Reference Example 35 | 50 mg |
| (2) lactose | 34 mg |
| (3) corn starch | 10.6 mg |
| (4) corn starch (paste) | 5 mg |
| (5) magnesium stearate | 0.4 mg |
| (6) carboxymethylcellulose calcium | 20 mg |
| total | 120 mg |

The above-mentioned (1)–(6) were mixed according to a conventional method and the mixture was punched out by a tableting machine to give tablets.

Example 2

JNK Inhibitor 2

| | |
|---|---|
| (1) compound of Reference Example 35 | 10.0 mg |
| (2) lactose | 60.0 mg |
| (3) corn starch | 35.0 mg |
| (4) gelatin | 3.0 mg |
| (5) magnesium stearate | 2.0 mg |

A mixture of the compound of Reference Example 35 (10.0 mg), lactose (60.0 mg) and corn starch (35.0 mg) was granulated using a 10% aqueous gelatin solution (0.03 ml, 3.0 mg as gelatin) and passed through a 1 mm mesh sieve. The granules were dried at 40° C. and passed through the sieve again. The thus-obtained granules were mixed with magnesium stearate (2.0 mg) and compressed. The obtained core tablets were coated with a sugar coating of an aqueous suspension of sucrose, titanium dioxide, talc and gum arabic. The coated tablet were polished with bee's wax to give coated tablets.

Example 3

JNK Inhibitor 3

| | |
|---|---|
| (1) compound of Reference Example 35 | 10.0 mg |
| (2) lactose | 70.0 mg |
| (3) corn starch | 50.0 mg |
| (4) soluble starch | 7.0 mg |
| (5) magnesium stearate | 3.0 mg |

The compound of Reference Example 35 (10.0 mg) and magnesium stearate (3.0 mg) were granulated using an aqueous soluble starch solution (0.07 ml, 7.0 mg as soluble starch), and the granules were dried and mixed with lactose (70.0 mg) and corn starch (50.0 mg). The mixture was compressed to give tablets.

Example 4

JNK Inhibitor 4

| | |
|---|---|
| (1) compound of Reference Example 35 | 5.0 mg |
| (2) sodium chloride | 20.0 mg |
| (3) distilled water | to make total amount 2.0 ml |

The compound of Reference Example 35 (5.0 mg) and sodium chloride (20.0 mg) were dissolved in distilled water, and water was added to the solution to make the total amount 2.0 ml. The solution was filtered and filled in a 2 ml ampoule under aseptic conditions. The ampoule was sterilized and sealed to give a solution for injection.

Reference Formulation Example 1

Concomitant Drug

| | |
|---|---|
| (1) rofecoxib | 5.0 mg |
| (2) sodium chloride | 20.0 mg |
| (3) distilled water | to make total amount 2.0 ml |

Rofecoxib (5.0 mg) and sodium chloride (20.0 mg) are dissolved in distilled water and water is added to the solution to make the total amount 2.0 ml. The solution is filtered and filled in a 2 ml ampoule under aseptic conditions. The ampoule is sterilized and sealed to give a solution for injection.

Reference Formulation Example 2

Concomitant Drug

| | |
|---|---|
| (1) rofecoxib | 50 mg |
| (2) lactose | 34 mg |
| (3) corn starch | 10.6 mg |
| (4) corn starch (paste) | 5 mg |
| (5) magnesium stearate | 0.4 mg |
| (6) carboxymethylcellulose calcium | 20 mg |
| total | 120 mg |

The above-mentioned (1)–(6) were mixed according to a conventional method and the mixture was punched out by a tableting machine to give tablets.

Example 5

Combination Drug

Any preparation prepared in Examples 1–4 and a preparation of Reference Formulation Example 1 or 2 are combined.

Example 6

[4-(3-methylphenyl)-5-(4-pyrimidinyl)-1,3-thiazol-2-yl]amine

To a solution (70 mL) of 1-(3-methylphenyl)-2-(4-pyrimidinyl)ethenol (3.0 g, 14 mmol) and sodium acetate (2.32 g, 28.26 mmol) in acetic acid was added dropwise a solution (70 mL) of bromine (0.72 mL, 14 mmol) in acetic acid at room temperature over 30 min. The mixture was stirred at room temperature for 2 hrs. Acetic acid was evaporated under reduced pressure, and aqueous sodium hydrogen carbonate solution was added to the residue. The mixture was extracted with ethyl acetate and the extract was dried and concentrated. The residue was dissolved in N,N-dimethylformamide (15 mL), and thiourea (1.1 g, 16 mmol) was added to the solution. The reaction mixture was stirred at room temperature for 14 hrs. Aqueous sodium hydrogen carbonate solution was added, and the precipitated solids were collected by filtration. The solids were washed with water, dried and subjected to recrystallization from ethyl acetate to give the title compound (3.4 g, yield 89%).

melting point: 241–242° C.

Example 7

In accordance with Example 6 and using 1-(3-methylphenyl)-2-(2-methyl-4-pyrimidinyl)ethenol and tert-butyl 4-[2-hydroxy-2-(3-methylphenyl)ethenyl]-2-pyrimidinylcarbamate instead of 1-(3-methylphenyl)-2-(4-pyrimidinyl)ethenol, the following Example compounds 7-1 and 7-2 were synthesized.

Example Compound 7-1

[4-(3-methylphenyl)-5-(2-methyl-4-pyrimidinyl)-1,3-thiazol-2-yl]amine melting point: 185–186° C.

Example Compound 7-2 tert-butyl 4-[2-amino-4-(3-methylphenyl)-1,3-thiazol-5-yl]-2-pyrimidinylcarbamate melting point: 262–264° C.

Example 8 methyl 4-[[[4-(3-methylphenyl)-5-(4-pyrimidinyl)-1,3-thiazol-2-yl]amino]carbonyl]benzoate Methyl 4-chloroformylbenzoate (1.1 g, 5.6 mmol) was added to a solution of [4-(3-methylphenyl)-5-(4-pyrimidinyl)-1,3-thiazol-2-yl]amine and 4-dimethylaminopyridine (0.14 g, 1.1 mmol) in N,N-dimethylacetamide (10 mL), and the mixture was stirred at 70° C. for 14 hrs. Aqueous sodium hydrogen carbonate solution was added to the reaction mixture and the precipitated solids were collected by filtration. Crude crystals were washed with water, dried and recrystallized from pyridine to give the title compound (1.0 g, yield 65%).

melting point: 339–341° C.

Example 9

4-[[[4-(3-methylphenyl)-5-(4-pyrimidinyl)-1,3-thiazol-2-yl]amino]carbonyl]benzoic acid To a suspension of methyl 4-[[[4-(3-methylphenyl)-5-(4-pyrimidinyl)-1,3-thiazol-2-yl]amino]carbonyl]benzoate (0.50 g, 1.2 mmol) in ethanol (10 mL) was added 2N aqueous sodium hydroxide solution (1.2 mL), and the mixture was stirred at room temperature for 2 hrs. The reaction mixture was acidified with 2N hydrochloric acid and the precipitated solids were collected by filtration. Crude crystals were washed with water and dried to give the title compound (0.40 g, yield 0.82%).

melting point: 380–381° C.

Example 10

N-[4-(3-methylphenyl)-5-(2-methyl-4-pyrimidinyl)-1,3-thiazol-2-yl]acetamide

To a solution of [4-(3-methylphenyl)-5-(2-methyl-4-pyrimidinyl)-1,3-thiazol-2-yl]amine (0.50 g, 1.8 mmol) and 4-dimethylaminopyridine (0.065 g, 0.53 mmol) in N,N-dimethylacetamide (10 mL) was added acetylchloride (0.19 mL, 2.7 mmol), and the mixture was stirred at 80° C. for 14 hrs. Into the reaction mixture was poured aqueous sodium hydrogen carbonate solution and the mixture was extracted with ethyl acetate. The extract was washed with saturated brine, dried and concentrated. The resulting crystals were recrystallized from ethyl acetate to give the title compound (0.35 g, yield 61%).

melting point: 230–231° C.

Example 11

N-[5-(2-methyl-4-pyrimidinyl)-4-(3-methylphenyl)-1,3-thiazol-2-yl]-N'-phenylurea To a solution of [5-(2-methyl-4-pyrimidinyl)-4-(3-methylphenyl)-1,3-thiazol-2-yl]amine (0.50 g, 1.8 mmol) in N,N-dimethylacetamide (10 mL) was added phenylisocyanate (0.29 mL, 2.7 mmol), and the mixture was stirred at 80° C. for 2 hrs. Into the reaction mixture was poured aqueous sodium hydrogen carbonate solution, and the mixture was extracted with ethyl acetate. The extract was washed with saturated brine, dried and concentrated. The resulting crystals were recrystallized from ethyl acetate-hexane to give the title compound (0.55 g, yield 78%).

melting point: 141–142° C.

Example 12

N-[4-(3-methylphenyl)-5-[2-(phenylacetylamino)-4-pyrimidinyl]-1,3-thiazol-2-yl]phenylacetamide To a solution of tert-butyl 4-[2-amino-4-(3-methylphenyl)-1,3-thiazol-5-yl]-2-pyrimidinylcarbamate (0.50 g, 1.3 mmol) in N,N-dimethylacetamide (5 mL) was added phenylacetylchloride (0.52 mL, 3.9 mmol) and the mixture was stirred at 80° C. for 14 hrs. Into the reaction mixture was poured aqueous sodium hydrogen carbonate solution, and the mixture was extracted with ethyl acetate. The extract was washed with saturated brine, dried and concentrated. The obtained residue was purified by silica gel column chromatography (hexane-ethyl acetate=7:3), and the obtained oil was recrystallized from ethyl ether to give the title compound (0.09 g, yield 13%).

melting point: 110–113° C.

The compounds prepared in Examples 6–12 are shown in Table 6.

TABLE 6

| Ex. compound | $R^1$ | $R^2$ | $R^3$ | melting point/° C. |
|---|---|---|---|---|
| 6 | —NH$_2$ | Me-(3-methylphenyl) | H— | 241–242 |

TABLE 6-continued

[Structure: pyrimidine with R³ at 2-position, connected at 4-position to thiazole bearing R¹ (2-position) and R² (4-position)]

| Ex. compound | R¹ | R² | R³ | melting point/° C. |
|---|---|---|---|---|
| 7-1 | —NH₂ | 3-Me-C₆H₄— | Me— | 185–186 |
| 7-2 | —NH₂ | 3-Me-C₆H₄— | Me₃C—OCONH— | 262–264 |
| 8 | —NHCO-C₆H₄-CO₂Me (para) | 3-Me-C₆H₄— | H— | 339–341 |
| 9 | —NHCO-C₆H₄-CO₂H (para) | 3-Me-C₆H₄— | H— | 380–381 |
| 10 | —NHCOMe | 3-Me-C₆H₄— | Me— | 230–231 |
| 11 | —NHCONH-C₆H₅ | 3-Me-C₆H₄— | Me— | 141–142 |
| 12 | —NHCOCH₂-C₆H₅ | 3-Me-C₆H₄— | C₆H₅-CH₂CONH— | 110–113 |

Reference Example 82

Cloning of Human JNK1 Gene and Preparation of Recombinant Baculovirus

Cloning of human JNK1 gene was performed by PCR method using a primer set

```
JNK1-U:
5'-ACAACTCGAGATAACATATGGCTCATCATCATCATCATAGCAGAAGCAAGCGTGACAAC-3'   [SEQ ID No.1]

JNK1-L:
5'-TCCCGGGTACCTCACTGCTGCACCTGTGCTAA-3'                                [SEQ ID No.2]
``` made by the use of kidney cDNA (Toyobo, QUICK-Clone cDNA) as a template and referring to the base sequence of JNK1 gene reported by Derijard, B. et al. (*Cell*, 76, 1025–1037 (1994)).

A PCR reaction was performed by a Hot Start method using AmpliWax PCR Gem 100 (Takara Shuzo). As the lower mixed solution, 2 mL 10×LA PCR Buffer, 3 mL 2.5 mM dNTP solution, each 2.5 mL of 12.5 mM primer solutions, 2 µL 25 mM MgCl$_2$ solution and 8 mL sterile distilled water were mixed. As the upper mixed solution, 1 mL human kidney cDNA (1 ng/mL) as a template, 3 mL 10×LA PCR Buffer, 5 mL 2.5 mM dNTP solution, 3 µL 25 mM MgCl$_2$ solution, 0.5 mL TaKaRa LA Taq DNA polymerase (Takara Shuzo), and 17.5 mL sterile distilled water were mixed. One AmpliWax PCR Gem 100 (Takara Shuzo) was added to the prepared lower mixed solution and the mixture was treated at 70° C. for 5 min and for 5 min in ice and, thereafter, the upper mixed solution was added to prepare a reaction solution for PCR. A tube containing the reaction solution was set at a thermal cycler (Perkin Elmer), which was treated at 95° C. for 2 min. Further, after repeating 35 times a cycle of 15 seconds at 95° C. and 2 minutes at 68° C., the treatment was performed at 72° C. for 8 minutes. The resulting PCR product was subjected to agarose gel (1%) electrophoresis, 1.2 kb DNA fragment containing JNK1 gene was recovered from the gel, which was digested with restriction enzymes KpnI, XhoI and inserted into 4.8 kb XhoI-KpnI fragment of plasmid pFAST-BAC1 (GibcoBRL) to give plasmid pFBJNK1. The plasmid pFBJNK1 and BAC-TO-BAC Baculovirus Expression System (GibcoBRL) were used to prepare the recombinant baculovirus virusstock BAC-HJNK1.

Reference Example 83

Cloning of Human MKK7 Gene and Preparation of Recombinant Baculovirus

Cloning of human MKK7 gene was performed by PCR method using a primer set made by the use of pancreatic cDNA (Toyobo, QUICK-Clone cDNA) as a template and referring to the base sequence of MKK7 gene reported by Foltz, I. N. et al. (*J. Biol. Chem.*, 273, 9344–9351 (1998)).

A PCR reaction was performed by a Hot Start method using AmpliWax PCR Gem 100 (Takara Shuzo). As the lower mixed solution, 2 mL 10×LA PCR Buffer, 3 mL 2.5 mM dNTP solution, each 2.5 mL of 12.5 mM primer solutions, 2 mL 25 mM MgCl$_2$ solution and 8 mL sterile distilled water were mixed. As the upper mixed solution, 1 mL human pancreatic cDNA (1 ng/mL) as a template, 3 mL 10×LA PCR Buffer, 5 mL 2.5 mM dNTP solution, 3 mL 25 mM MgCl$_2$ solution, 0.5 mL TaKaRa LA Taq DNA polymerase (Takara Shuzo), and 17.5 mL sterile distilled water were mixed. One AmpliWax PCR Gem 100 (Takara Shuzo) was added to the prepared lower mixed solution and the mixture was treated at 70° C. for 5 min and for 5 min in ice and, thereafter, the upper mixed solution was added to prepare a reaction solution for PCR. A tube containing the reaction solution was set at a thermal cycler (Perkin Elmer), which was treated at 95° C. for 2 min. Further, after repeating 35 times a cycle of 15 seconds at 95° C. and 2 minutes at 68° C., the treatment was performed at 72° C. for 8 minutes. The resulting PCR product was subjected to agarose gel (1%) electrophoresis, 1.3 kb DNA fragment containing MKK7 gene was recovered from the gel, which was inserted into pT7Blue-T vector (Novagen) to give plasmid pHMKK7.

In order to prepare a constitutively active MKK7 (from Ser to Asp at 271 position, from Thr to Asp at position 275), as reported by Wang, Y. et al. (*J. Biol. Chem.*, 273, 5423–5426 (1998)), a primer set

```
CAM7-U:                                                               [SEQ ID No.5]
5'-GGCCGCCTGGTGGACGACAAAGCCAAGGACCGGAGCGCCGGCTG-3'

CAM7-L:                                                               [SEQ ID No.6]
5'-CAGCCGGCGCTCCGGTCCTTGGCTTTGTCGTCCACCAGGCGGCC-3'
``` was used to introduce a mutation by QuikChange Site-Directed Mutagenesis Kit (Stratagene), to obtain pcaMKK7.

4.8 kb EcoRI-XbaI fragment of the plasmid pFASTBAC1 (GibcoBRL) and the 1.3 kb EcoRI-XbaI fragment of the above plasmid pcaMKK7 were ligated to make the plasmid pFBcaMKK7.

```
MKK7-U:
5'-ACCAGAATTCATAACATATGGCTCATCATCATCATCATGCGGCGTCCTCCCTGGAACAG-3'   [SEQ ID No.3]

MKK7-L:
5'-ACCCTCTAGACAAGCAGCTACCTGAAGAAGG-3'                                 [SEQ ID No.4]
```

The plasmid pFBcaMKK7 and BAC-TO-BAC Baculovirus Expression System (GibcoBRL) were used to prepare the recombinant baculovirus virusstock BAC-caMKK7.

Reference Example 84

Cloning of Human c-Jun Gene

For Cloning of Human c-Jun gene, the Gene Encoding N terminal 79 amino acids of c-Jun was amplified by PCR method using a primer set:

```
c-Jun-U: 5'-AAAAGAATTCATGACTGCAAAGATGGAAACGACC-3'    [SEQ ID No.7]

c-Jun-L: 5'-AAAAGCGGCCGCTCACAGGCGCTCCAGCTCGGGCGACGC-3'   [SEQ ID No.8]
``` made by the use of skeletal muscle cDNA (Toyobo, QUICK-Clone cDNA) as a template and referring to the base sequence of c-Jun gene reported by Hattori, K. et al. (*Proc. Natl. Acad. Sci. U.S. A.*, 85, 9148–9152 (1988)).

A PCR reaction was performed by a Hot Start method using AmpliWax PCR Gem 100 (Takara Shuzo). As the lower mixed solution, 2 mL 10×Pyrobest PCR Buffer, 3 mL 2.5 mM dNTP solution, each 2.5 mL of 12.5 mM primer solutions and 10 mL sterile distilled water were mixed. As the upper mixed solution, 1 mL human skeletal muscle cDNA (1 ng/mL) as a template, 3 mL 1033 Pyrobest PCR Buffer, 2 mL 2.5 mM dNTP solution, 0.5 mL TaKaRa Pyrobest DNA polymerase (Takara Shuzo), and 24.5 mL sterile distilled water were mixed. One AmpliWax PCR Gem 100 (Takara Shuzo) was added to the prepared lower mixed solution and the mixture was treated at 70° C. for 5 min and for 5 min in ice and, thereafter, the upper mixed solution was added to prepare a reaction solution for PCR. A tube containing the reaction solution was set at a thermal cycler (Perkin Elmer), which was treated at 95° C. for 2 min. Further, after repeating 35 times a cycle of 15 seconds at 95° C. and 30 seconds at 68° C., the treatment was performed at 72° C. for 8 minutes. The resulting PCR product was subjected to agarose gel (1%) electrophoresis, 240 bp DNA fragment containing c-Jun gene was recovered from the gel, which was digested with restriction enzymes EcoRI, NotI and inserted into 4.9 kb EcoRI-NotI fragment of plasmid pGEX6P-1 (Amersham Pharmacia Biotech) to give plasmid pGEJun.

Reference Example 85

Preparation of Active JNK1

The Sf-21 cells were seeded on 100 mL Sf-900 II SFM medium (GibcoBRL) supplemented with 10% fetal bovine serum to $1 \times 10^6$ cells/mL and cultured at 27° C. for 24 hours. After each 0.2 mL of the virusstock BAC-HJNK1 and BAC-caMKK7 of recombinant baculovirus were added, the culturing was further performed for 60 hours. After the cells were separated from the culturing solution by centrifugation (3000 rpm, 10 min), the cells were washed twice with PBS. After the cells were suspended in 10 ml Lysis buffer (25 mM HEPES (pH 7.5), 1% Triton-X, 130 mM NaCl, 1 mM EDTA, 1 mM DTT, 25 mM b-glycerophosphate, 20 mM leupeptin, 1 mM APMSF, 1 mM Sodium orthovanadate), the cells were lysed by treating 4 times in a homogenizer (POLYTRON) at 20000 rpm for 30 seconds. From the supernatant obtained by centrifugation (40000 rpm, 45 minutes), active JNK1 was purified using Anti-FLAG M2 Affinity Gel (Sigma)

Reference Example 86

Preparation of Recombinant c-Jun

*Escherichia coli* JM109 (Toyobo) was transformed with plasmid pGEJun to give ampicillin resistant strain pGEJun/JM109. The pGEJun/JM109 strain was cultured overnight at 200 rpm, 37° C. in 150 mL of LB medium (10 g/L trypton, 5 g/L east extract, 10 g/L sodium chloride) containing 50 mg/mL ampicillin. The culture solution (15 mL) was added to fresh LB medium (150 mL), cultured at 37° C., 200 rpm for 2 hrs., added with 1 mM IPTG (Waco Pure Chemical Industries, Ltd.) and cultured for 6 hrs. The culture solution was centrifuged at 8000 rpm for 10 min. and bacterial cells were recovered, washed with PBS and lyophilized at −80° C. After suspending in 20 mL of lysis buffer (B-PER bacterial protein extraction reagent (Pierce Chemical Co.), Protease inhibitor Complete (Boehringer Ingelheim)), the solution was shaken at room temperature for 10 min., which was followed by centrifugal separation (14000 rpm, 15 min., 4° C.), and GST-cJun fusion protein was purified from the supernatant using Redipack GST Purification Module (Amersham Pharmacia Biotech).

Experimental Example 1

Measurement of JNK1 Enzyme Inhibitory Activity

A test compound (2.5 mL) dissolved in dimethyl sulfoxide was added to 37.5 mL reaction solution (25 mM HEPES, pH 7.5, 10 mM magnesium acetate) containing 50 ng active JNK1 and 1 mg c-Jun, and the mixture was maintained at 30° C. for 5 minutes. The reaction was initiated by adding 10 mL ATP solution (2.5 mM ATP, 0.1 mCi [g-$^{32}$P]ATP). After the reaction was performed at 30° C. for 60 minutes, the reaction was quenched by adding 50 mL 20% TCA solution. After the reaction solution was allowed to stand at 0° C. for 20 minutes, an acid insoluble fraction was transferred to GF/C filter (Packard Japan) using Cell Harvester (Packard Japan) and washed with 250 mM phosphoric acid. After drying at 45° C. for 60 minutes, 40 mL Microscint 0 (Packard Japan) was added and the radioactivity was measured with a TopCount (Packard Japan). The concentration of the test compound necessary for inhibiting $^{32}$P uptake into an acid insoluble fraction by 50% (IC$_{50}$ value) was calculated with PRISM 2.01 (Graphpad Software). The results are shown in Table 7.

TABLE 7

| Reference Example Compound No. | IC$_{50}$ (μM) |
| --- | --- |
| 29-1 | 0.033 |
| 32 | 0.11 |
| 34-1 | 0.097 |
| 39 | 0.14 |
| 40 | 0.21 |

Experimental Example 2

Measurement of TNF-α Production Inhibitory Activity

After THP-1 cells which had been cultured on RPMI 1640 medium (GibcoBRL) containing 1% inactivated fetal bovine serum and 10 mM HEPES (pH 7.5) were seeded on a 96-well plate to $1\times10^5$ cells/well, 1 mL test compound dissolved in DMSO was added. After incubation at 37° C. for 1 hour in a $CO_2$ incubator, LPS (Wako Pure Chemical Industries, Ltd.) was added to the final concentration 5 mg/mL. After cultured at 37° C. for 4 hours in a $CO_2$ incubator, the supernatant was obtained by centrifugation. The concentration of TNF-α in the supernatant was measured by ELISA kit (DIACLONE). The concentration of the test compound necessary for inhibiting TNF-α production by 50% ($IC_{50}$ value) was calculated using PRISM 2.01 (Graphpad Software). The results are shown in Table 8.

TABLE 8

| Reference Example Compound No. | $IC_{50}$ (μM) |
| --- | --- |
| 29-1 | 0.0020 |
| 32 | 0.10 |
| 34-1 | 0.057 |
| 39 | 0.0059 |
| 40 | 0.015 |

From the above results, it is clear that the Compound of the present invention has an excellent inhibitory activity against JNK and TNF-α production.

INDUSTRIAL APPLICABILITY

The Compound of the present invention has superior JNK inhibitory action and TNF-α production inhibitory action, and can be used as a prophylactic or therapeutic agent of c-Jun related diseases.

This application is based on a patent application No. 27570/2001 filed in Japan, the contents of which are all hereby incorporated by reference.

What is claimed is:

1. An optionally N-oxidized compound represented by the formula:

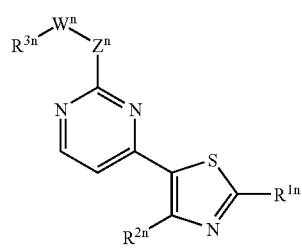

(In)

wherein $Z^n$ is a bond, $W^n$ is a bond, $R^{1n}$ in is a hydrogen atom, a hydrocarbon group optionally having substituent(s), a heterocyclic group optionally having substituent(s), an amino group optionally having substituent(s) or an acyl group, $R^{2n}$ is an aromatic group optionally having substituent (s), and $R^{3n}$ is a hydrogen atom, a hydrocarbon group optionally having substituent(s) or a heterocyclic group optionally having substituent (s) or a prodrug thereof.

2. An optionally N-oxidized compound represented by the formula:

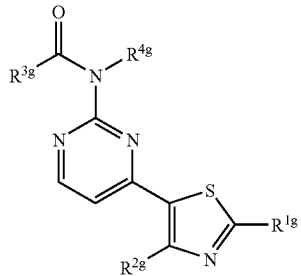

(Ig′)

wherein $R^{1g}$ is a hydrogen atom, a hydrocarbon group optionally having substituent(s), a heterocyclic group optionally having substituent(s), an amino group optionally having substituent(s) or an acyl group, $R^{2g}$ is an aromatic group optionally having substituent (s), $R^{3g}$ is a hydrocarbon group optionally having substituent(s) or a heterocyclic group optionally having substituent(s), and $R^{4g}$ is a hydrogen atom or a hydrocarbon group optionally having substituent(s) or a prodrug thereof.

3. A prodrug of the compound of claim 1.

4. A pharmaceutical agent containing a compound of claim 1 or a prodrug thereof.

5. A prodrug of the compound of claim 2.

6. A pharmaceutical agent containing a compound of claim 2 or a prodrug thereof.

* * * * *